US011478286B2

(12) United States Patent
Kowalczyk et al.

(10) Patent No.: US 11,478,286 B2
(45) Date of Patent: Oct. 25, 2022

(54) BONE FIXATION DEVICES

(71) Applicant: PARAGON ADVANCED TECHNOLOGIES, INC., Englewood, CO (US)

(72) Inventors: Gregory J. Kowalczyk, Little Silver, NJ (US); Selene G. Parekh, Cary, NC (US); Brian R. McLaughlin, Yarmouth, ME (US)

(73) Assignee: PARAGON ADVANCED TECHNOLOGIES, INC., Englewood, CO (US)

( * ) Notice: Subject to any disclaimer, the term of this patent is extended or adjusted under 35 U.S.C. 154(b) by 0 days.

(21) Appl. No.: 15/614,423

(22) Filed: Jun. 5, 2017

(65) Prior Publication Data
US 2017/0360488 A1 Dec. 21, 2017

Related U.S. Application Data

(60) Provisional application No. 62/425,363, filed on Nov. 22, 2016, provisional application No. 62/404,923, (Continued)

(51) Int. Cl.
| | | |
|---|---|---|
| *A61B 17/80* | (2006.01) | |
| *A61B 17/56* | (2006.01) | |
| *A61B 17/00* | (2006.01) | |

(52) U.S. Cl.
CPC ........ *A61B 17/8095* (2013.01); *A61B 17/809* (2013.01); *A61B 17/8061* (2013.01);
(Continued)

(58) Field of Classification Search
CPC ............. A61B 17/8095; A61B 17/809; A61B 17/8061; A61F 2002/4475; A61F 2002/4495; A61F 2/447; A61F 2/4455
See application file for complete search history.

(56) References Cited

U.S. PATENT DOCUMENTS

| | | |
|---|---|---|
| 5,211,664 A | 5/1993 | Tepic et al. |
| 5,360,448 A | 11/1994 | Thramann |

(Continued)

FOREIGN PATENT DOCUMENTS

| | | |
|---|---|---|
| FR | 2827157 A1 | 1/2003 |
| WO | 2012/109748 A1 | 8/2012 |

(Continued)

OTHER PUBLICATIONS

International Search Report and Written Opinion of the International Searching Authority of PCT/US2017/036004, dated Sep. 13, 2017.

(Continued)

*Primary Examiner* — Amy R Sipp
(74) *Attorney, Agent, or Firm* — Heslin Rothenberg Farley & Mesiti P.C.; Kristian E. Ziegler, Esq.

(57) ABSTRACT

There is a fixation device for promoting fusion and/or osteosynthesis of a first bone segment and a second bone segment, comprising a bone plate portion including an outer surface, an inner surface and at least one fixation aperture extending from the outer surface to the inner surface and a bone wedge portion extending from the plate portion at a first end and a free opposite end, the bone wedge portion comprising a porous architecture configured to promote bone ingrowth, the wedge portion defining first and second engagement surfaces for engaging the first bone segment and a second bone segment, respectively. There is also a method of manufacturing a fixation device for promoting fusion and/or osteosynthesis of a first bone segment and a second bone segment, a method of promoting fusion and/or osteosynthesis of a first bone segment and a second bone segment, and a fixation kit.

20 Claims, 74 Drawing Sheets

Related U.S. Application Data filed on Oct. 6, 2016, provisional application No. 62/345,536, filed on Jun. 3, 2016.

(52) U.S. Cl.
CPC .............. *A61B 2017/00526* (2013.01); *A61B 2017/561* (2013.01); *A61B 2017/565* (2013.01)

(56) References Cited

U.S. PATENT DOCUMENTS

| | | | |
|---|---|---|---|
| 5,650,108 A | 7/1997 | Nies et al. | |
| 5,856,367 A | 1/1999 | Barrows et al. | |
| 5,869,080 A | 2/1999 | McGregor et al. | |
| 5,876,452 A | 3/1999 | Athanasiou et al. | |
| 6,149,688 A | 11/2000 | Brosnahan et al. | |
| 6,206,924 B1 | 3/2001 | Timm | |
| 6,228,111 B1 | 5/2001 | Toermaelae et al. | |
| 6,235,225 B1 | 5/2001 | Okada et al. | |
| 6,432,107 B1 | 8/2002 | Ferree | |
| 6,436,426 B1 | 8/2002 | Liao et al. | |
| 6,511,511 B1 | 1/2003 | Slivka et al. | |
| 6,527,810 B2 | 3/2003 | Johnson et al. | |
| 6,530,956 B1 | 3/2003 | Mansmann | |
| 6,626,945 B2 | 9/2003 | Simon et al. | |
| 6,840,960 B2 | 1/2005 | Bubb | |
| 7,235,079 B2 | 6/2007 | Jensen et al. | |
| 7,241,313 B2 | 7/2007 | Unwin et al. | |
| 7,351,280 B2 | 4/2008 | Khairoun et al. | |
| 7,578,851 B2 | 8/2009 | Dong et al. | |
| 7,879,109 B2 | 2/2011 | Borden et al. | |
| 7,892,265 B2 | 2/2011 | Perez-Cruet et al. | |
| 7,910,690 B2 | 3/2011 | Ringeisen et al. | |
| 7,943,677 B2 | 5/2011 | Papangelou et al. | |
| 8,119,152 B2 | 2/2012 | Shikinami | |
| 8,292,967 B2 | 10/2012 | Brown et al. | |
| 8,337,873 B2 | 12/2012 | Mao | |
| 8,383,024 B2 | 2/2013 | Morrissette et al. | |
| 8,389,588 B2 | 3/2013 | Ringeisen et al. | |
| 8,445,554 B2 | 5/2013 | Ringeisen et al. | |
| 8,475,505 B2 | 7/2013 | Nebosky et al. | |
| 8,500,843 B2 | 8/2013 | Grohowski | |
| 8,529,625 B2 | 9/2013 | Farrar et al. | |
| 8,535,357 B2 | 9/2013 | Stone et al. | |
| 8,657,827 B2 | 2/2014 | Fitz et al. | |
| 8,700,198 B2 | 4/2014 | Conway et al. | |
| 8,715,366 B2 | 5/2014 | Borden | |
| 2003/0009225 A1 | 1/2003 | Khandkar et al. | |
| 2003/0065393 A1* | 4/2003 | Moumene .............. | A61F 2/447 623/17.11 |
| 2003/0199875 A1 | 10/2003 | Mingozzi et al. | |
| 2004/0082999 A1 | 4/2004 | Mathys, Jr. et al. | |
| 2004/0243237 A1 | 12/2004 | Unwin et al. | |
| 2004/0258732 A1 | 12/2004 | Shikinami | |
| 2005/0187555 A1 | 8/2005 | Biedermann et al. | |
| 2006/0111715 A1 | 5/2006 | Jackson | |
| 2006/0241763 A1 | 10/2006 | Paul et al. | |
| 2006/0276788 A1 | 12/2006 | Berry et al. | |
| 2007/0156240 A1 | 7/2007 | Tsuang et al. | |
| 2007/0161985 A1 | 7/2007 | Demakas et al. | |
| 2007/0179610 A1* | 8/2007 | Biedermann ......... | A61F 2/4465 623/16.11 |
| 2007/0203584 A1 | 8/2007 | Bandyopadhyay et al. | |
| 2008/0154314 A1* | 6/2008 | McDevitt .............. | A61F 2/0811 606/304 |
| 2008/0269893 A1 | 10/2008 | Bhatnagar et al. | |
| 2009/0187249 A1 | 7/2009 | Osman | |
| 2009/0240324 A1 | 9/2009 | Smith | |
| 2010/0042214 A1 | 2/2010 | Nebosky et al. | |
| 2010/0094420 A1 | 4/2010 | Growhowski, Jr. | |
| 2010/0161061 A1* | 6/2010 | Hunt .................... | A61F 2/2846 623/17.16 |
| 2010/0249851 A1 | 9/2010 | Kay et al. | |
| 2010/0262245 A1 | 10/2010 | Alfaro et al. | |
| 2011/0004307 A1 | 1/2011 | Ahn et al. | |
| 2011/0014081 A1* | 1/2011 | Jones .................... | A61F 2/3094 419/2 |
| 2011/0071635 A1 | 3/2011 | Zhang et al. | |
| 2011/0172775 A1 | 7/2011 | Flickinger et al. | |
| 2011/0282454 A1* | 11/2011 | Ullrich, Jr. ............ | A61F 2/4465 623/17.16 |
| 2011/0301709 A1 | 12/2011 | Kraus et al. | |
| 2012/0089197 A1 | 4/2012 | Anderson | |
| 2012/0271361 A1 | 10/2012 | Zhou et al. | |
| 2012/0271362 A1 | 10/2012 | Martineau et al. | |
| 2012/0330420 A1 | 12/2012 | Brodke et al. | |
| 2013/0022943 A1 | 1/2013 | Collins et al. | |
| 2013/0066435 A1 | 3/2013 | Averous et al. | |
| 2013/0090733 A1 | 4/2013 | Kraft et al. | |
| 2013/0116793 A1 | 5/2013 | Kloss | |
| 2013/0150965 A1 | 6/2013 | Taylor et al. | |
| 2013/0178900 A1 | 7/2013 | Fallin et al. | |
| 2013/0211533 A1 | 8/2013 | Fonte et al. | |
| 2014/0039565 A1 | 2/2014 | Martineau et al. | |
| 2014/0107785 A1 | 4/2014 | Geisler et al. | |
| 2014/0180432 A1 | 6/2014 | Conway et al. | |
| 2014/0188237 A1 | 7/2014 | McCormick et al. | |
| 2014/0257483 A1* | 9/2014 | Swann .................. | A61F 2/4455 623/17.11 |
| 2014/0277554 A1 | 9/2014 | Roman et al. | |
| 2015/0032220 A1 | 1/2015 | Tyber et al. | |
| 2015/0045903 A1 | 2/2015 | Neal | |
| 2015/0088201 A1 | 3/2015 | Massoudi | |
| 2015/0100126 A1 | 4/2015 | Melkent et al. | |
| 2015/0100129 A1 | 4/2015 | Waugh et al. | |
| 2015/0142066 A1 | 5/2015 | Shemwell et al. | |
| 2015/0150607 A1 | 6/2015 | Chen et al. | |
| 2015/0250513 A1 | 9/2015 | De Lavigne Sainte Suzanne | |
| 2016/0089138 A1 | 3/2016 | Early et al. | |
| 2016/0106544 A1 | 4/2016 | McWilliam et al. | |
| 2016/0166301 A1* | 6/2016 | Papangelou ......... | A61B 17/8095 623/23.5 |
| 2016/0270920 A1* | 9/2016 | Dawson ................ | A61F 2/4601 |
| 2017/0239059 A1 | 8/2017 | Boublil et al. | |

FOREIGN PATENT DOCUMENTS

| | | |
|---|---|---|
| WO | 2014/068259 A1 | 5/2014 |
| WO | 2016/027025 A2 | 2/2016 |
| WO | 2016/177790 A1 | 11/2016 |

OTHER PUBLICATIONS

International Search Report and Written Opinion of the International Searching Authority of PCT/US2017/030701, dated Aug. 3, 2017.

International Search Report and Written Opinion of the International Searching Authority of PCT/US2017/044740, dated Nov. 17, 2017.

International Search Report and Written Opinion of the International Searching Authority of PCT/US2015/052121, dated Nov. 19, 2015.

* cited by examiner

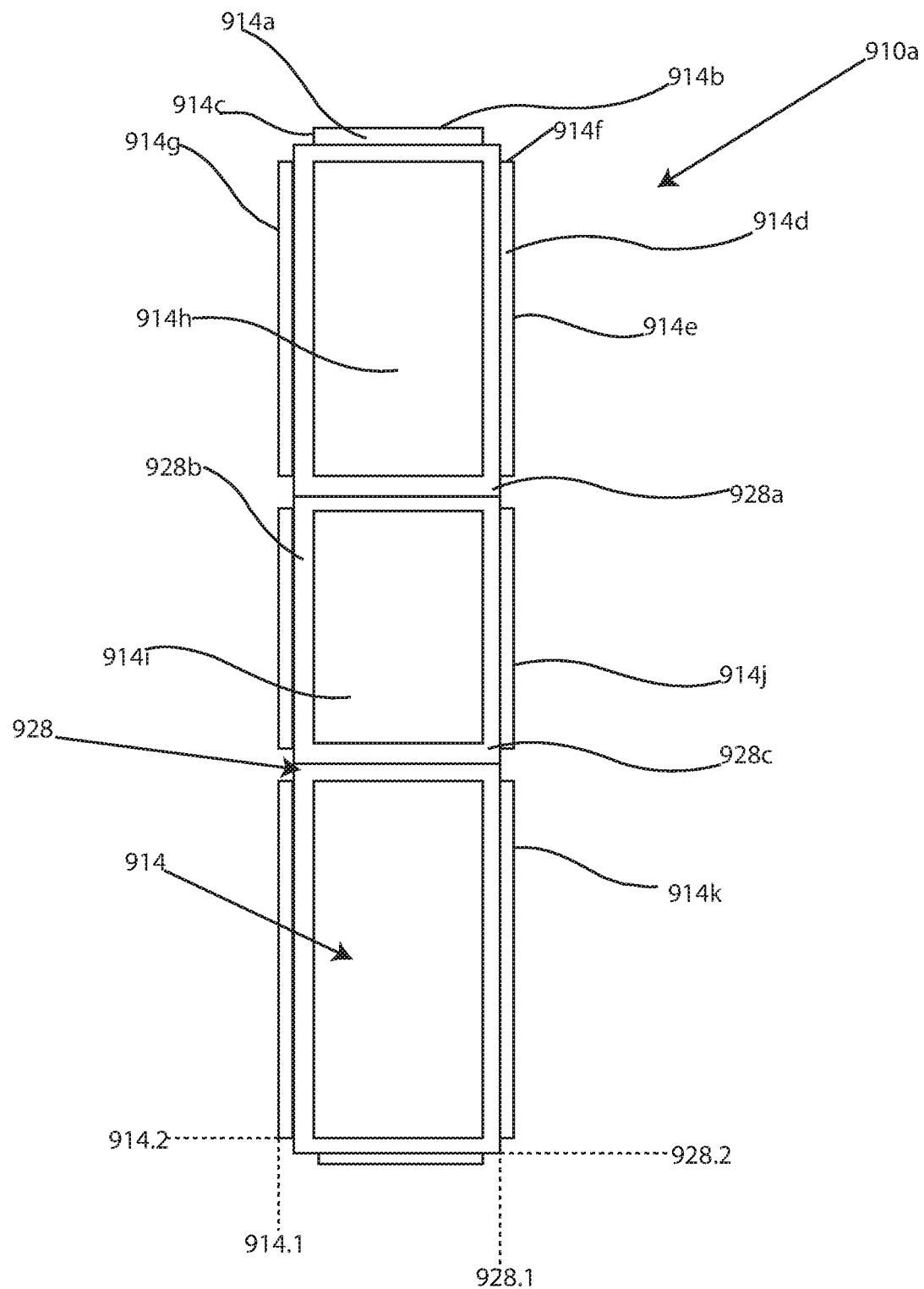

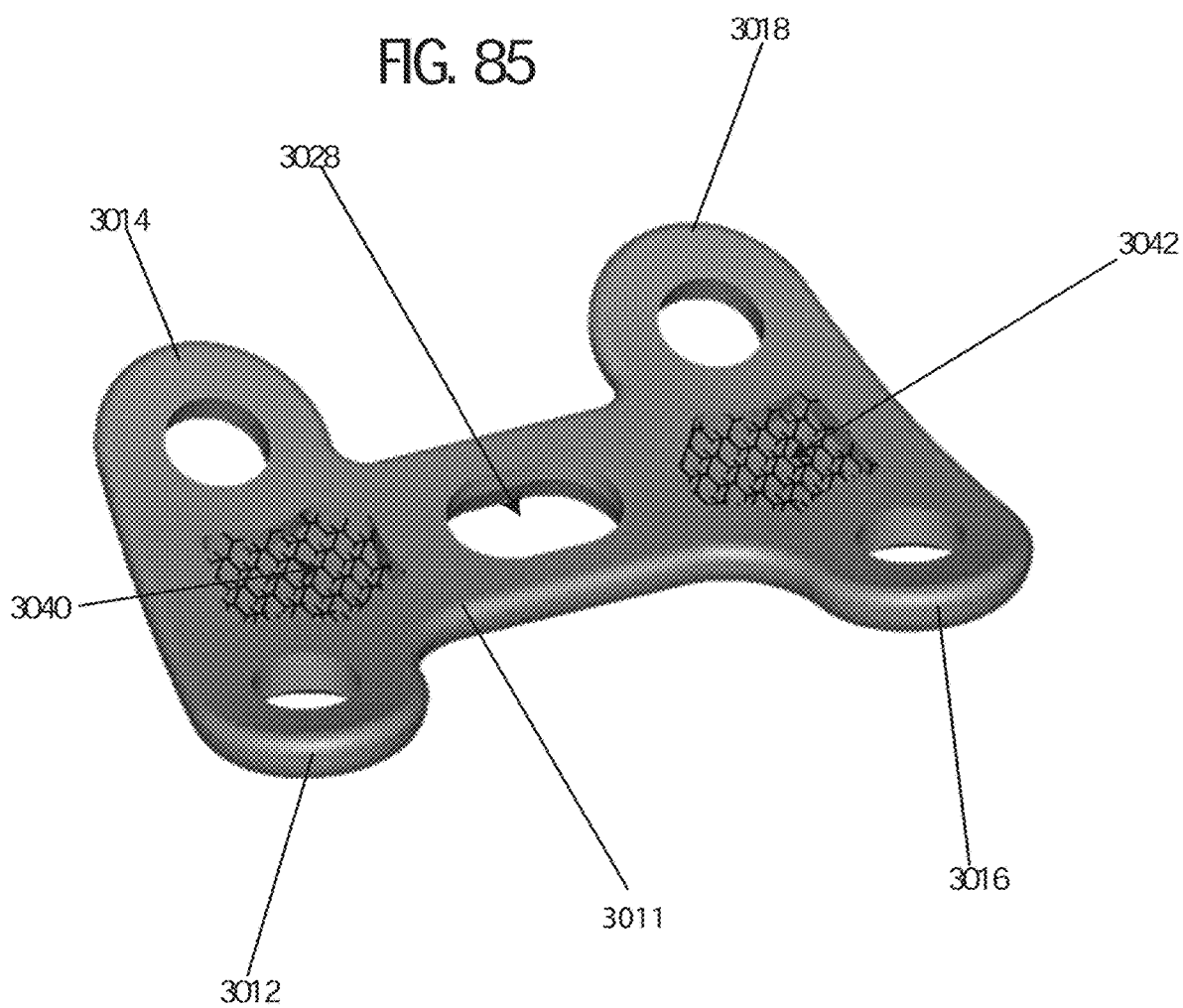

FIG. 86A
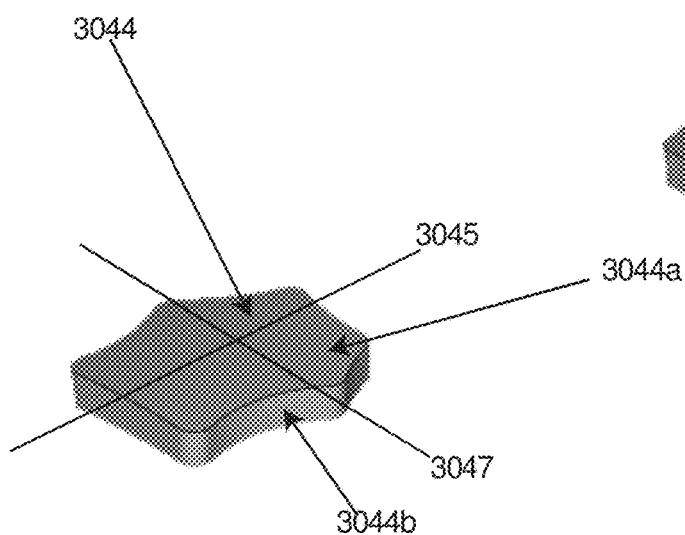
FIG. 86B
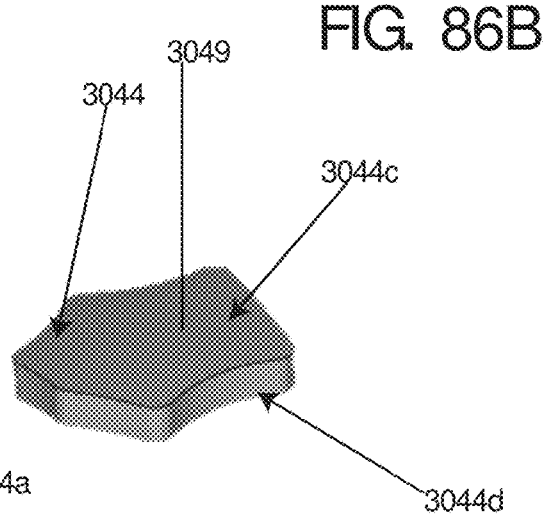
FIG. 86C
FIG. 86D
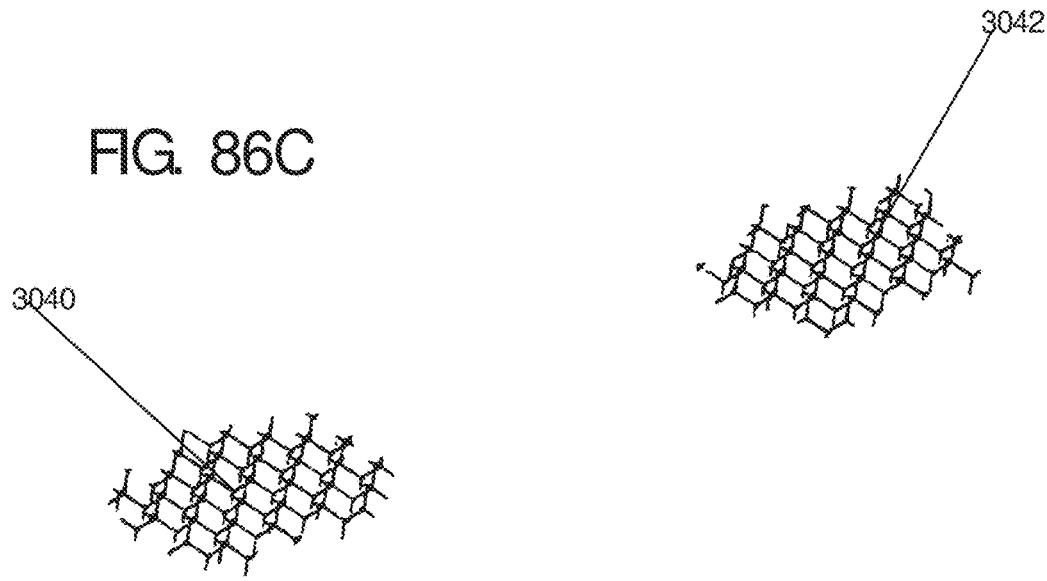

3040, 3042

BONE FIXATION DEVICES

CROSS REFERENCE TO RELATED APPLICATIONS

This application is a non-provisional application that hereby claims priority from provisional application Ser. No. 62/345,536 filed on Jun. 3, 2016, provisional application Ser. No. 62/404,923 filed on Oct. 6, 2016 and provisional application Ser. No. 62/425,363 filed on Nov. 22, 2016 the disclosures of which are hereby incorporated herein by reference in their entirety.

FIELD OF THE INVENTION

The present invention relates generally to constructs for osteotomies. More specifically, but not exclusively, the present invention concerns osteotomy wedges that promote osteosynthesis and/or bone fusion.

BACKGROUND OF THE INVENTION

Osteotomies are surgical procedures that attempt to correct deformities in a patient's skeletal system. Some indications may include spinal fusion surgery, large bone correction such as tibial plateau osteotomies, extremities including foot and ankle and upper extremity, as well as craniomaxiofacial surgical corrections. The goal of the surgical correction may be to improve alignment, restore length and/or reduce pain while promoting osteosynthesis, or bone fusion. For the foot and ankle, some indications may include subtalar fusion, cotton, lapidus, calcanialcubiod, evans, and triple arthrodesis.

Osteotomies are common surgical procedures to correct deformities. As an example, flat foot surgery is an indication whereby an osteotomy may be utilized to correct the anatomical position of the foot. One current flat foot correction method is to use multiple products or devices for the osteotomy, such as a stand along bone wedge in combination with a separate plate, with or without compressive means. The bone wedge is typically made from a metal or bone (with the bone typically being either allograft or autograft). Once a bone cut is made, the bone wedge is typically inserted in the osteotomy site and temporarily held in place, such as with a temporary fixation pin. A plate is then commonly implanted across the osteotomy site in order to fixate the bones and, potentially, provide compression, to bring the bone faces into contact with the bone wedge. A risk of this approach, however, is that the bone wedge may shift or become dislodged during the process of applying compression across the fusion site. Further, the use of multiple distinct products or devices can have a negative impact on the surgical outcome, as well as increase the cost and complexity of the procedure.

Thus, a need exists for need for new and improved bone fixation devices that simplify the osteosynthesis surgical technique and provide an improved environment for osteosynthesis to occur. There also therefore exists a need for new and improved bone fixation devices that reduce the number of required products or devices and associated costs for osteosynthesis and/or bone fusions.

SUMMARY OF THE INVENTION

Aspects of the present disclosure provide orthopedic devices or implants to fixate an osteotomy site between two bone segments while promoting osteosynthesis in and around the implant.

The devices of the present disclosure may form a single construct including a bone plate segment and bone wedge segment. The bone wedge segment, and potentially the bone plate segment, may be implanted into an osteotomy site between two bone segments to fix the bone segment and promote osteosynthesis in and around at least the wedge segment. The plate segment and the wedge segment may include at least one aperture extending therethrough for fixation of the device to at least one of the bone segments. At least the wedge segment of the device may include a porous architecture that encourages or allows bone to grow into it and around it on both sides of the osteotomy site, thereby promoting osteosynthesis on both sides of the osteotomy site. The porous architecture can be of different shapes or variable shaped. In addition, the porous architecture can be either substantially smooth or substantially rough in surface.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the present disclosure and together with the detailed description herein, serve to explain the principles of the present disclosure. The drawings are only for purposes of illustrating some embodiments and are not to be construed as limiting the present disclosure. It is emphasized that, in accordance with the standard practice in the industry, various features may not be drawn to scale. The foregoing and other objects, features and advantages of the present disclosure are apparent from the following detailed description taken in conjunction with the accompanying drawings in:

FIG. 35A is a side view of another embodiment of the wedge portion;

FIG. 85 is an underside view of the bone fixation device;

FIG. 86A shows a perspective view of the mesh insert;

FIG. 86B shows a perspective view of a set of larger openings for the mesh segment;

FIG. 86C is a perspective view of a mesh section;

FIG. 86D is a perspective view of another mesh section;

DETAILED DESCRIPTION FOR CARRYING OUT THE INVENTION

Figure 1:
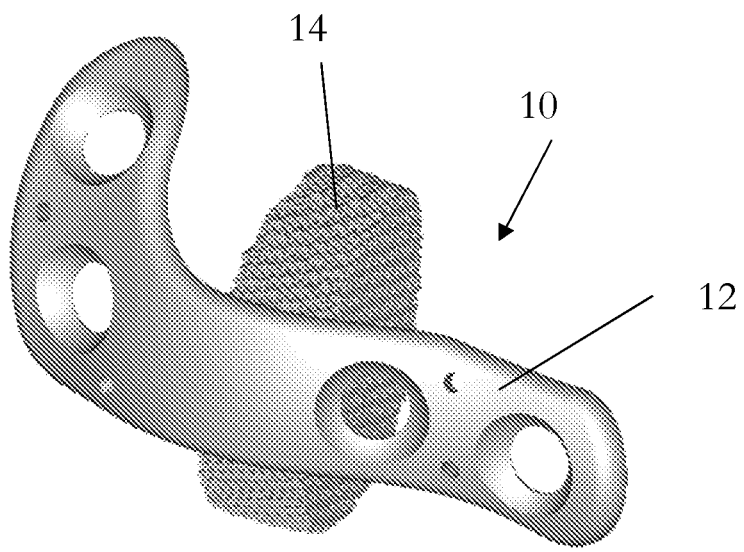
FIG. 1 is a top perspective view of a bone fixation and osteosynthesis device.

Generally stated, disclosed herein are a number of embodiments of bone fixation devices. The terms "bone fixation device," "bone fixation implant," "osteotomy or osteosynthesis device," "fusion device," "device," and "implant" may be used interchangeably as they are utilized herein synonymously. Further, surgical methods for using the bone fixation devices are discussed.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. In addition, for the purposes of this disclosure when referencing the device, the term "proximal" will mean the portion of the device closest or nearest the insertion instrument. The term "distal" shall mean the portion of the device farthest away from the insertion instrument. The terms osteosynthesis, osteotomy and the like are used herein to refer to the promotion of bone formation/growth and bone in-growth, as explained further below.

Referring to the drawings, wherein like reference numerals are used to indicate like or analogous components throughout the several views, and with particular reference to FIGS. 1-6, there is illustrated a bone fixation and/or osteosynthesis device or implant 10. The device 10 may be configured to attach to adjacent bone segments where bone has been removed from at least one of the bone segments for the purposes of fusing the bones segments together (i.e., an osteotomy site). The device 10 may also be configured to correct a bone length discrepancy or issue, such as in the cases of a failed arthroplasty procedures.

Figure 2:
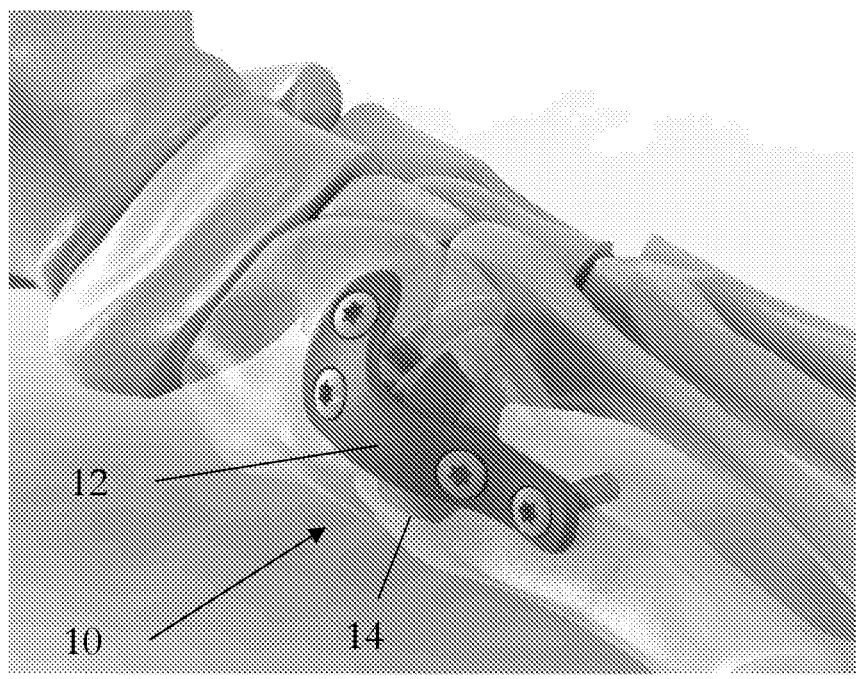
FIG. 2 is a view of the device of FIG. 1 shown coupled to a bone.
Figure 3:
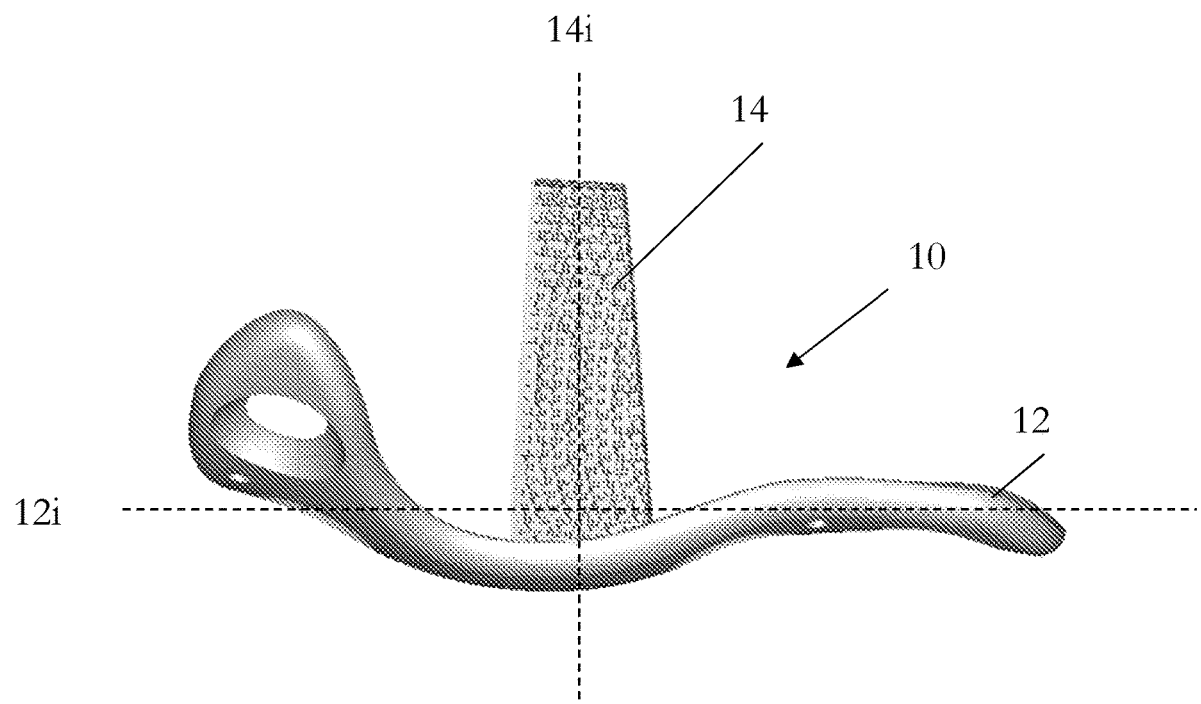
FIG. 3 is a side view of a bone fixation and osteosynthesis device.
Figure 4:
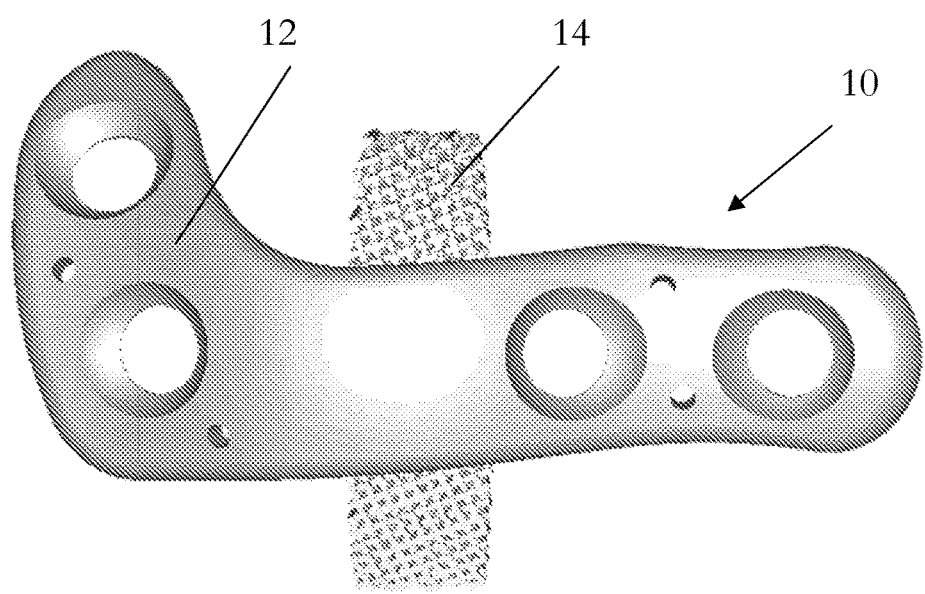
FIG. 4 is a top view of a bone fixation and osteosynthesis device.
Figure 5:
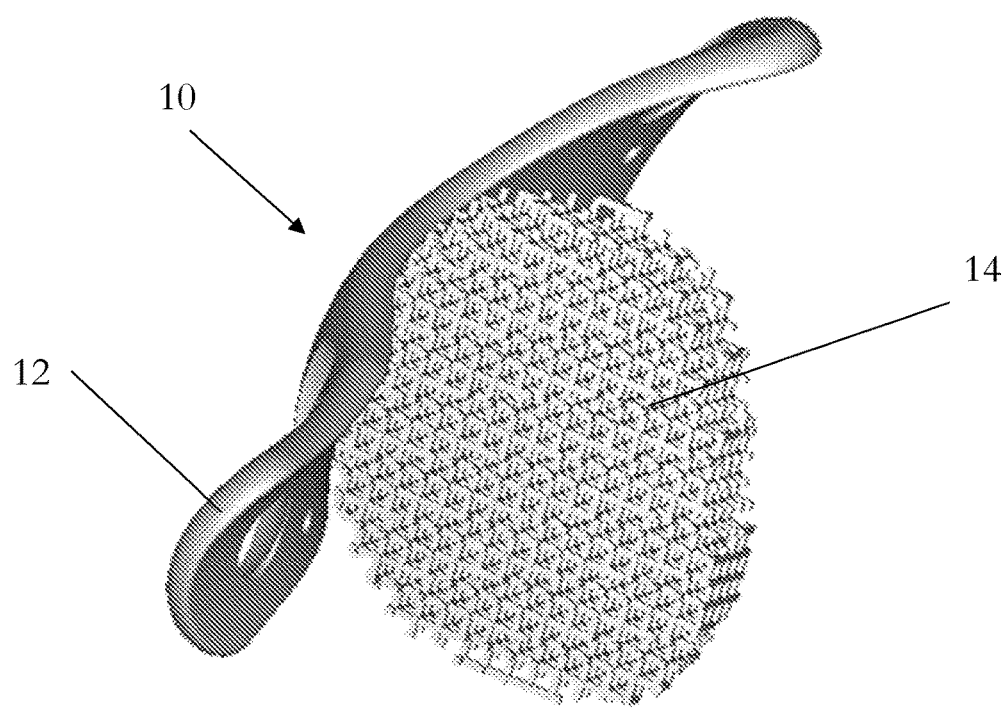
FIG. 5 is a bottom perspective view of the bone fixation and osteosynthesis device.

As shown in FIGS. 1-6, the device 10 may be a single construct including a bone plate segment or portion 12 and bone wedge segment or portion 14. The bone plate segment 12 and the bone wedge segment 14 may be integral or of one-piece construction. The bone plate segment 12 and/or the bone wedge segment 14 may be made from a medical grade material, such as titanium (or other metal material), polymer or PEEK composite, for example. The bone plate segment 12 and/or bone wedge segment 14 may be made from any manufacturing process or technique. In some embodiments, the bone plate segment 12 and the bone wedge segment 14 may be mechanically made in the same manufacturing process, by the same material, at relatively the same time. For example, the bone plate segment 12 and/or the bone wedge segment 14 may be made, for example, from an additive manufacturing process (e.g., a 3-D printing process or laser-sintering) in a layer by layer manner. As shown in FIGS. 1 and 5 the bone wedge segment 14 has in this embodiment a substantially circular cross-sectional face which extends substantially perpendicular to the extension of the bone plate segment 12. In addition, as shown in FIG. 3 the bone wedge segment 14 has a tapered profile with one surface closer to the bone plate segment 12 being thicker or extending in a longer dimension along the bone plate segment axis 12i (See FIG. 3) than the opposite end. While this shape is shown multiple different shapes for each of the bone plate segment 12 and the bone wedge segment 14 may be used.

As shown in FIGS. 1-6, the bone plate segment 12 may define an L-shape or similar shape and include fixation apertures. However, the bone plate segment 12 may define any shape and may or may not include fixation apertures. The bone plate segment 12 may be substantially solid (but for the fixation apertures, for example). In some embodiments, the bone plate segment 12 may include a substantially smooth outer surface, such as a polished outer surface. For example, the at least one of the dorsal or plantar outer surface (or both) of the bone plate segment 12 may be substantially smooth. Alternatively, the bone plate segment 12 may have a roughened surface as well to facilitate interactions with other materials.

As shown in FIGS. 1-6, the bone plate segment 12 may include a plurality of fixation apertures extending therethrough. The bone plate segment 12 may include distal and proximal fixation apertures. The fixation apertures may be configured for a bone fixation member, such as a bone screw, nail, k-wire, etc., to extend through the bone plate segment 12 and into a first or second bone segment forming an osteotomy site. In some embodiments, the bone plate segment 12 may include at least one compression slot that is configured to be utilized with a corresponding fixation aperture such that the construct provides compression of the osteotomy site applied at the faces of the bones and the engagement surfaces of the wedge portion 14, as described below. If provided, the fixation apertures may include a countersink such that a head of a fixation member extending therethrough is positioned at or below the outer surface of the bone plate segment 12, as shown in FIGS. 1-6. The fixation apertures may be threaded or non-threaded, or include an alternative internal mechanical locking or engagement mechanism.

Figure 6:
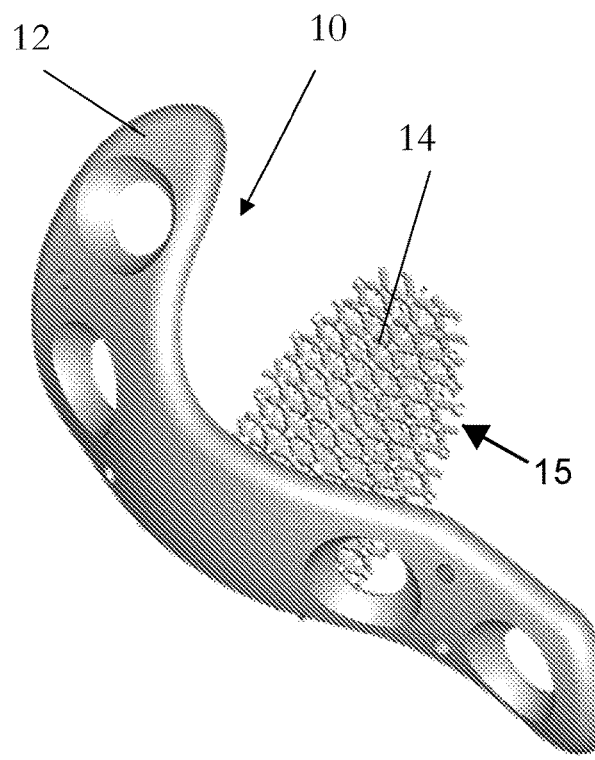
FIG. 6 is a top perspective view of a bone fixation and osteosynthesis device.

The bone wedge segment 14 may protrude from the bone plate segment 12 and define a free end so at to extend into a fusion and/or osteotomy site, as shown in FIGS. 1-6. For example, the bone wedge segment 14 may extend from the dorsal side or surface of the bone plate segment 12. The bone wedge segment 14 may extend from the bone plate segment 12 perpendicularly or at an angle such as substantially perpendicular to the extension of the bone plate segment 12. This is shown by way of example in FIG. 3 by the longitudinal axis 12i of the bone plate segment 12 and the substantially perpendicular extension of the bone wedge segment 14 via axis 14i. The bone wedge segment 14 may be located between a proximal end and a distal end of the bone plate segment 12. As shown in FIGS. 1-6, the wedge segment 14 may include a porous architecture, lattice or matrix that is configured to allow, promote or encourage bone to grow into it and around it. Conversely, the bone plate segment 12 may be substantially solid or non-porous such that bone ingrowth is prevented (See FIG. 7). In other embodiments, at least a portion of the bone plate segment 12 may be porous or roughened. For all of these embodiments the porous architecture can be of a variable architecture, or of a substantially consistent pattern. In addition the porous architecture can be of any suitable pattern for each of the cells such as substantially square, diamond, honeycomb or any other suitable pattern. In addition, for any of these embodiments disclosed herein the porous architecture can be substantially smooth or smooth and/or rough or substantially rough. A roughened surface 15 of the bone wedge segment 14 can be used for example to promote interactions with other adjacent bones to promote a fusion of the porous architecture of the bone wedge segment 14 with an adjacent bone, as shown in FIG. 6. As explained further below, the wedge segment 14 may be configured to be positioned between two bone segments at a fusion site, such as at an osteotomy site (e.g., a fracture site), with the bone plate segment 12 positioned exterior to the site and in abutment with the faces of the bone segments. The porous architecture of the wedge segment 14 may thereby promote osteosynthesis (e.g., bone formation and ingrowth) on both sides of the site. The wedge segment may have a varying porosity profile such as that outlined below.

The porous architecture of the wedge segment 14 may be any architecture that provides openings or spaces at least in the engagement or exterior surfaces of the wedge segment 14 that contact the bone segments. The openings or spaces in the exterior surfaces of the wedge segment 14 may be in communication with internal openings or voids within the construct of the wedge segment 14 such that bone is able to grow and penetrate into and within the wedge segment 14. In some embodiments, the bone wedge segment 14 may include a porosity, in the horizontal and/or vertical direction (e.g., along the proximal-distal and/or medial-lateral and/or palmar-dorsal directions) within the range of about 60% to about 90%, or within the range of about 65% to about 85%, or within the range of about 70% to about 80%. The porous architecture of the bone wedge segment 14 may be a defined or uniform architecture or pattern, may be a randomly generated or distributed architecture or lattice, or may include a different architecture in differing portions of the wedge segment 14. The porous architecture which may include individual struts or elongated portions may be smooth, substantially smooth, roughened or substantially roughenened. As shown in FIGS. 1-6, the wedge segment 14 may be entirely comprised of the porous architecture or lattice. Stated differently, the porous architecture or lattice may make-up or form the wedge segment 14. As shown in FIGS. 1-6, the wedge segment 14 includes a substantially uniform pattern of unit cells (e.g., substantially cubic or quadrilateral lattice structure). In some embodiments, the porous architecture of the wedge segment 14 may be formed of a structure of about 1 mm unit cells. In some embodiments, the porous architecture of the wedge segment 14 may be formed of interconnected elongate strut members. For example, in some embodiments the porous architecture of the wedge segment 14 may be formed, for example, of diamond cut interconnected elongate strut members with a diameter within the range of about 0.1 mm to about 0.5 mm, or within the range of about 0.2 mm to about 0.4 mm, or about 0.3 mm. The porous architecture of the wedge segment 14 may be formed via diamond cutting (or a similar process) the structure and/or diamond cutting (or a similar process) struts or other members that are utilized to form the architecture. While a diamond pattern for the porous cells of the wedge segment may be used. A honeycomb pattern may also be used.

The size and/or shape of the bone wedge segment 14 may be formed to correspond to the size and/or shape of the cross section of the bones at the fusion or osteotomy site, thereby providing an optimal environment for bone ingrowth to occur. For example, as shown in the FIGS. 1-6 the wedge segment 14 may define an oval or circular disc shape that extends from a dorsal-facing surface of the bone plate segment 12. In some embodiments, the wedge segment 14 may taper in thickness at it extends from the bone plate segment 12, as shown in the FIGS. 1-6. For example, the wedge segment 14 may include engagement surfaces for engaging the at least two bone segments forming the fusion or osteotomy site, and at least one of the engagement surfaces may be angled or otherwise extend toward the other of the engagement surfaces such that the thickness of the wedge segment 14 tapers at it extends from the bone plate segment 12, as shown in the FIGS. 1-6. The engagement surfaces of the wedge segment 14 may be planar, curved, convex or concave. The shape and/or size of the wedge segment 14 may be configured for maximum bone contact and anatomical correction based on the location of the fusion or osteotomy site, a particular patient, and/or a particular surgical need. In the illustrated embodiment shown in FIGS. 1-6, the disc shaped bone plate segment 12 includes planar engagement surfaces with one of the engagement surfaces angled toward the other as they extend from the bone plate portion 12.

In use, as shown in FIG. 2, the bone plate segment 12 of the device 10 may be fixed to the exterior of the bone segments forming a fusion and/or osteotomy site by one or more bone fixation members, such as via bone screws extending through the fixation apertures of the bone plate segment 12. As also shown in FIG. 2, the bone wedge segment 14 may extend from the bone plate segment 12 and into the site between the two bone segments. The porous architecture of the wedge segment 14, such as at least a porous architecture at the engagement surfaces of the wedge segment 14 that abut or engage the bone segments, may promote osteosynthesis (e.g., bone formation and ingrowth). The wedge segment 14 may thereby promote osteosynthesis osteosynthesis (e.g., bone formation and ingrowth) in and around the wedge segment 14 on both sides of the site. As noted above, the plate segment 12 and/or the bone fixation members may apply a compressive force across the site to further promote osteosynthesis and fusion osteosynthesis (e.g., bone formation and ingrowth).

Figure 7:
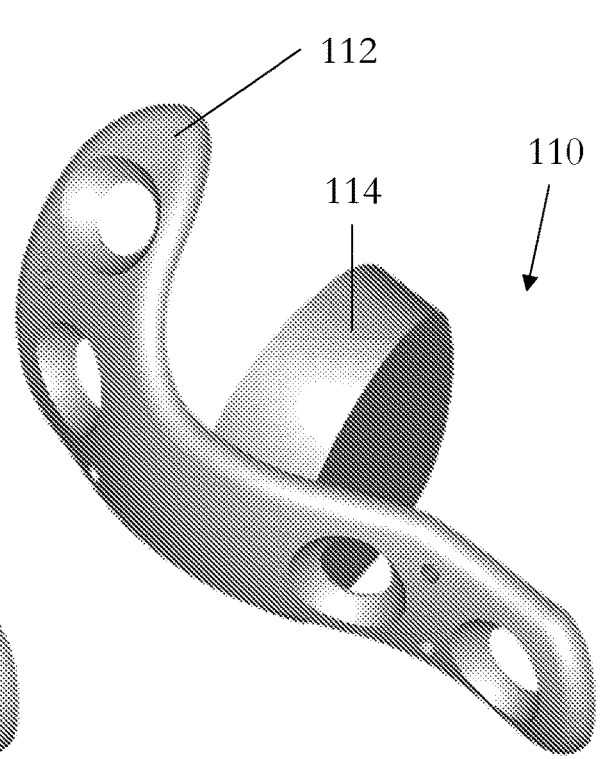
FIG. 7 illustrates another bone fixation and osteosynthesis device according to the present disclosure.

In FIG. 7, another bone fixation and osteosynthesis device is indicated generally by the reference numeral 110. The bone fixation and osteosynthesis device 110 is similar to the bone fixation and osteosynthesis device 10 described above with reference to FIGS. 1-6, and therefore like reference numerals preceded by the numeral "1" are used to indicate like aspects. One difference between the device 110 and device 10 is the porous architecture or nature of the bone wedge segment 114. As shown in FIGS. 6 and 7, for example, the bone wedge segment 114 of device 110 has a denser or finer porous architecture than that of the bone wedge segment 14 of device 10. As discussed above, the porous architecture or nature of the wedge segment 114 may vary and may be any porous architecture that allows for bone ingrowth to promote osteosynthesis in and around the wedge segment 114 on both sides of the fusion site. As discussed above, however, the porous architecture may be in a substantially uniform or consistent pattern or a variable pattern, with at least one pattern being at least one of honeycomb, diamond, square or any other suitable shape for each cell. In addition, the porosity of these patterns could be consistent or variable depending on the need. Furthermore, the individual parts of the porous architecture, that of the individual struts may be either smooth, substantially smooth, roughened or substantially roughened.

Figure 8:
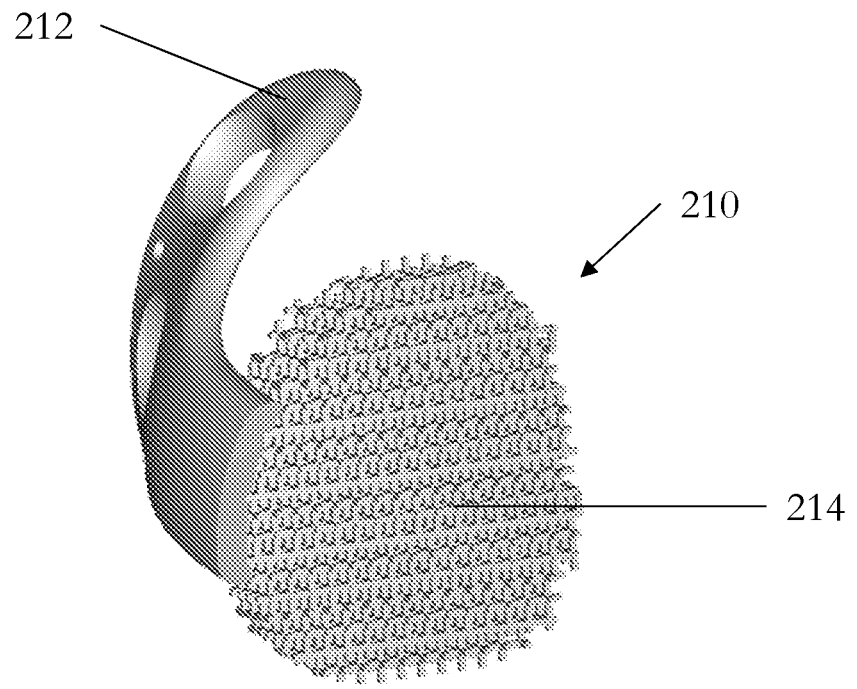
FIG. 8 is a side cross-sectional view of a bone fixation and osteosynthesis device of FIG. 7.
Figure 9:
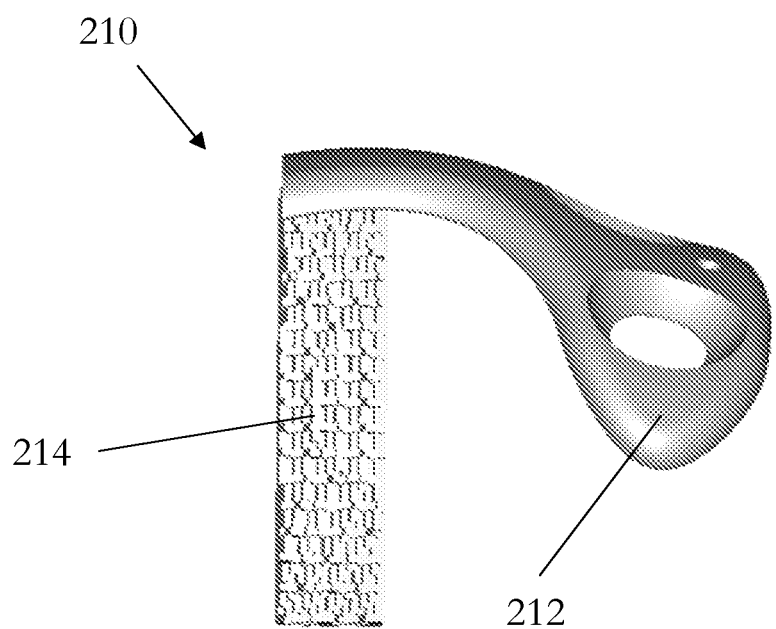
FIG. 9 illustrates another bone fixation and osteosynthesis device according to the present disclosure.

In FIGS. 8 and 9, another bone fixation and osteosynthesis device is indicated generally by the reference numeral 210. The bone fixation and osteosynthesis device 210 is similar to the bone fixation and osteosynthesis device 10 of FIGS. 1-6 and the bone fixation and osteosynthesis device 110 of FIG. 7, and therefore like reference numerals preceded by the numeral "2" are used to indicate like aspects. One difference between the device 210 and devices 10 and 110 is the configuration of the bone wedge segment 214. As shown in FIG. 9, the wedge segment 214 does not taper in thickness as it extends from the plate segment 112. As shown in FIGS. 8 and 9, the engagement surfaces of the wedge segment 214 (the surfaces that engage the end surfaces of the at least two bone segments) are substantially planar and are oriented substantially parallel to each other. Also, the wedge segment 214 (and the engagement surfaces thereof) is substantially elliptical or oval.

Figure 10:
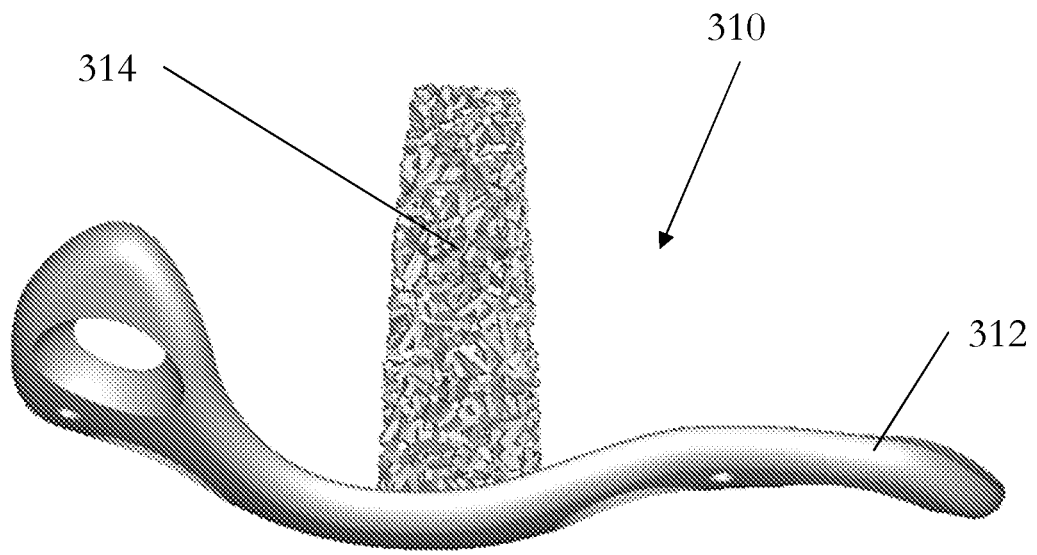
FIG. 10 illustrates a side view of another bone fixation and osteosynthesis device according to the present disclosure.
Figure 11:
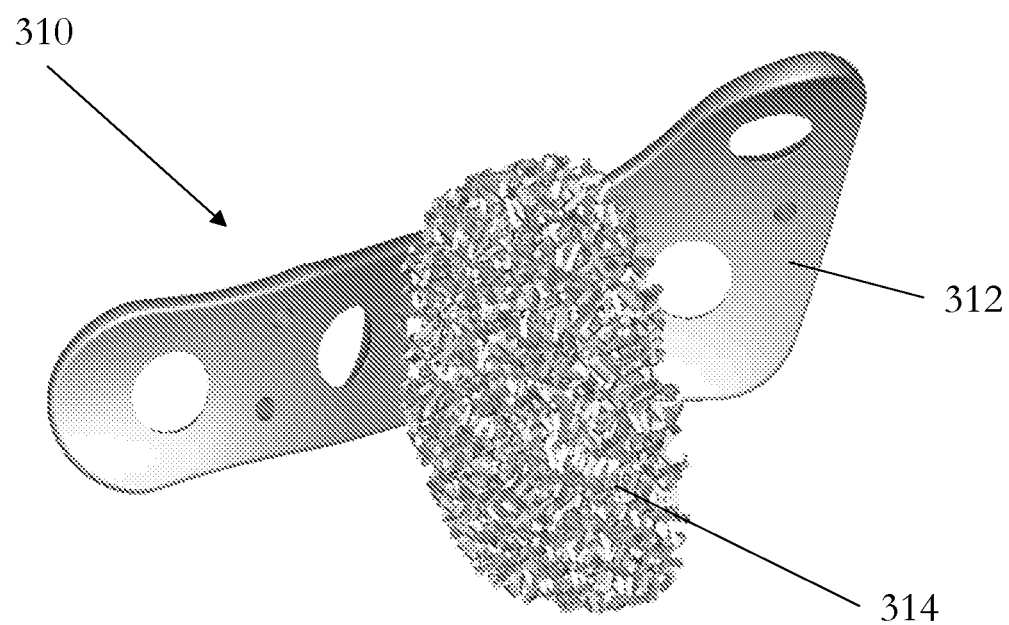
FIG. 11 is a bottom perspective view of another bone fixation and osteosynthesis device as in FIG. 11.

In FIGS. 10 and 11, another bone fixation and osteosynthesis device is indicated generally by the reference numeral 310. The bone fixation and osteosynthesis device 310 is similar to the bone fixation and osteosynthesis devices 10, 110 and 210, and therefore like reference numerals preceded by the numeral "3" are used to indicate like aspects. One difference between the device 310 and devices 10, 110 and 210 is the configuration of the bone wedge segment 314. As shown in FIG. 10, the wedge segment 314 tapers in thickness between the engagement surfaces thereof as it extends from the plate segment 312. As shown in FIG. 10, the engagement surfaces of the wedge segment 314 (the surfaces that engage the end surfaces of the at least two bone segments) are substantially planar and both taper towards the other as they extend away from the plate segment 312. In this way, the cross section of the wedge segment 314 along the medial-lateral direction forms, for example, an isosceles-type trapezoidal shape (or other polygonal shape). In some embodiments, the wedge segment 314 may taper within the range of about 1 degrees and about 50 degrees from the plate segment 312, or within the range of about 5 degrees and about 25 degrees from the plate segment 312.

As shown in FIGS. 10 and 11, the wedge segment 314 includes a lattice formed of strut members that are specific and organized. The strut members are interconnected to form the porous architecture for bone ingrowth. However, as noted above, the porous architecture of the bone wedge segment 314 may be a randomly generated or a non-uniform architecture or pattern.

Figures 12, 13:
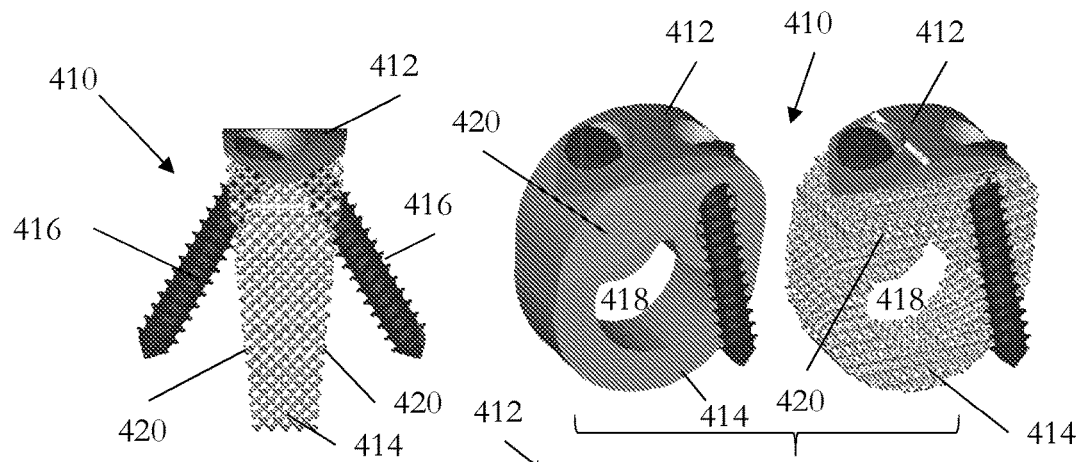
FIG. 12 is a side view of illustrate another bone fixation and osteosynthesis device according to the present disclosure.
FIG. 13 show a top perspective view of another bone fixation and osteosynthesis device.
Figure 14:
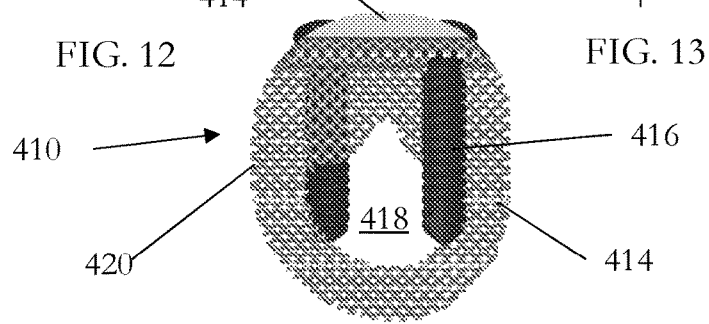
FIG. 14 is an end view of another bone fixation and osteosynthesis device.

In FIGS. 12-14, another bone fixation and osteosynthesis device is indicated generally by the reference numeral 410. The bone fixation and osteosynthesis device 410 is similar to the bone fixation and osteosynthesis devices 10, 110, 210 and 310, and therefore like reference numerals preceded by the numeral "4" are used to indicate like aspects. One difference between the device 410 and devices 10, 110, 210 and 310 is the configuration of the bone plate segment 412 and the fixation apertures/fixation members 416. As shown in FIGS. 12-14, the bone plate segment 412 extends only along the top surface of the bone wedge segment 414. The bone plate segment 412 is thereby not larger than the top surface of the bone wedge segment 414, and is contoured and shaped so that the device 414, as a whole, matches or corresponds to a particular and/or desired fusion/osteosynthesis site. In this way, the device 410 can be implanting into a fusion/osteosynthesis site and create a zero or non-existent profile above the surface of the patient's bone segments. As shown in FIGS. 12-14, the device 410, as a whole, may form a tapered disc shaped with the bone plate segment 412 positioned at one end and the bone wedge segment 414 extending therefrom and forming the disc-shaped porous engagement surfaces 420.

The fixation apertures, and thereby the corresponding fixation members 416 extending therethrough, of the bone plate segment 412 may also extend through a portion of the bone wedge segment 414, as shown on FIGS. 12-14. As shown FIGS. 12-14, the fixation apertures, and thereby the corresponding fixation members 416 extending therethrough, may be configured such that they extend through the plate segment 412 and through the portion of the wedge segment 414 extending from the plate segment 412 to one of the engagement surfaces 420. The fixation apertures may extend to a portion of the engagement surfaces 420 that is proximate to the bone plate segment 412 and distal to the free end of the wedge segment 414.

As also shown FIGS. 12-14, the device 410 may include at least one pair of fixation apertures, and thereby at least one pair of corresponding fixation members 416 extending therethrough. The pair of fixation apertures, and thereby the corresponding pair of fixation members 416 extending therethrough, may extend substantially perpendicular to engagement surfaces 420 with respect to the medial-lateral direction. The pair of fixation apertures, and thereby the corresponding pair fixation members 416 extending therethrough, may extend substantially parallel to one another along the medial-lateral direction. As shown FIGS. 12-14, for example, one aperture of the pair of fixation apertures (and thereby the corresponding fixation member 416 extending therethrough) may extend from the outer surface of the plate segment 412 to one of the engagement surfaces 420, and the other of the pair of fixation apertures (and thereby the corresponding fixation member 416 extending therethrough) may extend from the outer surface of the plate segment 412 to the other of the engagement surfaces 420. As noted above, the engagement surfaces 420 of the wedge segment 414 may substantially oppose each other. In some embodiments, the pair of fixation apertures (and thereby the corresponding fixation members 416 extending therethrough) may extend at an angle with respect to the corresponding engagement surface 420 (along the proximal-distal direction) within the range of about 15 degrees and about 35 degrees.

As shown FIGS. 13 and 14, the device 410 may include an inner or central aperture 418 extending through the wedge segment 414 between the engagement surfaces 420. As shown in FIG. 14, the inner aperture 418 may define a smaller area proximate to the fixation apertures than compared to the area proximate to the free end of the wedge segment 414. For example, the inner aperture 418 may define a mushroom-like or bulb-shape as shown, however inner aperture 418 may define a different shape. The inner aperture 418 may allow for bone growth through the device 410 along the proximal-distal direction, as well as to provide additional surface area of the porous architecture to facilitate the growth of bone over and into the wedge segment 414 to promote osteosynthesis. For example, the inner aperture 418 may allow for a surgeon to pack biologics into the interior of the wedge segment 414. The biologics may include, for example, at least one of bone chips, demineralized bone matrix (DBMs), other allografts, synthetics, or other biologics. As shown FIGS. 13 and 14, the porosity of the wedge segment 414 may be varied. This inner aperture such as inner aperture 418 which may be present in each of the embodiments of the wedges, can be used for a dual purpose, that of a place to receive a fastener, wherein the fastener is configured to secure a bone plate to a bone wedge, and also to receive biologic material to promote bone growth.

Figures 15, 16:
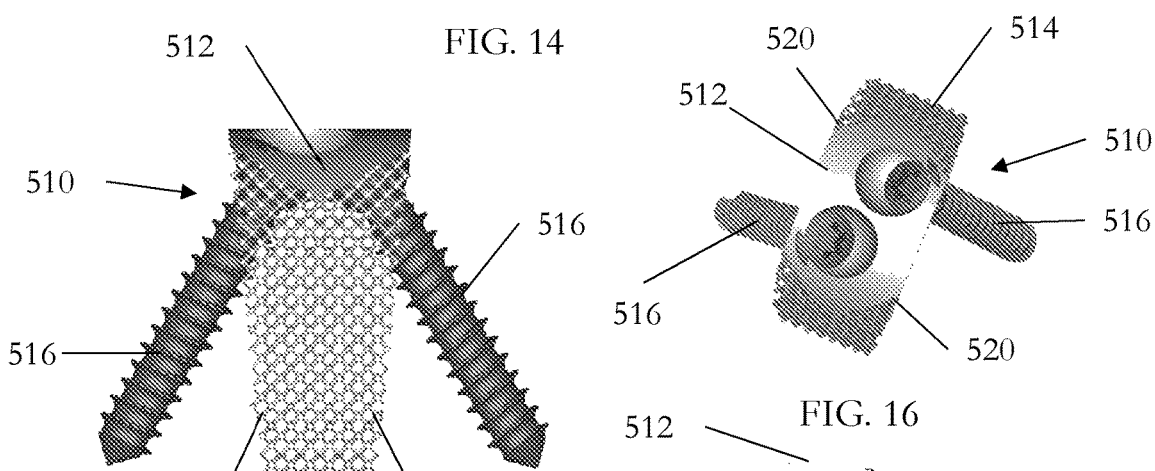
FIG. 15 is a side view of a bone fixation and osteosynthesis device.
FIG. 16 is a top view of a bone fixation and osteosynthesis device of FIG. 14.
Figure 17:
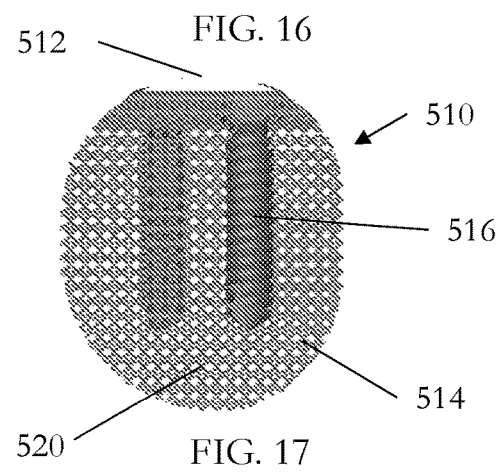
FIG. 17 is an end view of another bone fixation and osteosynthesis device according to the present disclosure.

In FIGS. 15-17, another bone fixation and osteosynthesis device is indicated generally by the reference numeral 510. The bone fixation and osteosynthesis device 510 is substantially similar to the bone fixation and osteosynthesis device 410, and therefore like reference numerals preceded by the numeral "5" are used to indicate like aspects. A difference between the device 510 and device 410 is the lack of the inner aperture 518 in the wedge segment 514. As shown in FIGS. 15-17, the porous architecture of the wedge segment 514 is continuous throughout the wedge segment 514. In this way, the engagement surfaces 520 are disc-shaped exterior surfaces defined by the porous architecture of the wedge segment 514. As discussed above, however, the porous architecture may be in a substantially uniform or consistent pattern or a variable pattern, with at least one pattern being at least one of honeycomb, diamond, square or any other suitable shape for each cell. In addition, the porosity of these patterns could be consistent or variable depending on the need. Furthermore, the individual parts of the porous architecture, that of the individual struts may be either smooth, substantially smooth, roughened or substantially roughened.

In FIGS. 18-21 another bone fixation and osteosynthesis device is indicated generally by the reference numeral 610. The bone fixation and osteosynthesis device 610 is similar to the bone fixation and osteosynthesis devices 10, 110, 210, 310, 410 and 510, and therefore like reference numerals preceded by the numeral "6" are used to indicate like aspects. One difference between the device 610 and devices 10, 110, 210, 310, 410 and 510 is the addition of an access aperture 622 extending from an exterior surface of the plate segment 612 to at least the wedge segment 614. The access aperture 622 may thereby be accessible after implementation. The access aperture 622 may be tapped (i.e., threaded) or otherwise configured to be removably coupled to a delivery device or instrument (not shown) with mating features. As explained further below, the access aperture 622 may be utilized to position biologics within the porous architecture of the wedge segment 614. This inner or access aperture such as inner aperture 622 which may be present in each of the embodiments of the wedges, can be used for a dual purpose, that of a place to receive a fastener, wherein the fastener is configured to secure a bone plate to a bone wedge, and also to receive biologic material to promote bone growth. In this embodiment, the inner aperture is not used to fasten the plate to the wedge but rather remains open for injection of biologics.

Figures 18, 19, 20:
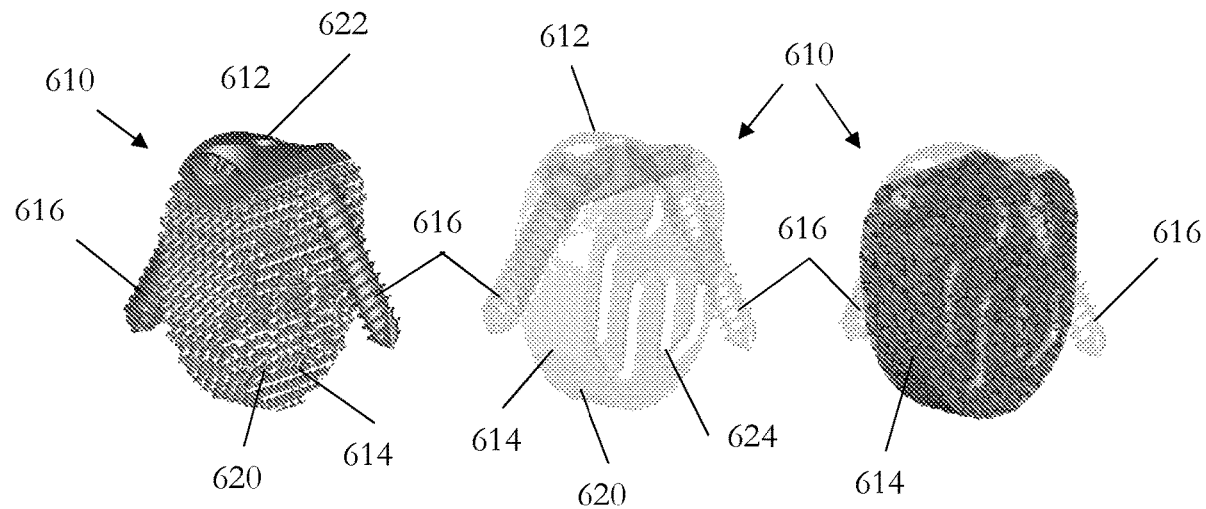
FIG. 18 is a top perspective view of another embodiment of a bone fixation device.
FIG. 19 is a side perspective view of the bone fixation device.
FIG. 20 is a side view of the bone fixation device of FIG. 18.
Figure 21:
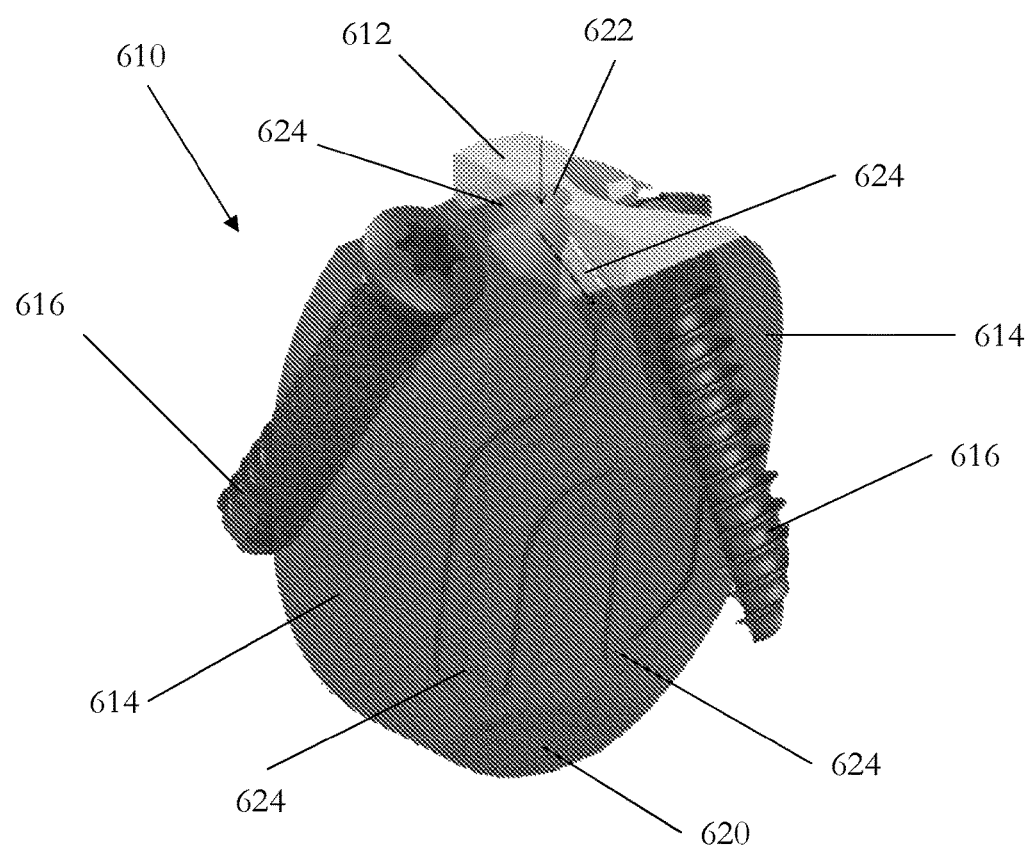
FIG. 21 is a side view of another embodiment of the bone fixation device of FIG. 18.

The wedge segment 614 may also include at least one interior channel 624 in communication with the access aperture 622 and extending through the porous architecture thereof, as shown in FIGS. 18-21. In the embodiment shown in FIGS. 18-21, the wedge segment 614 includes a pair of interior channels 624 extending from the access aperture 622 and through the porous architecture thereof. The at least one interior channel 624 of the wedge segment 614 may define any pathway or pattern as it extends through the wedge segment 614. In some embodiments, the at least one interior channel 624 may extend proximate to the engagement surfaces 620 and/or the outer surfaces or edges of the wedge segment 614 extending between the engagement surfaces 620. For example, the at least one interior channel 624 may extend proximate to the engagement faces 620 and along each portion, generally, of the engagement surfaces 620. In some embodiments, at least a portion of the at least one interior channel 624 may extend in a serpentine or similar manner The at least one interior channel 624 of the wedge segment 614 may allow for the addition or injection of biologics into the porous structure of the wedge segment 614. The biologics may aid in the osteosynthesis bone healing process, such as to promote bone growth into, through and over the wedge segment 614 on both sides of the site to achieve fusion. The biologics may be, for example, at least one of bone chips, demineralized bone matrix (DBMs), other allografts, synthetics, or other biologics. As the at least one interior channel 624 of the wedge segment 614 is in communication with the at least one access aperture 622, the access aperture 622 may be utilized (e.g., pre- and/or post-implantation) to introduce the biologics into the at least one interior channel 624, as indicated by the arrows in FIG. 21. As noted above, an instrument (not shown) may be removably coupled to the access aperture 622 and used to force, inject or otherwise introduce the biologics through the access aperture 622 and into and through the at least one interior channel 624. As shown in FIGS. 18-20, the porosity and/or pattern (e.g., pre-defined or randomized) of the porous architecture of the wedge segment 614 may vary while still providing the at least one interior channel 624 extending within the porous architecture. The at least one interior channel 624 of the wedge segment 614 may be formed by any means. The at least one interior channel 624 of the wedge segment 614 may be formed from the same process utilized to form the wedge segment 614 itself. For example, the porous architecture forming the wedge segment 614 may be produced via an additive manufacturing process (or another manufacturing process), and the at least one interior channel 624 may be voids formed within the porous architecture as the wedge segment 614 is formed.

Figure 22:
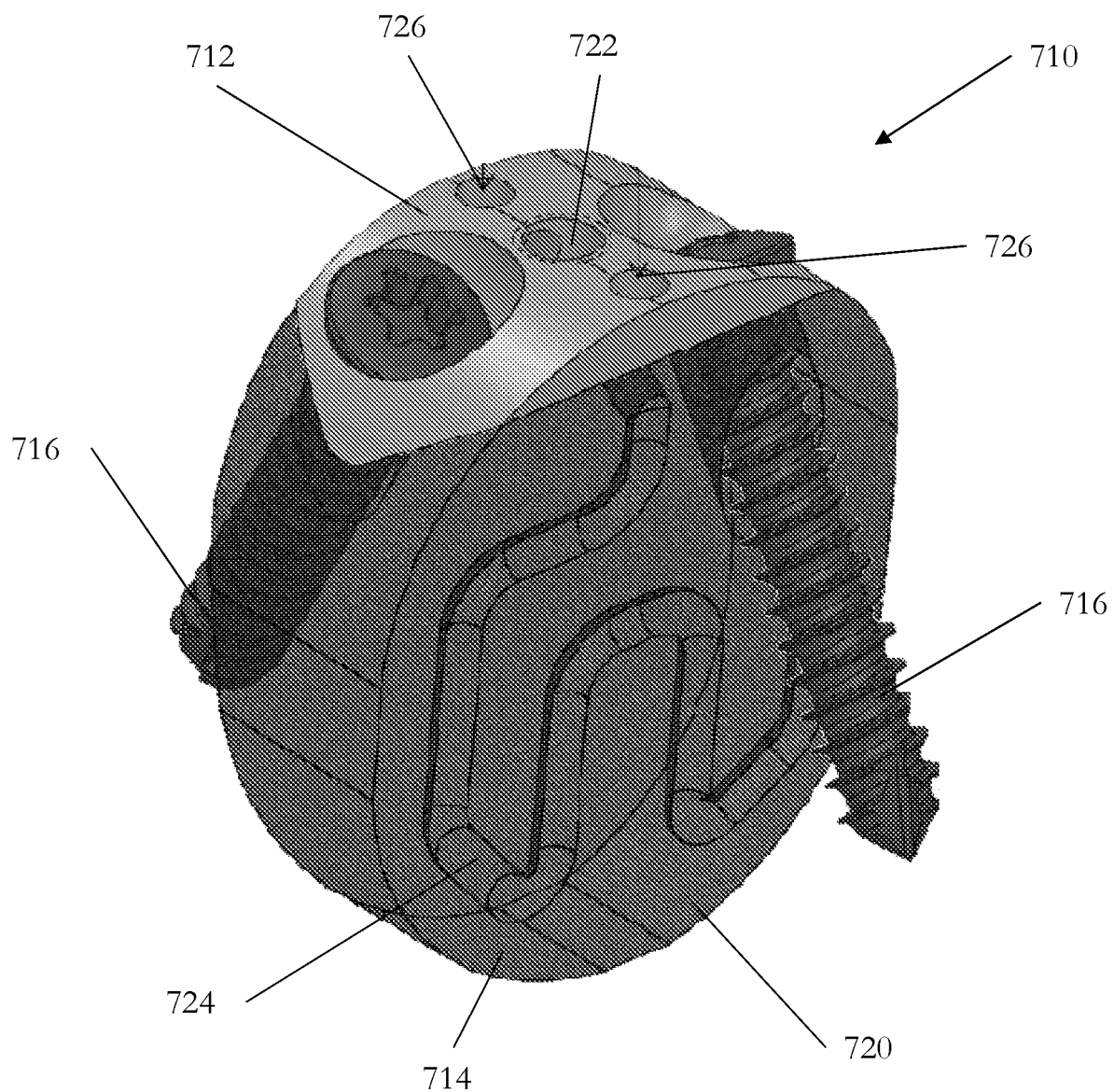
FIG. 22 is a side perspective view of another embodiment of the bone fixation device of FIG. 21.

In FIG. 22, another bone fixation and osteosynthesis device is indicated generally by the reference numeral 710. The bone fixation and osteosynthesis device 710 is substantially similar to the bone fixation and osteosynthesis device 610 of FIGS. 18-21, and therefore like reference numerals preceded by the numeral "7" are used to indicate like aspects. A difference between the device 710 and device 610 is the addition of at least one alternative access aperture 726. As shown in FIG. 22, the device 712 includes a pair of alternative access apertures 726. The pair of alternative access apertures 726 may be provided on opposing sides of the access aperture 722, such as on opposing sides of the access aperture 722 along the proximal-distal direction. The at least one alternative access aperture 726 may include substantially smooth side walls, and may therefore be void of threads.

Like the access aperture 722, the at least one alternative access aperture 726 may extend from an exterior surface of the plate portion 712 to the at least one interior channel 724 of the wedge segment 714. In some embodiments, each alternative access aperture 726 may extend to a corresponding interior channel 724, such as an interior channel 724 corresponding to each engagement surface 720. The at least one alternative access aperture 726 may extend directly from an exterior surface of the plate portion 712 to the at least one interior channel 724 of the wedge segment 714, or may extend to the at least one interior channel 724 via the at least one access aperture 722. The at least one alternative access aperture 726 may provide for an additional means of introducing biologics (pre- and/or post-implementation) into the interior of the porous architecture of the wedge portion 714 to promote bone fixation and osteosynthesis. The at least one alternative access aperture 726 may provide alternative access points for the introduction of the biologics into the interior channel 724 above the access aperture 722, for example. This inner or access aperture such as inner aperture 726 which may be present in each of the embodiments of the wedges, can be used for a dual purpose, that of a place to receive a fastener, wherein the fastener is configured to secure a bone plate to a bone wedge, and also to receive biologic material to promote bone growth. In this embodiment, the inner aperture is not used to fasten the plate to the wedge but rather remains open for injection of biologics.

Figure 23:
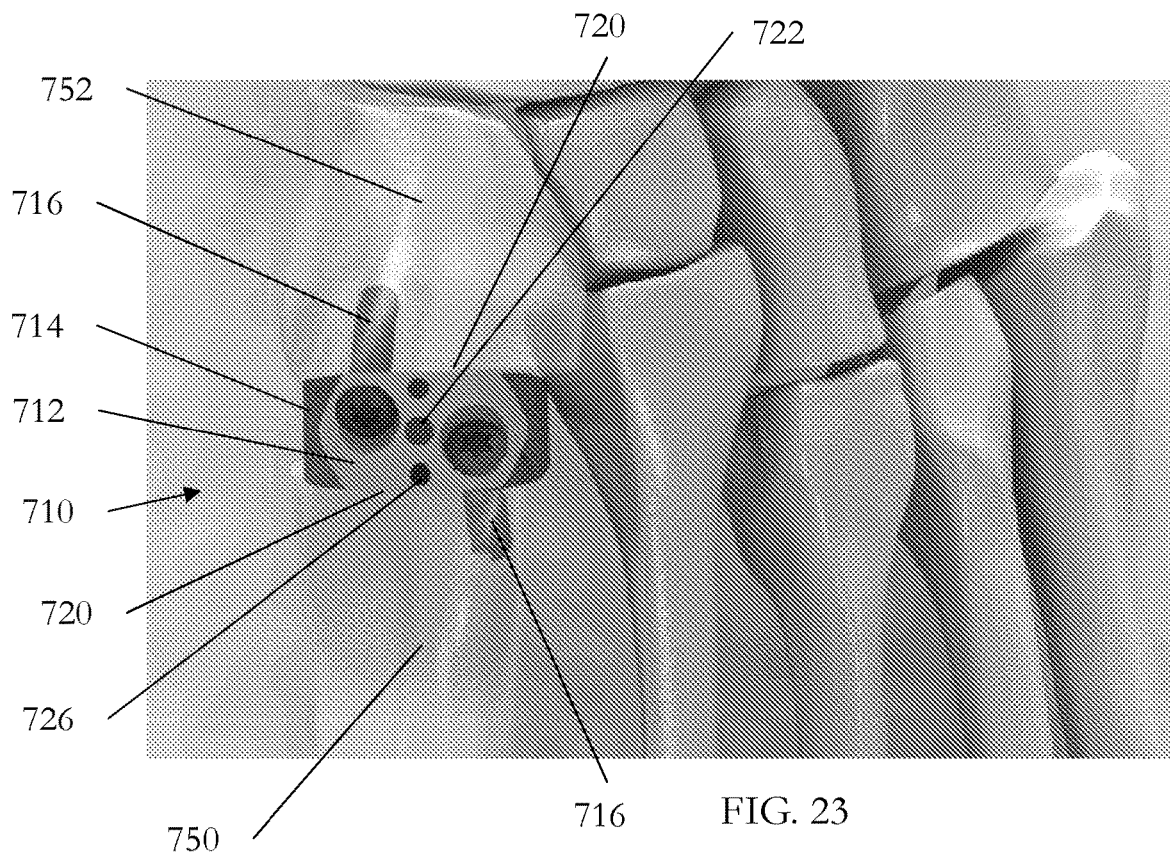
FIG. 23 illustrates the bone fixation and osteosynthesis device of FIG. 22 implanted in an osteotomy site.
Figure 24:
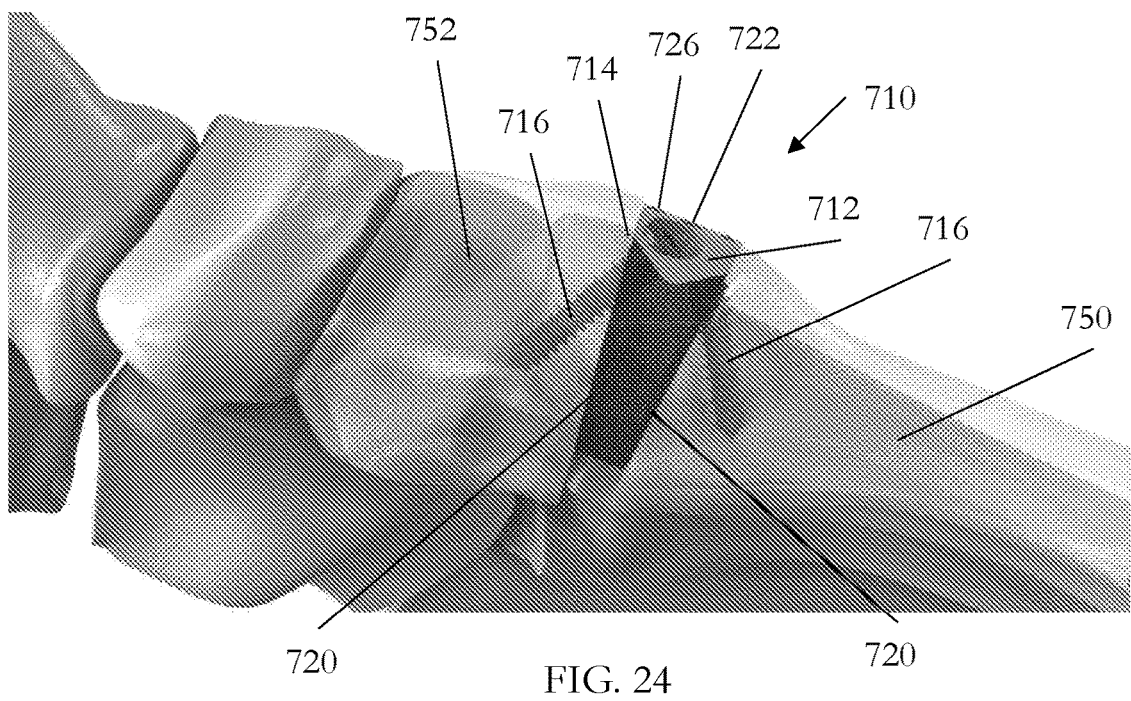
FIG. 24 illustrates the bone fixation device implanted in an osteotomy site from a side view.

FIGS. 23 and 24 illustrate the bone fixation and osteosynthesis device 710 of FIGS. 18-22 implanted between, and promoting fusion and osteosynthesis of, first and second bone segments 750, 752. Although not depicted, the devices 10, 110, 220, 310, 410, 510 and 610 may be similarly utilized as shown in FIGS. 23 and 24 to promote fusion and osteosynthesis of the first and second bone segments 750, 752. As shown in FIGS. 23 and 24, the device 710 may be inserted between the end portions of the first and second bone segments 750, 752 such that one of the engagement surfaces 720 of the wedge segment 714 engages the end of the first bone segment 750 and the opposing engagement surface 720 engages the end on the second bone segment 752. The device 710 may be implanted such that the entirety of the device 710 is contained within the site between the first and second bone segments 750, 752 (i.e., the device 710 does not extend past the outer surfaces of the end portions of the first and second bone segments 750, 752). As noted above, the end portions of the first and/or second bone segments 750, 752 may be formed by cutting or otherwise resecting the first and/or second bone segments 750, 752 to promote fusion and osteosynthesis.

The device 710 may be implanted such that the plate segment 712 is exposed and/or accessible. In this way, the fixation apertures may be utilized by driving fixation members 716 therethrough and into the end portions of the first and/or second bone segments 750, 752. The fixation apertures may be utilized by driving fixation members 716 therethrough and into the first and/or second bone segments 750, 752 to pull the first and/or second bone segments 750, 752 together and apply a compressive force that is applied across the site. In this way, the engagement surfaces 720 may be forced in abutment with, and potentially forced against, an end portion of a respective one of the first and/or second bone segments 750, 752. Further, the orientation and configuration of the device 710 may allow the primary access aperture 722 and/or the at least one alternative access aperture 726 to provide for means of introducing biologics into the interior of the porous architecture of the wedge portion 714 after implantation. The biologics introduced into the porous architecture of the wedge portion 714 may promote bone fixation and osteosynthesis of the first and second bone segments 750, 752.

As discussed above, however, the porous architecture may be in a substantially uniform or consistent pattern or a variable pattern, with at least one pattern being at least one of honeycomb, diamond, square or any other suitable shape for each cell. In addition, the porosity of these patterns could be consistent or variable depending on the need. Furthermore, the individual parts of the porous architecture, that of the individual struts may be either smooth, substantially smooth, roughened or substantially roughened.

In FIGS. 25-34 another bone fixation and osteosynthesis device is indicated generally by the reference numeral 810. The bone fixation and osteosynthesis device 810 is similar to the bone fixation and osteosynthesis devices 10, 110, 210, 310, 410, 510, 610 and 710, and therefore like reference numerals preceded by the numeral "8" are used to indicate like aspects. As indicated above the bone fixation device including a wedge portion 814 having engagement surfaces 820 can be made from a porous material such as a material having a variable porosity as disclosed in FIGS. 52-75

As discussed above, however, the porous architecture may be in a substantially uniform or consistent pattern or a variable pattern, with at least one pattern being at least one of honeycomb, diamond, square or any other suitable shape for each cell. In addition, the porosity of these patterns could be consistent or variable depending on the need. Furthermore, the individual parts of the porous architecture, that of the individual struts may be either smooth, substantially smooth, roughened or substantially roughened.

Figure 28:
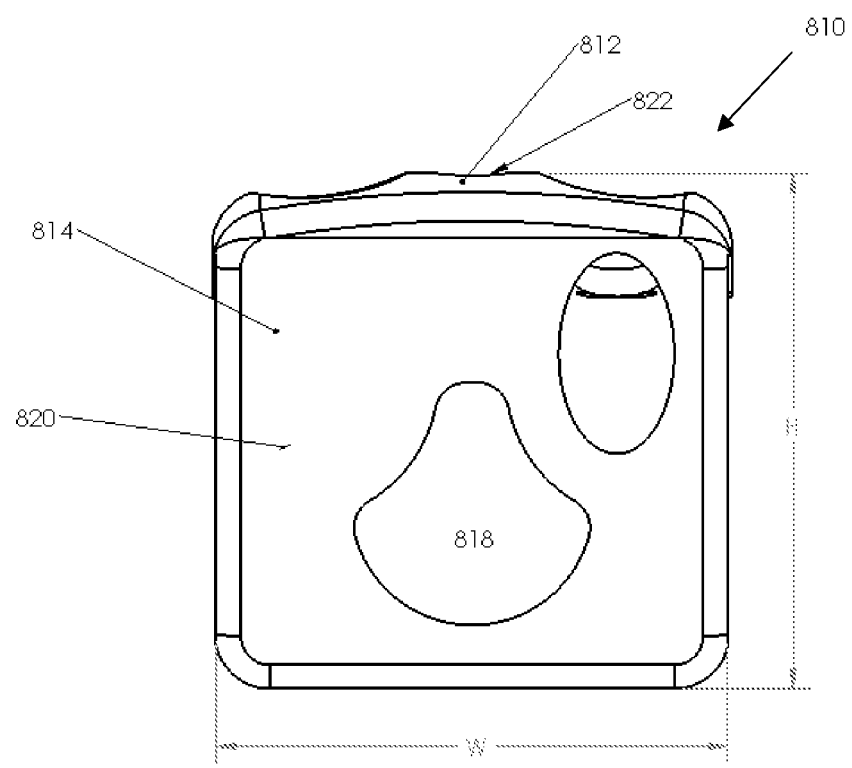
FIG. 28 is a side view of the embodiment of FIG. 25.

One difference between the device 810 and devices 10, 110, 210, 310, 410, 510, 610 and 710 is the shape or configuration of the device 810 (i.e., the shape or configuration of the plate portion 812 and the wedge portion 814). As shown in FIGS. 25-34, rather than a disc shape, the device 810 (and the wedge portion 814 itself) forms a tapered cuboid shape. For example, as shown in FIG. 28, the width W of the device 810 (e.g., as defined by the plate portion 812 and/or the wedge portion 814) may be substantially the same as the height H of the device 810 (e.g., as defined by the combination of the plate portion 812 and the wedge portion 814). In some embodiments, the width W direction of the device 810 may extend along the proximal-distal direction after implantation, and the height H direction of the device 810 may extend along the dorsal-palmar or inferior-superior direction after implantation. As shown in FIGS. 25-34, both of the engagement surfaces 820 of the wedge portion 814 may be substantially planar, and may be angled or tapered towards the other as they extend away from the plate portion 812 and toward the free end of the wedge portion 814. In this way, the engagement surfaces 820 of the wedge portion 814 may converge as they extend from the plate portion 812 to the free end of the wedge portion 814.

Figure 25:
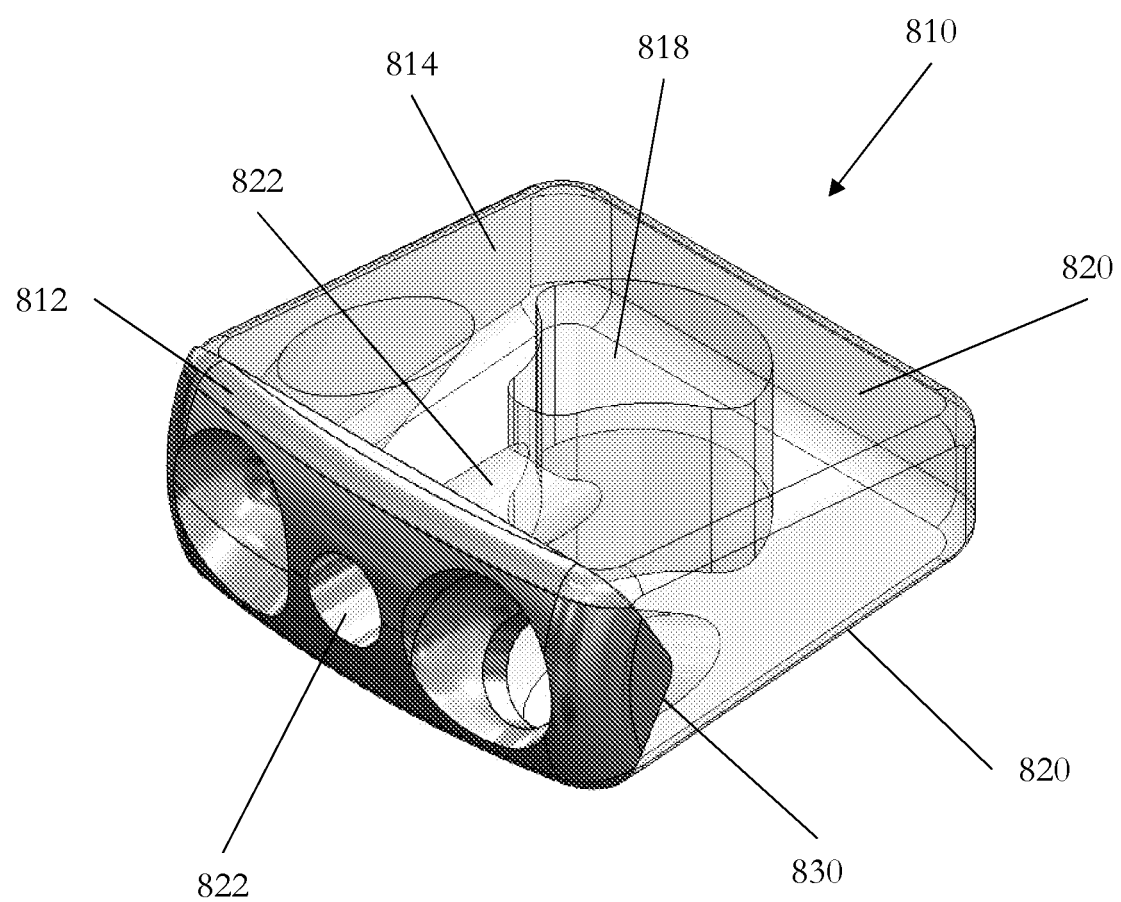
FIG. 25 is a side top perspective view of another bone fixation and osteosynthesis device according to the present disclosure.
Figure 26:
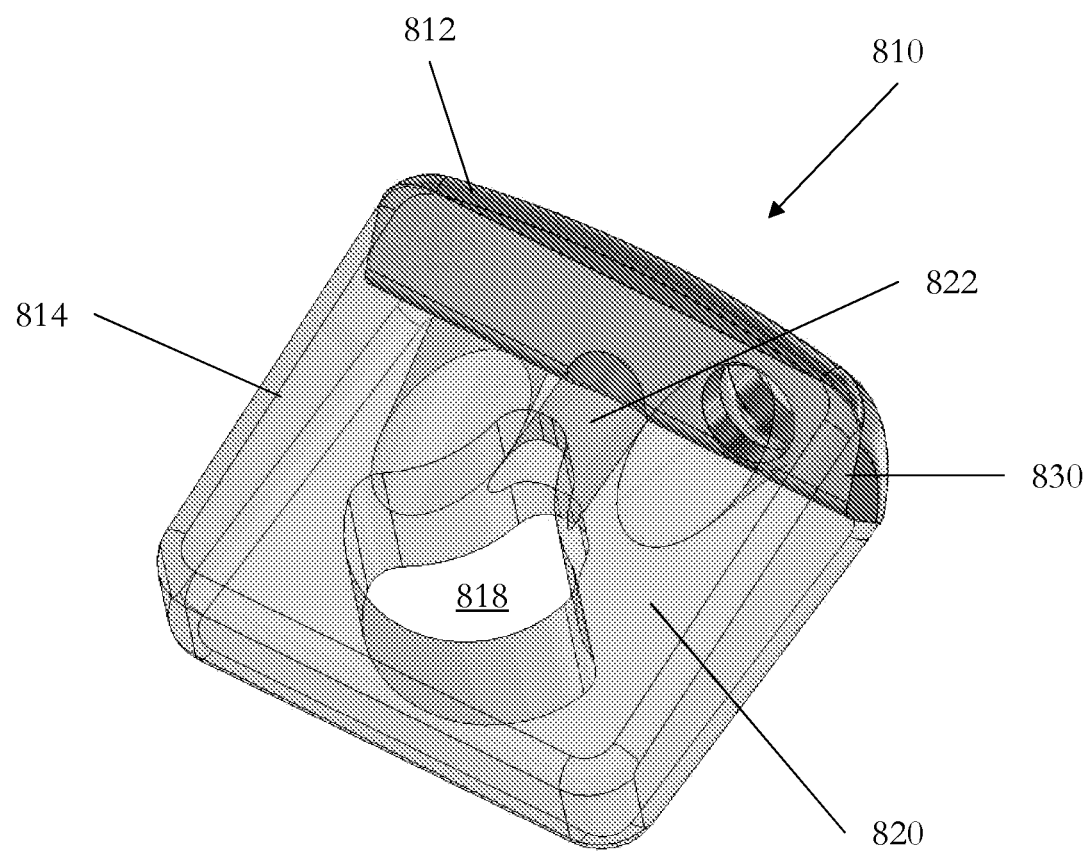
FIG. 26 is a back-side perspective view of the embodiment shown in FIG. 25.
Figure 27:
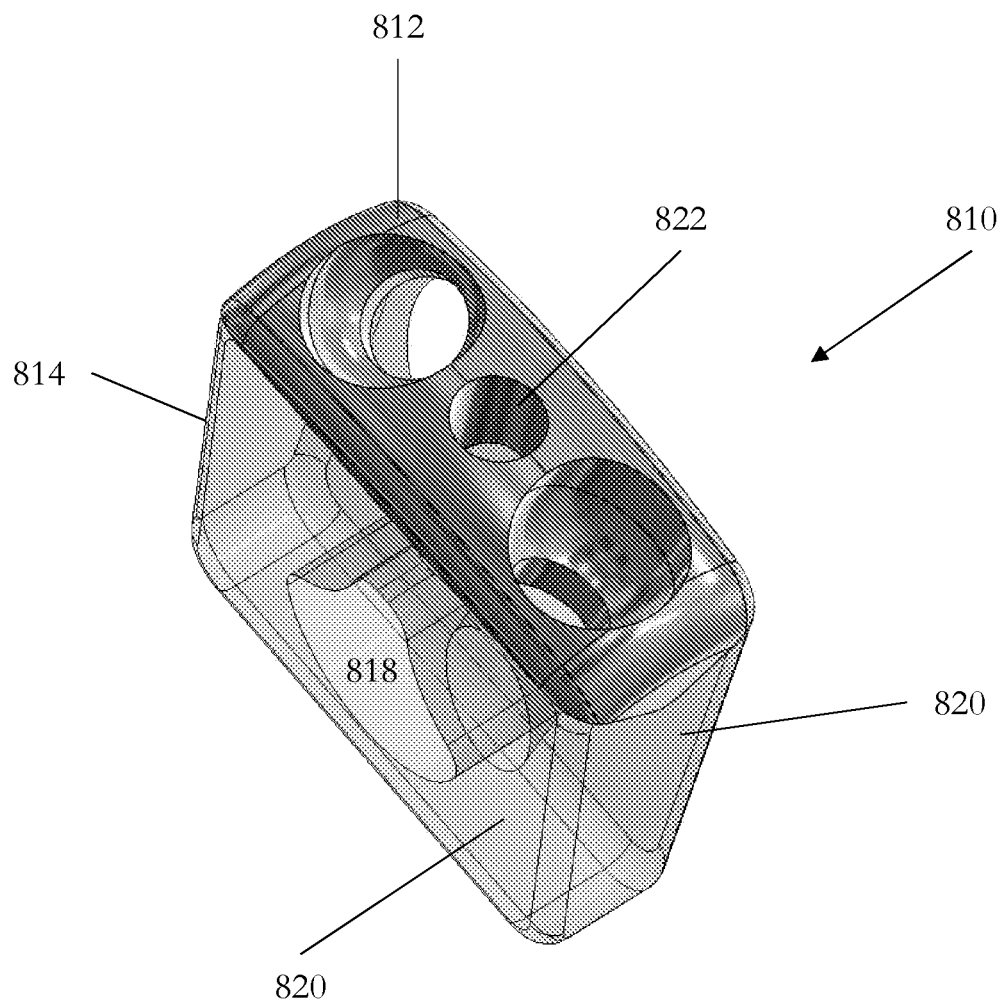
FIG. 27 is a top-side perspective view of the embodiment of FIG. 25.

FIG. 25 also shows an inner or access aperture as well. This inner or access aperture such as inner aperture 822 which may be present in each of the embodiments of the wedges, can be used for a dual purpose, that of a place to receive a fastener, wherein the fastener is configured to secure a bone plate to a bone wedge, and also to receive biologic material to promote bone growth. In this embodiment, the inner aperture is not used to fasten the plate to the wedge but rather remains open for injection of biologics.

Figure 29:
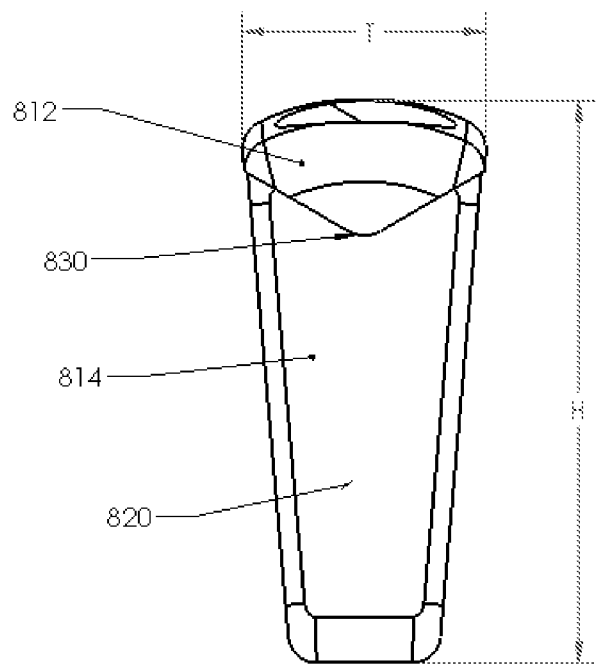
FIG. 29 is an end view of the embodiment of FIG. 25
Figure 30:
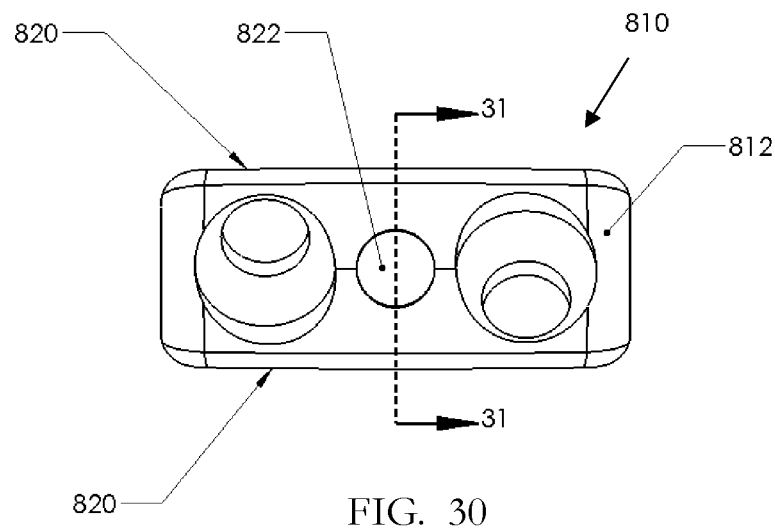
FIG. 30 is a top view of the embodiment of FIG. 25.
Figure 31:
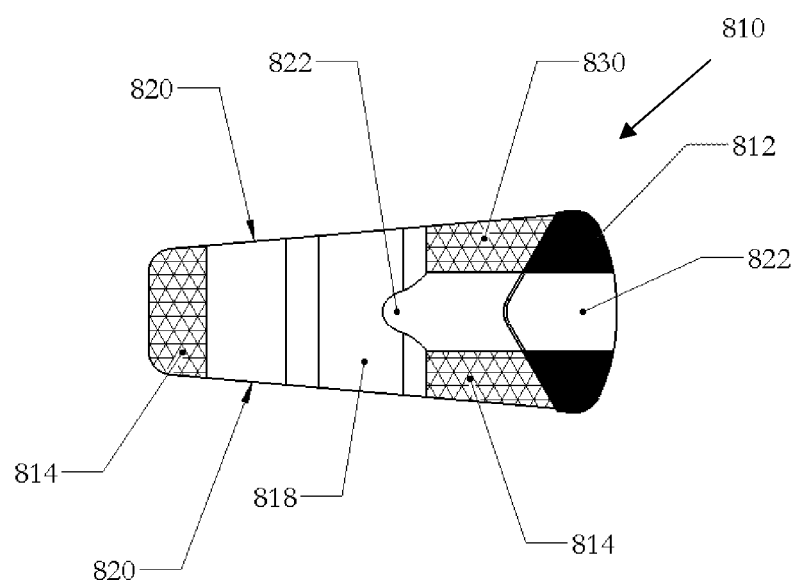
FIG. 31 is a side cross-sectional view of the embodiment shown in FIG. 25 taken along line 31-31 shown in FIG. 30.
Figure 32:
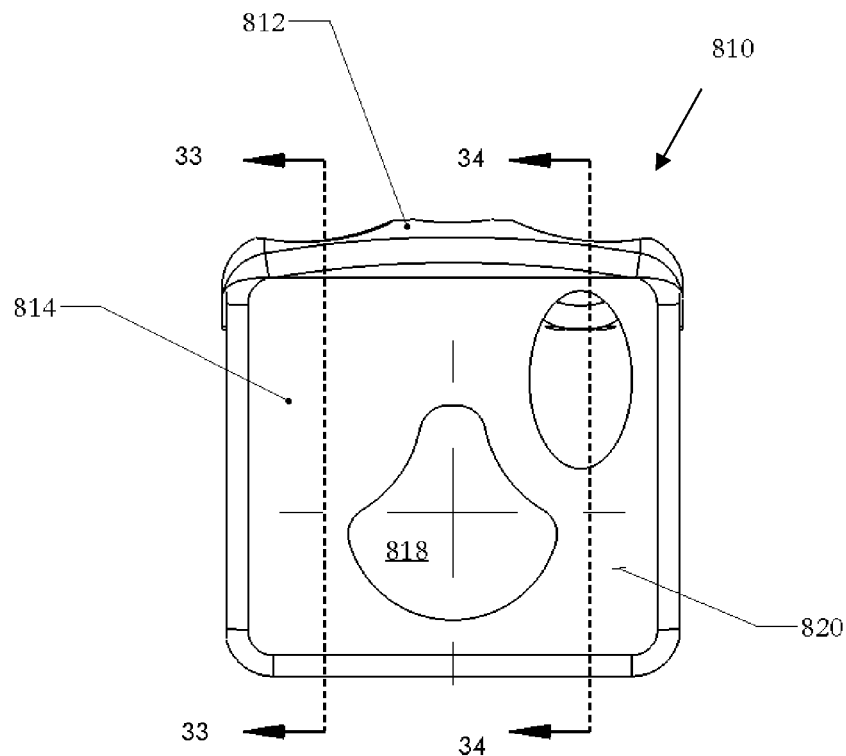
FIG. 32 is a side view of the embodiment shown in FIG. 25.
Figure 33:
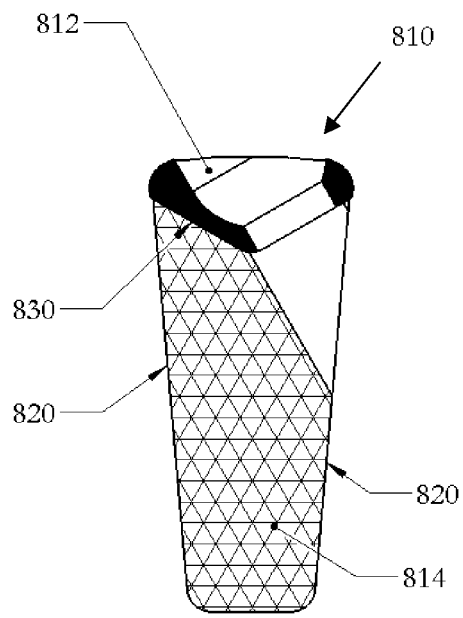
FIG. 33 is a side cross-sectional view taken along the line 33-33 shown in FIG. 32.
Figure 34:
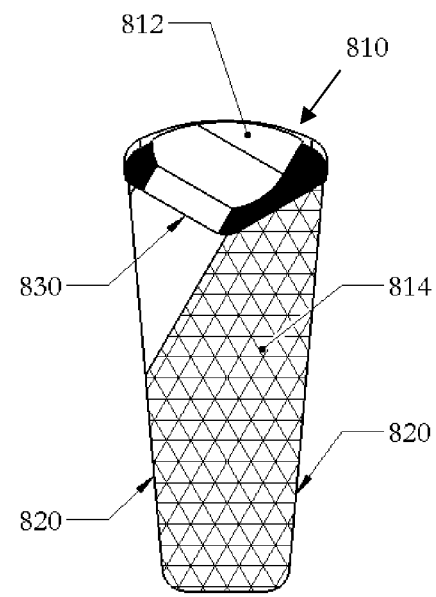
FIG. 34 is a side cross-sectional view taken along the line 34-34 shown in FIG. 32.

FIG. 28 shows that the device 810 has a width W, and a height H. FIG. 29 shows that the device has a thickness T. The width W, height H and thickness T of the device 810 (i.e., the plate portion 812 and/or the wedge portion 814) may vary, as shown in FIGS. 25-34. For example, in some embodiments the width W of the device 810 (e.g., as defined by the plate portion 812 and/or the wedge portion 814) may range from about 10 mm to about 35, or about 18 mm to about 22 mm, as shown in FIG. 28. Similarly, in some embodiments the height H of the device 810 (e.g., as defined by the plate portion 812 and/or the wedge portion 814) may range from about 10 mm to about 35, or about 18 mm to about 22 mm, as shown in FIG. 28. As noted above, the width W of the device 810 may be substantially the same as the height H of the device 810. The thickness T of the device, as shown in FIG. 29, may be larger at the end plate portion 812 than at the free end of the wedge portion 814. In some embodiments, the thickness T of the device 810 at the plate portion 812 may range from about 4 mm to about 18, or about 8 mm to about 12 mm, as shown in FIG. 28. The thickness T of the device 810 may taper from the plate portion 812 to the free end of the wedge portion 814 (e.g., along the proximal-distal direction) at an angle within the range of about 5 degrees to about 30 degrees, or about 10 degrees to about 20 degrees. When the device 810 is configured with a width W (e.g., as defined by the plate portion 812 and/or the wedge portion 814) within the range of about 18 mm to about 22 mm, a height H (e.g., as defined by the plate portion 812 and the wedge portion 814) within the range of about 18 mm to about 22, a thickness T at the plate portion 812 within the range of about 8 mm to about 12 mm (.g., as defined by the plate portion 812), and a taper to the engagement surfaces 820 along the proximal-distal direction within the range of about degrees to about 20 degrees, the device 810 may be particularly well suited to promote fusion and osteosynthesis of a calucanous (calcaneous) bone, such as in an Evans Osteotomy.

As shown in FIGS. 25, 29, 31, 33 and 34, the back or dorsal surface 830 of the plate portion 812, from which the bone wedge portion 814 may extend, may be convex. The corresponding side or surface of the wedge portion 814 may thereby be concave. In some embodiments, the surface 830 of the plate portion 812 may define a V-shaped protrusion centered in the thickness T of the plate portion 812 and extending across the width W of the plate portion 812.

In FIGS. 35-42, another bone fixation and osteosynthesis device is indicated generally by the reference numeral 910. The bone fixation and osteosynthesis device 910 is substantially similar to the bone fixation and osteosynthesis device 810, and therefore like reference numerals preceded by the numeral "9" are used to indicate like aspects. In addition, the wedge portion 914 can have the same type of porosity of the embodiments of the wedges of FIGS. 52-75. This wedge portion 914 has surfaces 920 which are configured to interact with adjacent bone. A difference between the device 910 and the device 810 is the including of a substantially solid framework or support structure 928 extending within the porous architecture of the wedge portion 914. Stated differently, the porous architecture of the wedge portion 914 is formed or extends from, within and/or about a substantially solid framework 928. The framework 928 may be closed portions of the porous architecture. In this way, the wedge portion 914 of the device 910 includes the porous architecture in combination with the substantially solid framework 928 or cross section. The substantially solid framework 928 may strengthen and/or stiffen the wedge portion 914. The framework 928 may be provided at the exterior of the wedge portion 914, as shown in FIGS. 35-42. In other embodiments, the framework 928 may be provided within the interior of the wedge portion 914 instead of, or in addition to, at the exterior of the wedge portion 914. This framework may be substantially smooth in structure or substantially roughened. The wedge portion 910 may also contain an inner or access aperture 922. This inner or access aperture such as inner aperture 922 which may be present in each of the embodiments of the wedges, can be used for a dual purpose, that of a place to receive a fastener, wherein the fastener is configured to secure a bone plate to a bone wedge, and also to receive biologic material to promote bone growth. In this embodiment, the inner aperture 922 is not used to fasten the plate to the wedge but rather remains open for injection of biologics.

As shown in FIGS. 35-42, the substantially solid framework 928 may include a plurality of substantially solid strut or beams elements extending along the width W, height H and/or thickness T directions. The outer periphery of the wedge portion 914 may include a plurality of interconnected (or, alternatively, separate or distinct) substantially solid strut elements.

As discussed above, however, the porous architecture may be in a substantially uniform or consistent pattern or a variable pattern, with at least one pattern being at least one of honeycomb, diamond, square or any other suitable shape for each cell. In addition, the porosity of these patterns could be consistent or variable depending on the need. Furthermore, the individual parts of the porous architecture, that of the individual struts may be either smooth, substantially smooth, roughened or substantially roughened For example, as shown in FIGS. 35-42 the outer peripheral edges of the engagement surfaces 920 may include the substantially solid framework 928 extending thereabout and from the plate portion 912. Such framework 928 may add strength to the wedge portion 914, above that provided by the porous architecture, in the width W and/or height H directions. The framework 928 may also extend between the engagement surfaces 920 along the thickness T direction to add strength to the wedge portion 914, above that provided by the porous architecture, in the thickness T direction.

As shown in FIGS. 35-42, the framework 928 may include substantially solid strut elements extending between the substantially solid strut elements extending about the periphery of the engagement surfaces 920. Further, the framework 928 may include substantially solid strut elements extending about the periphery of the inner aperture 918 at each engagement surface 920, and substantially solid strut elements extending therebetween along the thickness T direction, as shown in FIGS. 35-42. In some embodiments, the framework 928 may include substantially solid strut elements extending substantially radially out from the periphery of the inner aperture 918. Such strut elements may extend substantially radially from a strut element extending about the periphery of the inner aperture 918 to a strut element extending about the periphery of a corresponding engagement surface 920 and/or the plate portion 912. As discussed above, although the framework 928 is depicted in FIGS. 35-42 as formed of substantially solid strut elements extending from the exterior of the wedge portion 914 and only partially within the interior of the porous architecture of the wedge portion 914, the framework 928 may include one or more substantially solid strut element extending through the architecture of the wedge portion 914 and/or positioned fully within the architecture of the wedge portion 914.

For example, in at least one embodiment as shown in FIG. 35a, there is another embodiment of an osteosynthesis device 910a which includes a framework such as framework 928a having a wedge portion such as wedge portion 914a, 914d, 914g, 914h, 914i, 914j, 914k. These wedge portions can be formed from a lattice structure such as a variable lattice structure that can have a variable porosity such as that disclosed in FIGS. 53-75 for example. In at least one particular embodiment, this osteosynthesis device comprises wedge portions such as wedge portion 914d which extends beyond a frame such as frame 928a. In at least one embodiment, this extension can be in the order of at least 0.5 millimeters providing a side face 914f width. In at least one additional embodiment, this extension can be in the order of at least one millimeter which provides the side face such as side face 914f with a width as well. Since this wedge portion extends beyond the frame, it has multiple exposed faces including the outer face 914e, as well as a plurality of side faces such as side face 914f. Thus, for example with this wedge portion extending beyond the frame, this wedge portion can have in at least one embodiment five sides exposed beyond the frame such as a main face such as face 914e, and a plurality of side faces 914f, which can number as up to at least four side faces forming a box around the main face. Because of the additional extension of this wedge portion having variable porosity extending beyond this frame such as frame 928a, it allows for many additional faces for interaction with an adjacent bone structure. The porosity of this wedge structure therefore allows for increased interaction with bone on multiple different planes at multiple different angles. For example, front face 914e is substantially perpendicular in orientation to side face 914f. This difference in orientation allows for bones intersecting with this wedge device at different angles to have different points of intersection. This allows for a more stable and secure meshing between the wedge portion 914d and an adjacent bone. In addition, shown in this drawing are multiple different wedge portions 914a, 914h, 914g, 914i 914j and 914k. In addition, additional frame elements such as frame element 928b and 928c are also shown as well wrapping around these wedge portions allowing these wedge portions to extend beyond this frame. For example, each of the frames 928 extend in at least two planes, a first plane 928.1 and 928.2. In addition, each of the wedge portions extend in at least two different planes as well such as along a first plane 914.1, and 914.2. As shown, at least one plane of the faces of the wedge portion such as plane 914.1 extend beyond or outside at least one plane of the frame such as plane 928.1

Figure 35:
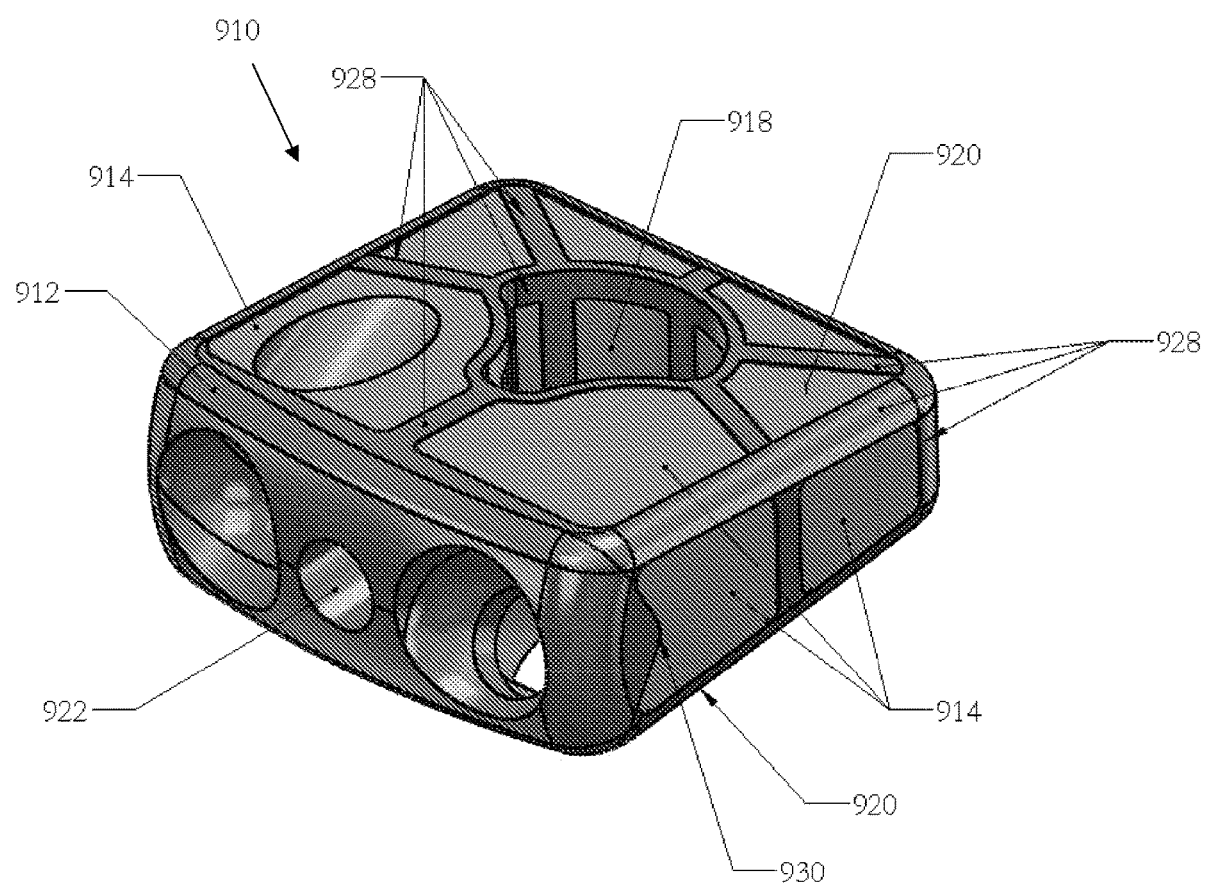
FIG. 35 is a top-side perspective view of another bone fixation and osteosynthesis device according to the present disclosure.
Figure 35B:
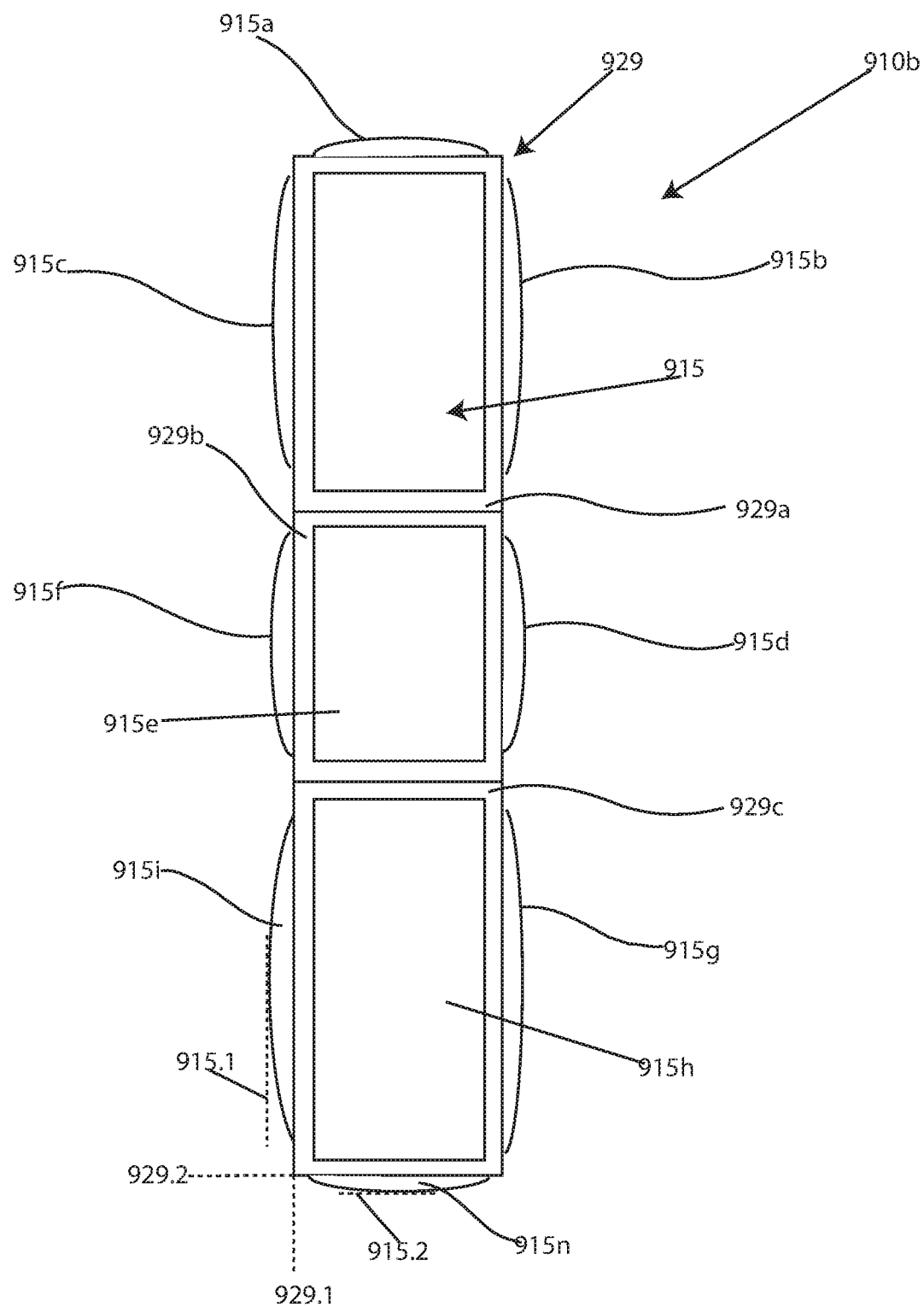
FIG. 35B is a side view of another embodiment of the wedge portion.
Figure 36:
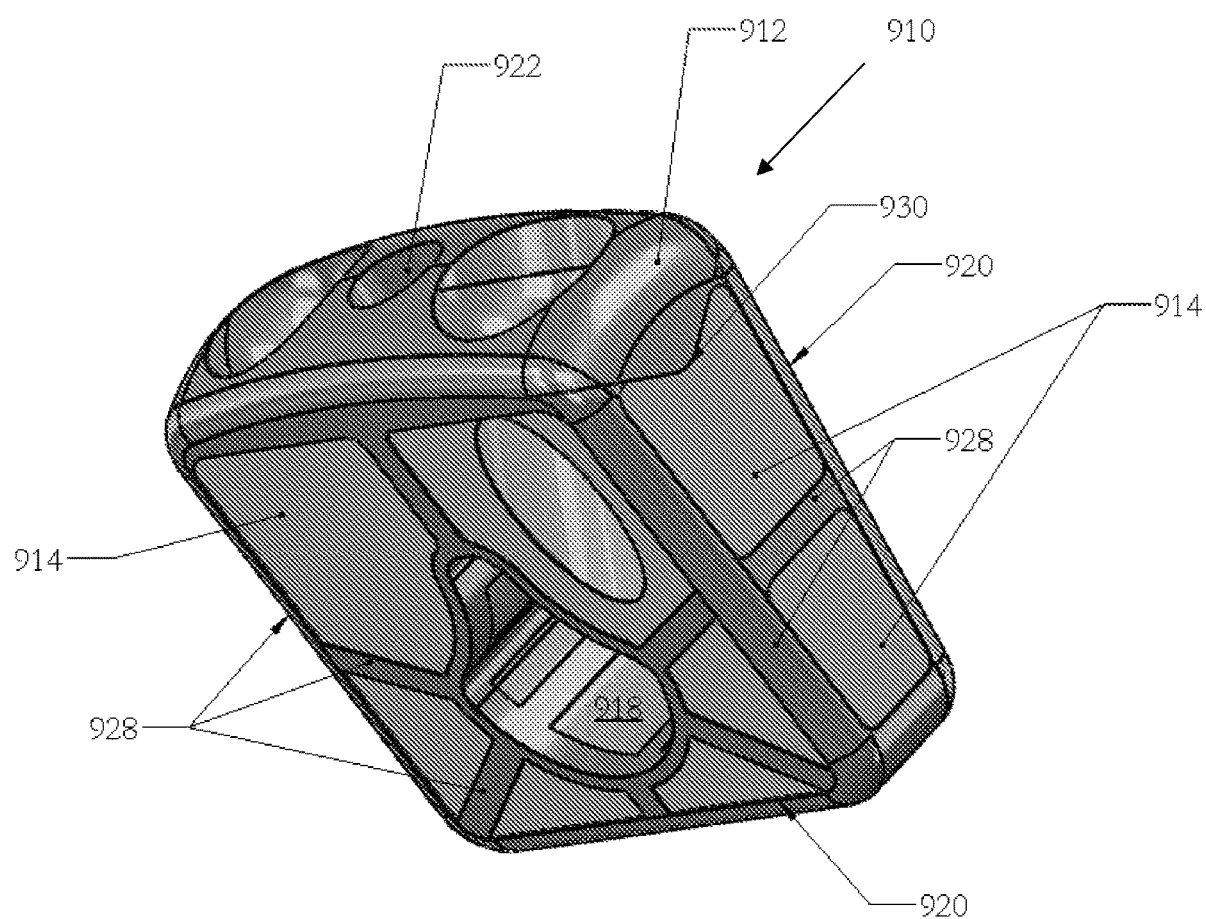
FIG. 36 is a top side perspective view of the embodiment shown in FIG. 35.
Figure 37:
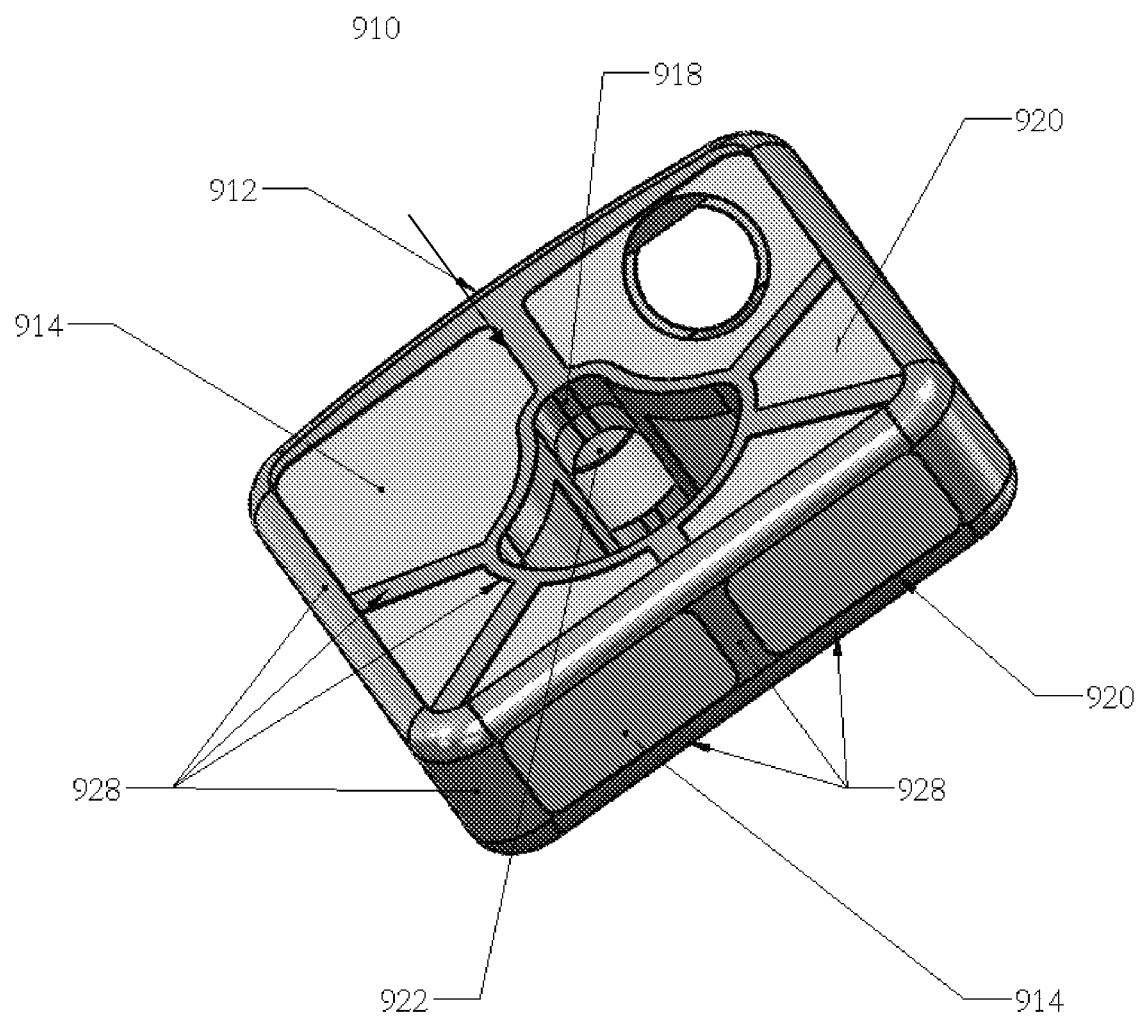
FIG. 37 is a bottom side perspective view of the embodiment shown in FIG. 35.
Figure 38:
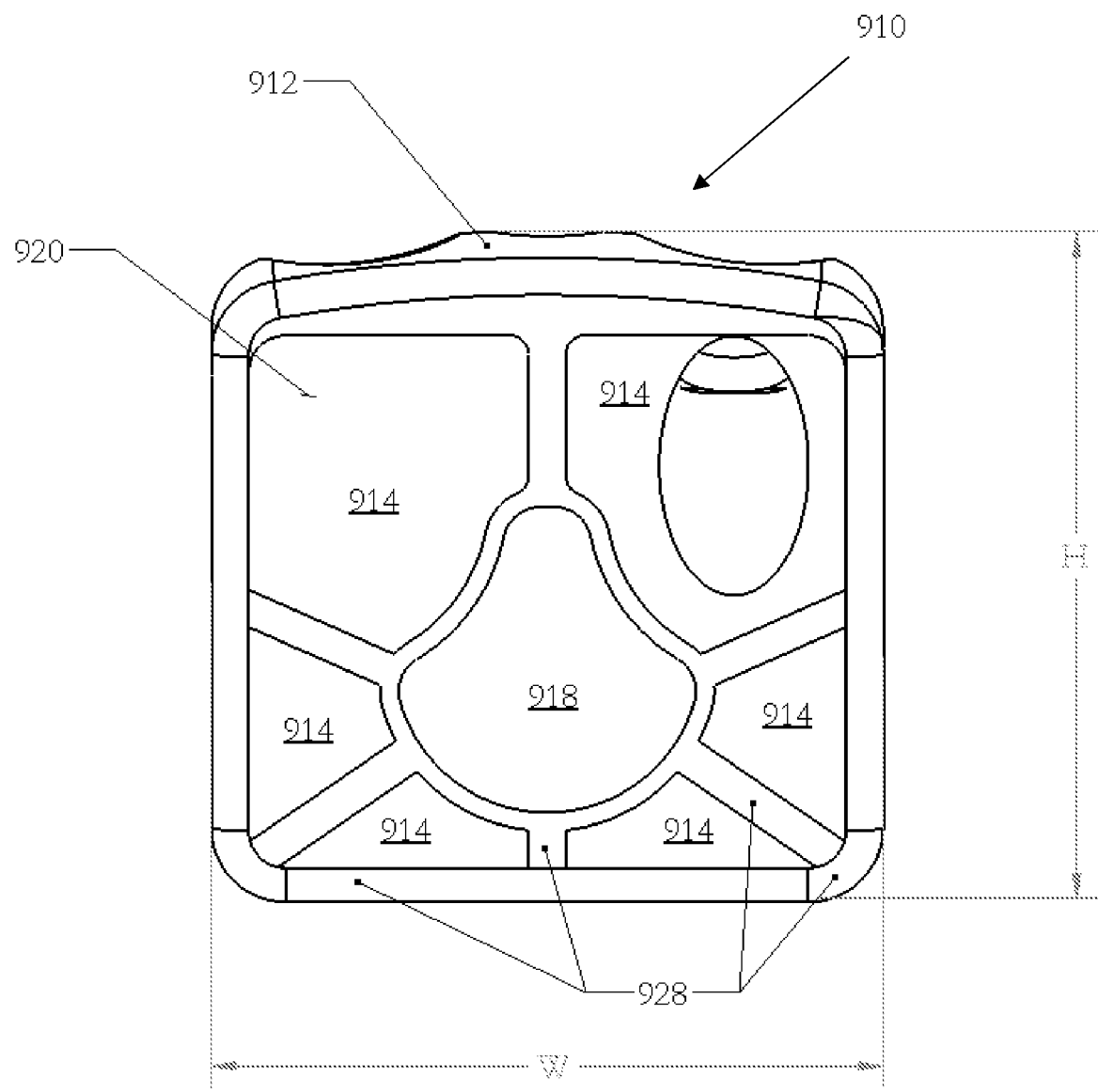
FIG. 38 is a side view of the embodiment shown in FIG. 35.
Figure 39:
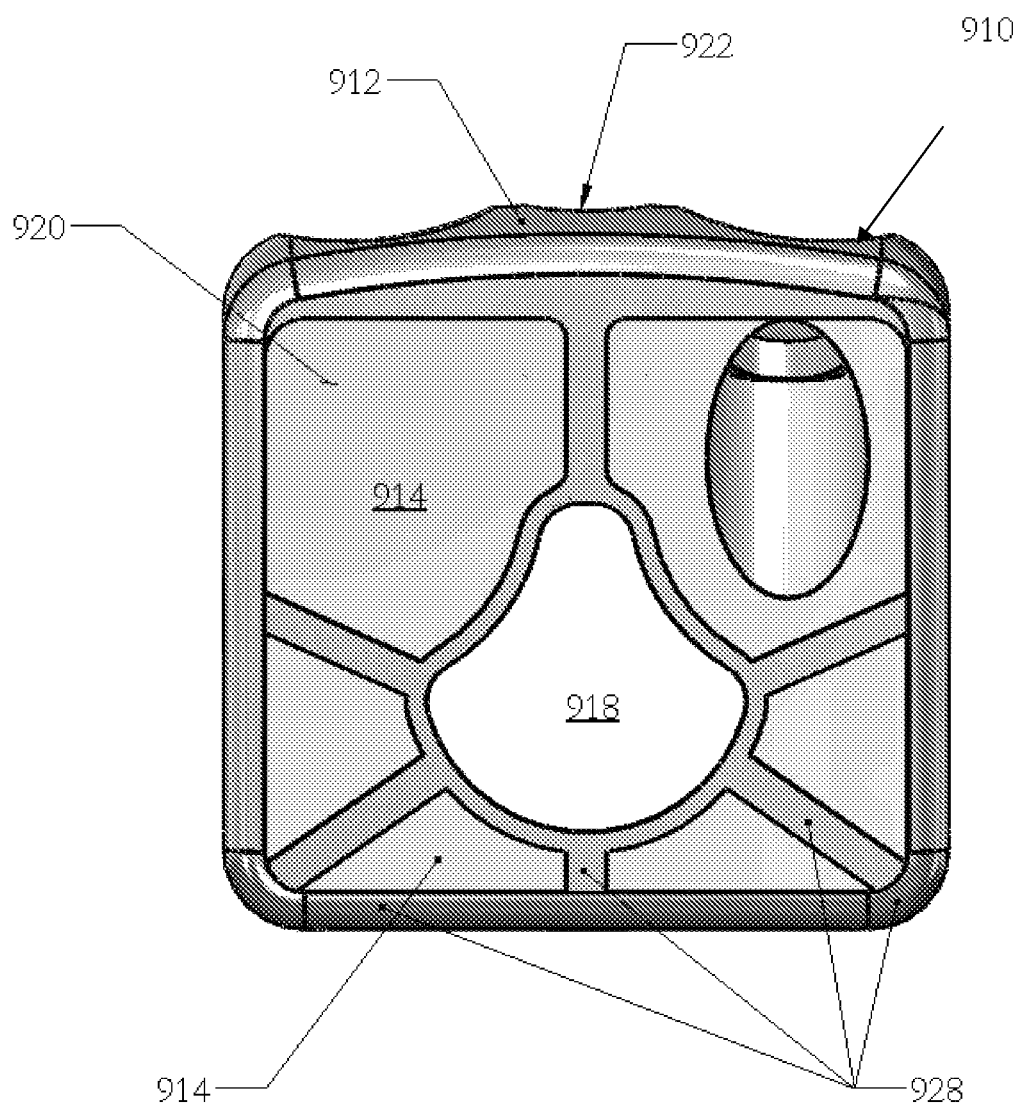
FIG. 39 is another view of the embodiment shown in FIG. 35.
Figure 40:
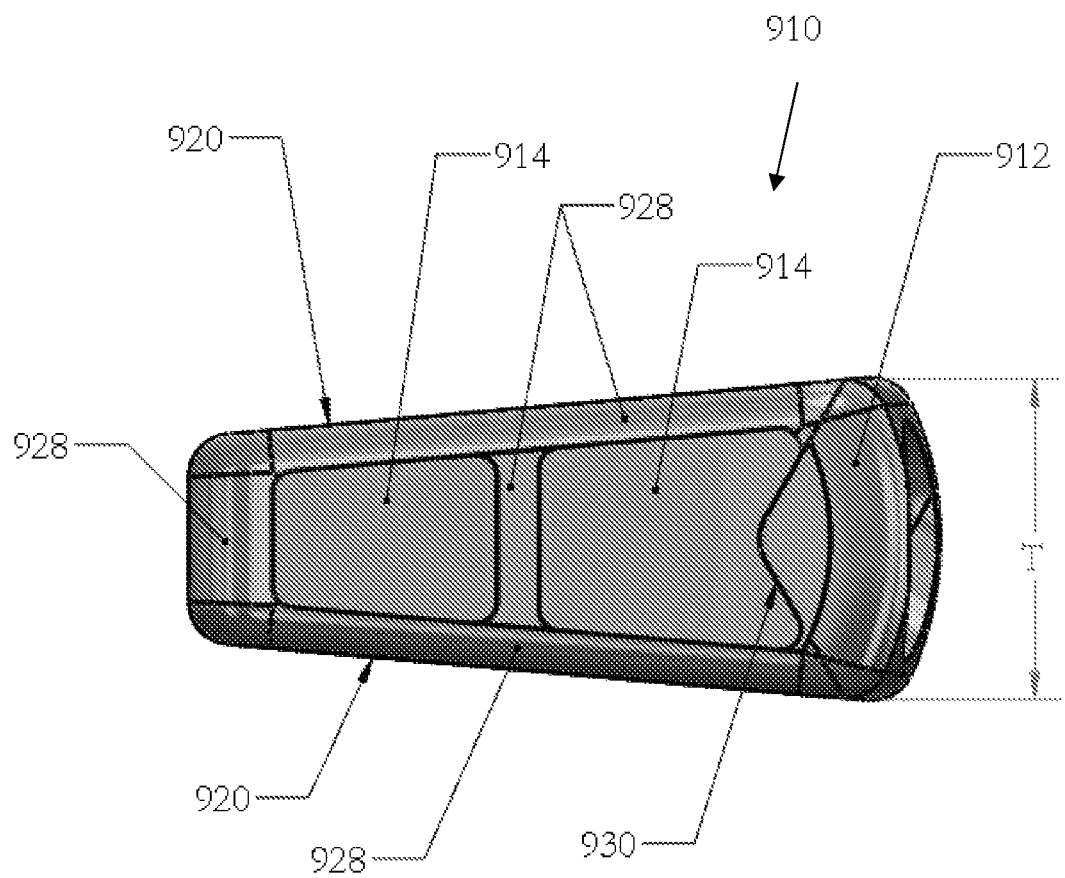
FIG. 40 shows a side view of the embodiment shown in FIG. 35.
Figure 41:
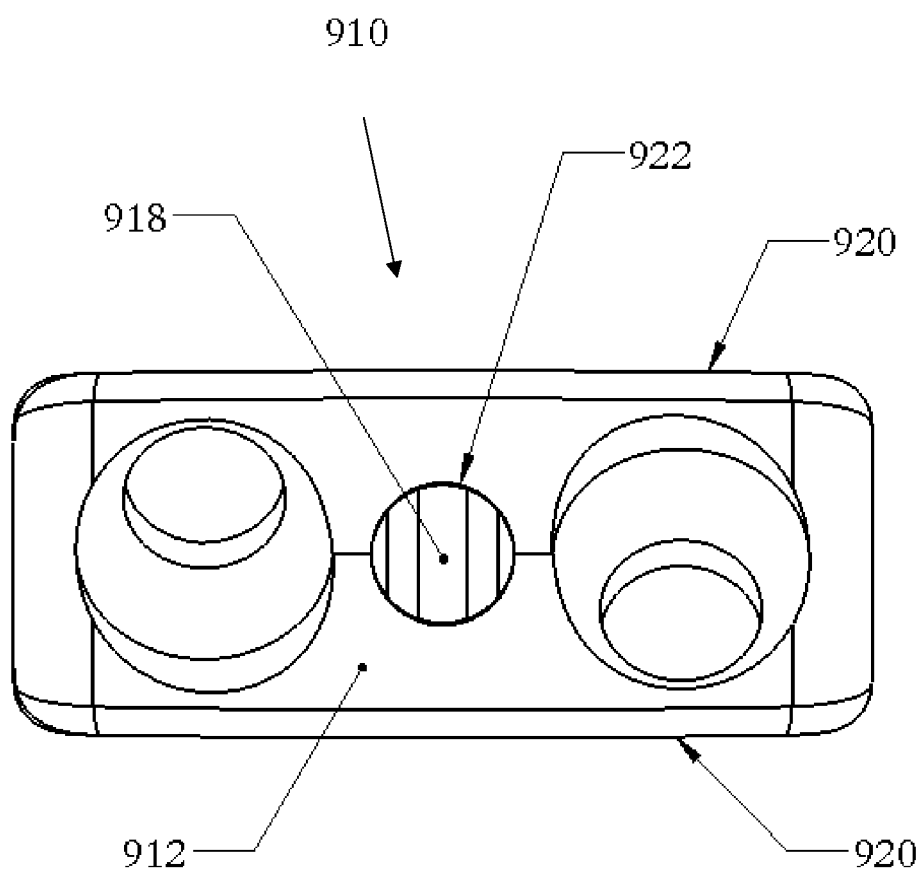
FIG. 41 is a top view of the embodiment shown in FIG. 35.
Figure 42:
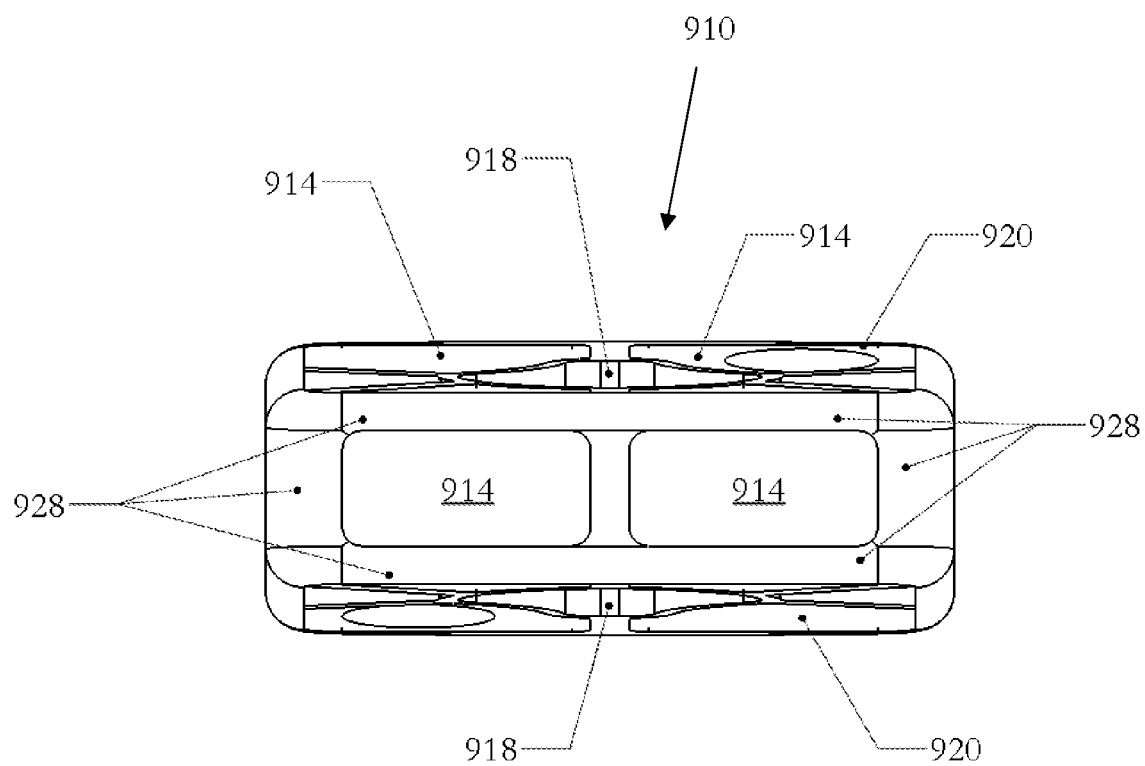
FIG. 42 is a bottom view of the embodiment shown in FIG. 35.
Figure 43:
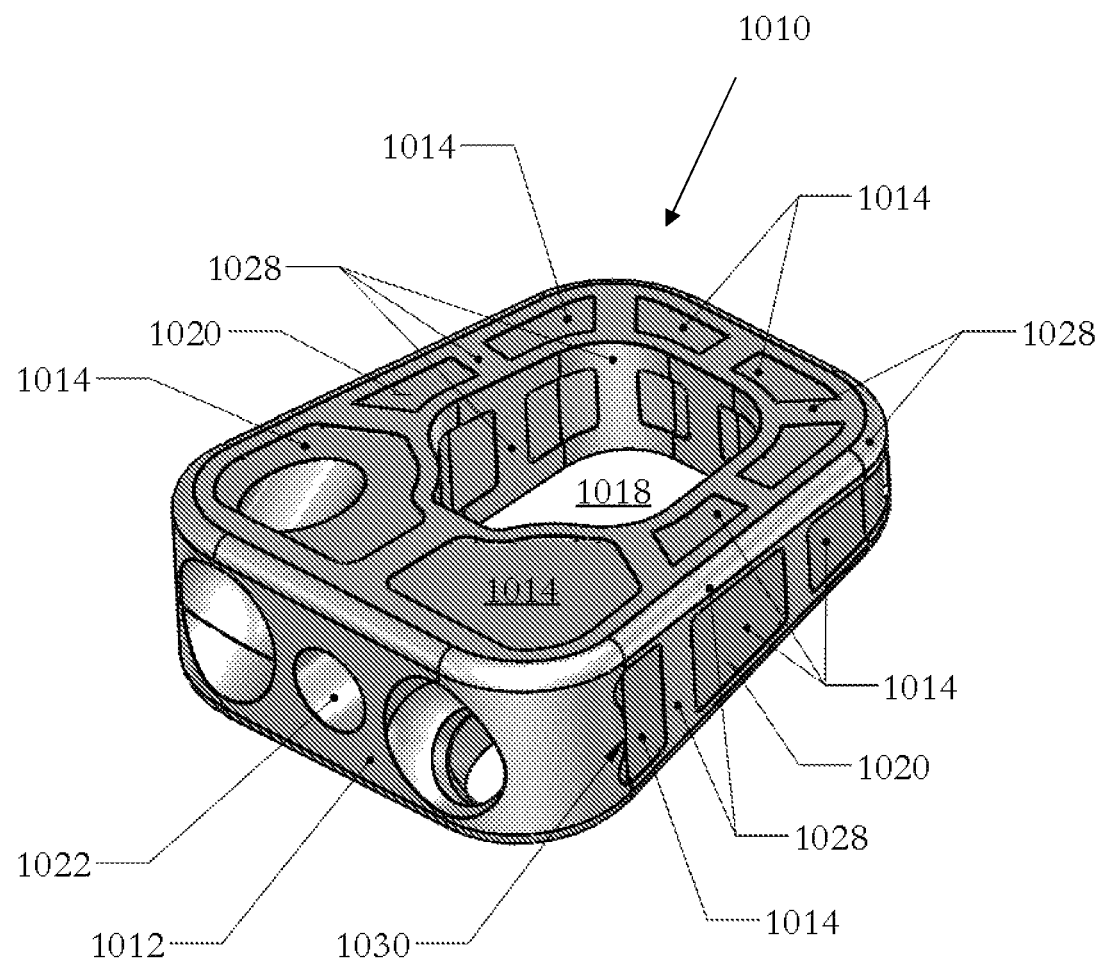
FIG. 43 illustrates another bone fixation and osteosynthesis device.
Figure 44:
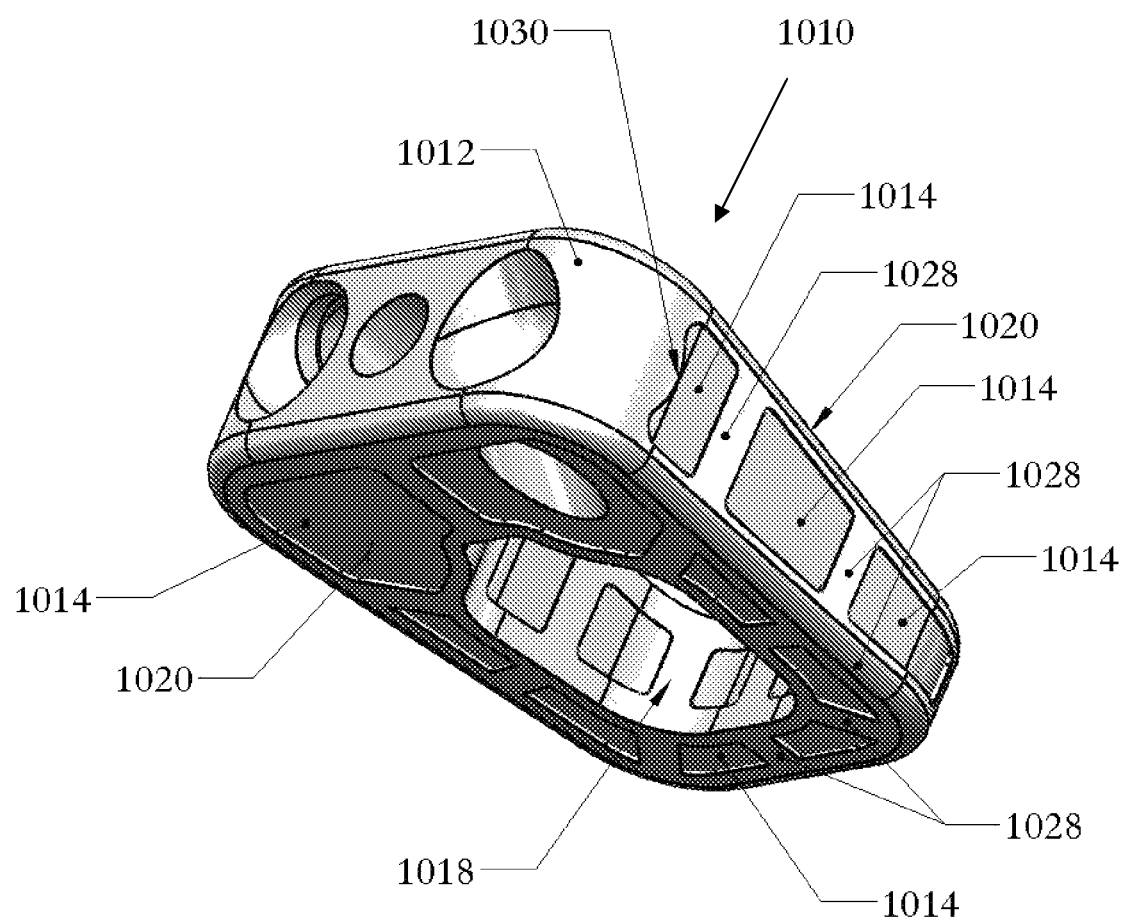
FIG. 44 is a top side perspective view of the bone fixation and osteosynthesis device shown in FIG. 35.
Figure 45:
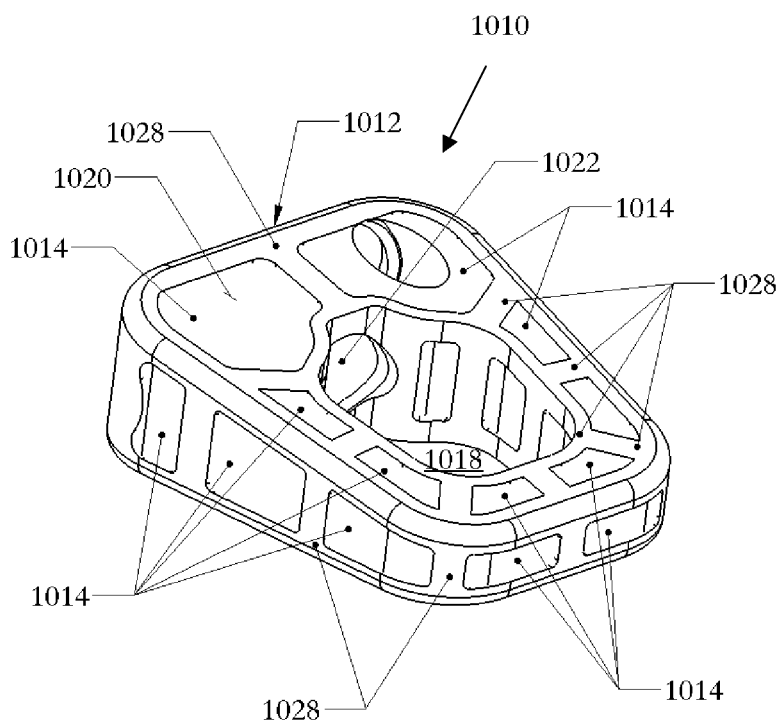
FIG. 45 is a bottom-side perspective view of the embodiment of FIG. 43.
Figure 46:
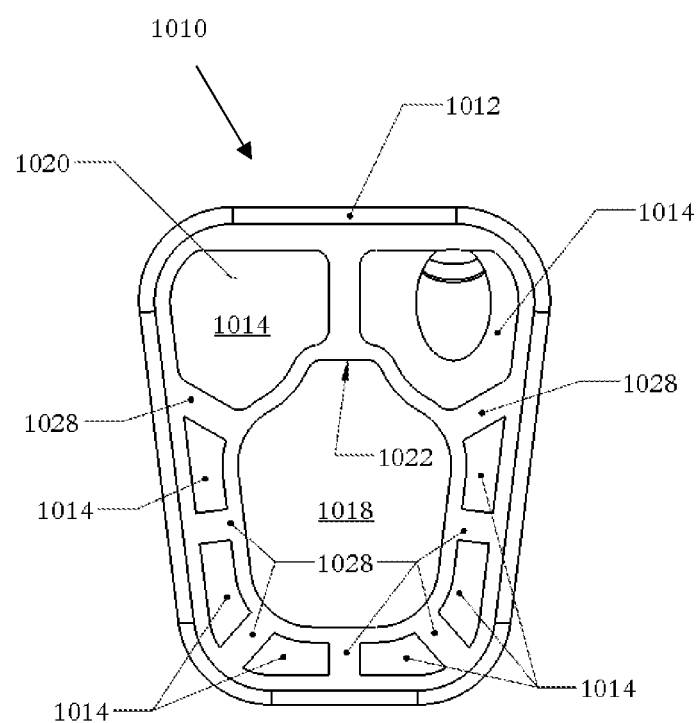
FIG. 46 is a side view of the embodiment of FIG. 43.

In another embodiment as shown in FIG. 35B, there is another embodiment of an osteosynthesis device 910b which has both a wedge portion such as wedge portions 915a, 915b and 915c which are positioned inside of frame 929a. With this design, the wedge portions 915a, 915b, 915c have a rounded surface and this rounded surface has multiple, and in at least this case many different surfaces. These many different surfaces allow for many different surfaces or faces for interaction with an adjacent bone or body part. With this device 910b there are also many adjacent frames such as frame 929b which is configured to receive multiple different wedge portions 915d, 915e, and 915f which are configured to have either a rounded surface or multiple different surfaces or faces for interaction with an adjacent bone or body part. As indicated above these wedge sections can be made from porous material which can have a consistent porosity or a variable porosity as disclosed in FIGS. 53-75. As discussed above, however, the porous architecture may be in a substantially uniform or consistent pattern or a variable pattern, with at least one pattern being at least one of honeycomb, diamond, square or any other suitable shape for each cell. In addition, the porosity of these patterns could be consistent or variable depending on the need. Furthermore, the individual parts of the porous architecture, that of the individual struts may be either smooth, substantially smooth, roughened or substantially roughened.

With this embodiment, at least one plane 915.1 or 915.2 of the wedge portion 915, extends beyond or outside of at least one plane such as plane 929.1 or 929.2 respectively of the frame.

Figure 47:
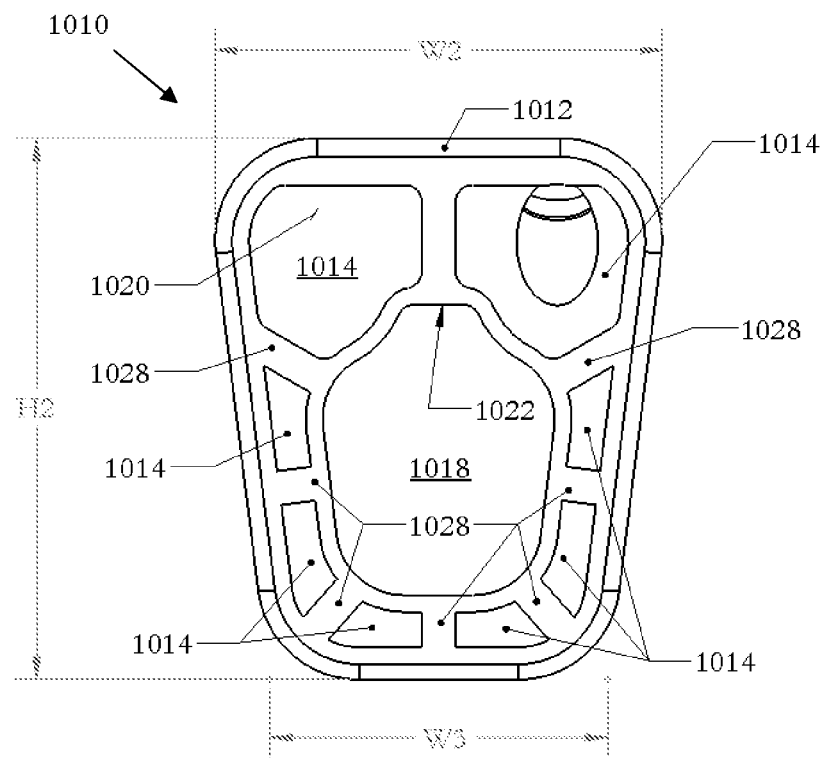
FIG. 47 is another side view of the embodiment of FIG. 43.
Figure 48:
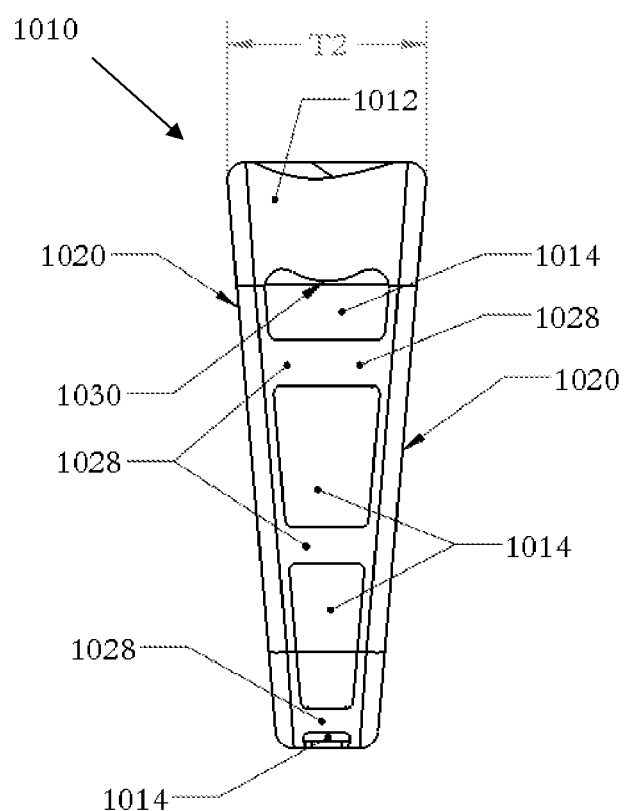
FIG. 48 is a side view of the embodiment of FIG. 43.
Figure 49:
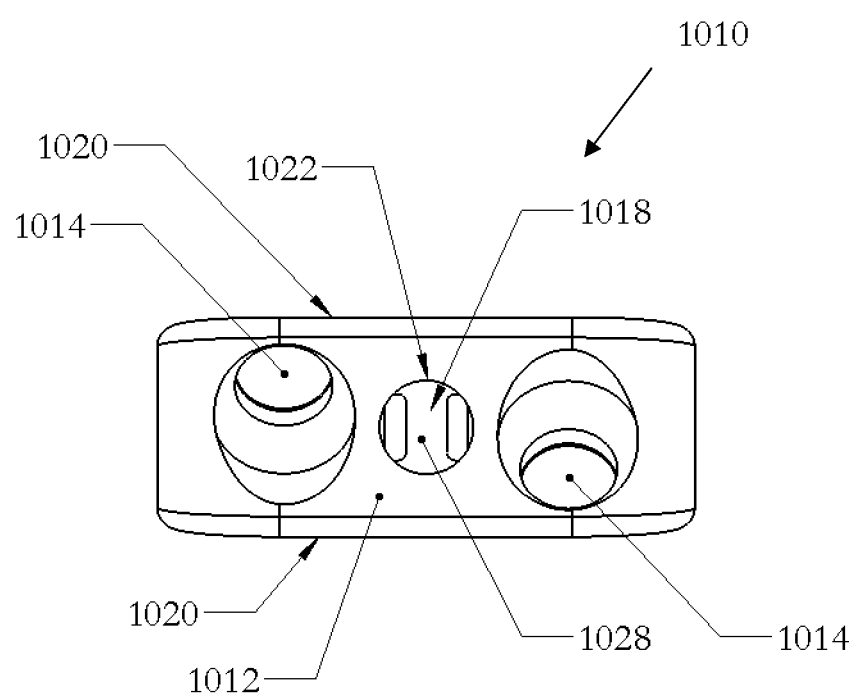
FIG. 49 is a top view of the embodiment of FIG. 43.
Figure 50:
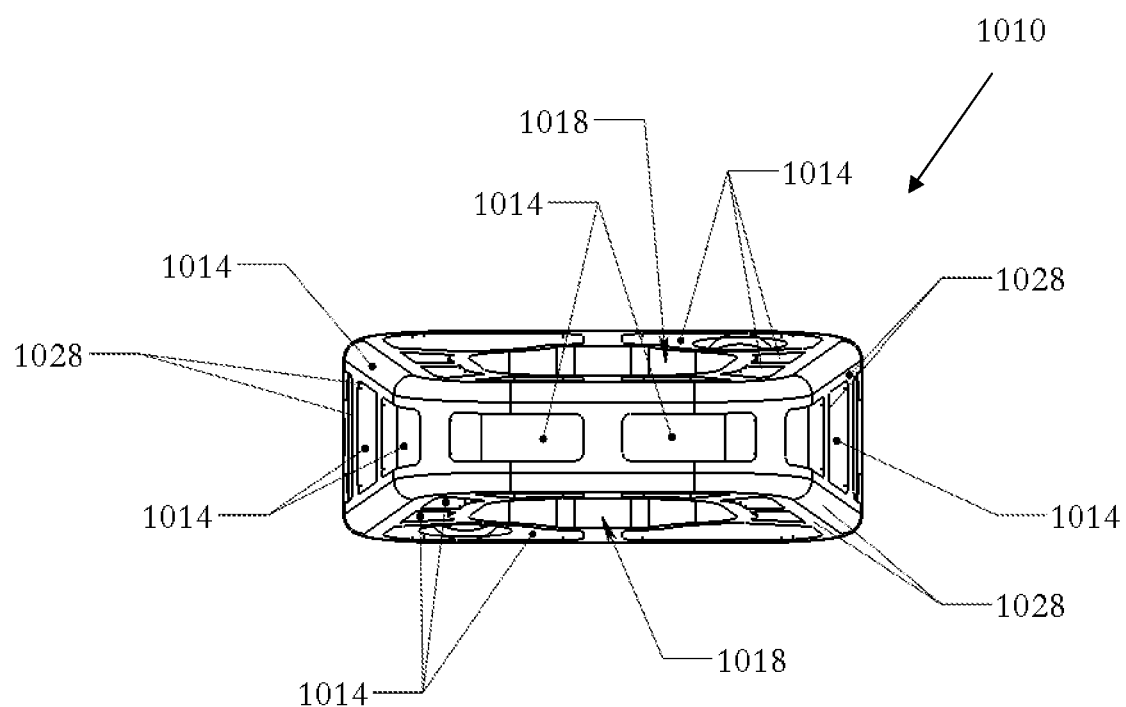
FIG. 50 is a bottom end view of the embodiment of FIG. 43.

In FIGS. 43-50 another bone fixation and osteosynthesis device is indicated generally by the reference numeral 1010. The bone fixation and osteosynthesis device 1010 is substantially similar to the bone fixation and osteosynthesis device 910, and therefore like reference numerals preceded by the numeral "10" are used to indicate like aspects. A difference between the device 1010 and the device 910 is the shape, size and/or configuration of the device 1010. As shown in FIGS. 47 and 48, rather than a tapered cuboid shape, the device 1010 (e.g., the wedge portion 1014) tapers from a thickness T2 and a width W2 proximate to or at the plate or frame portion 1012. For example, as shown in FIG. 47 the width of the device 1010 may taper from a first width W2 at a portion of the wedge portion 1014 proximate to the plate or frame portion 1012 to a second width W3 at the free end of the wedge portion 1014. In at least one embodiment the wedge portion has a porosity of any one of the wedges outlined in FIGS. 51-75. Further, as shown in FIGS. 43-47, the height H2 of the device 1010 may be greater than the first width W2 of the device 1010 proximate to the plate portion 1012 and the second width W3 of the device at the free end of the wedge portion 1014.

This framework or frame portion 1012 may be substantially smooth in structure or substantially roughened. The wedge portion 1014 may also contain an inner or access aperture 1022. This inner or access aperture such as inner aperture 1022 which may be present in each of the embodiments of the wedges, can be used for a dual purpose, that of a place to receive a fastener, wherein the fastener is configured to secure a bone plate to a bone wedge, and also to receive biologic material to promote bone growth. In this embodiment, the inner aperture 1022 is not used to fasten the plate to the wedge but rather remains open for injection of biologics.

The first and second widths W2, W3, the height H2 and the thickness T2 of the device 1010 (e.g., the plate portion 1012 and/or the wedge portion 1014) may vary. For example, in some embodiments the first width W2 of the device 1010 (e.g., as defined at or proximate to the plate or frame portion 1012) may range from about 8 mm to about 16, and the second width W3 of the device 1010 (e.g., as defined at the free end of the wedge portion 1012) may range from about 6 mm to about 14 mm, as shown in FIG. 47. Similarly, in some embodiments the height H2 of the device 1010 (e.g., as defined by the plate portion 1012) may range from about 10 mm to about 30, as shown in FIG. 47. As noted above, the first width W2 of the device 1010 may be greater than the second width W3 of the device, and the height H2 of the device 1010 may be greater than both the first and second widths W2, W3 of the device 1010. In some embodiments, the thickness T2 of the device 1010 at the plate or frame portion 1012 may range from about 3 mm to about 12 mm, as shown in FIG. 48. The thickness T2 of the device 1010 may taper from the plate portion 1012 to the free end of the wedge portion 1014 (e.g., along the proximal-distal direction) at an angle within the range of about 5 degrees to about 25 degrees. In such a configuration of the first width W1, the second width W2, the height H2, the thickness T2 and the taper of the thickness of the device 1010, the device 1010 may be particularly well suited to promote fusion and osteosynthesis of a medial cuneiform bone, such as in a Cotton osteotomy procedure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

As may be recognized by those of ordinary skill in the art based on the teachings herein, numerous changes and modifications may be made to the above-described and other embodiments of the present invention without departing from the scope of the invention. The first segments, second segments, intermediate segment, and other components of the device and/or system as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and systems may include more or fewer components or features than the embodiments as described and illustrated herein. For example, the components, features or aspects of FIGS. 1-6, FIG. 7, FIGS. 8 and 9, FIGS. 10 and 11, FIGS. 12-14, FIGS. 15-17, FIGS. 18-21, FIG. 22, FIGS. 25-34, FIGS. 35-42 and FIGS. 43-50 may all be used interchangeably and in alternative combinations as would be modified or altered by one of skill in the art. Accordingly, this detailed description of the currently-preferred embodiments is to be taken in an illustrative, as opposed to limiting of the invention.

Figure 51:
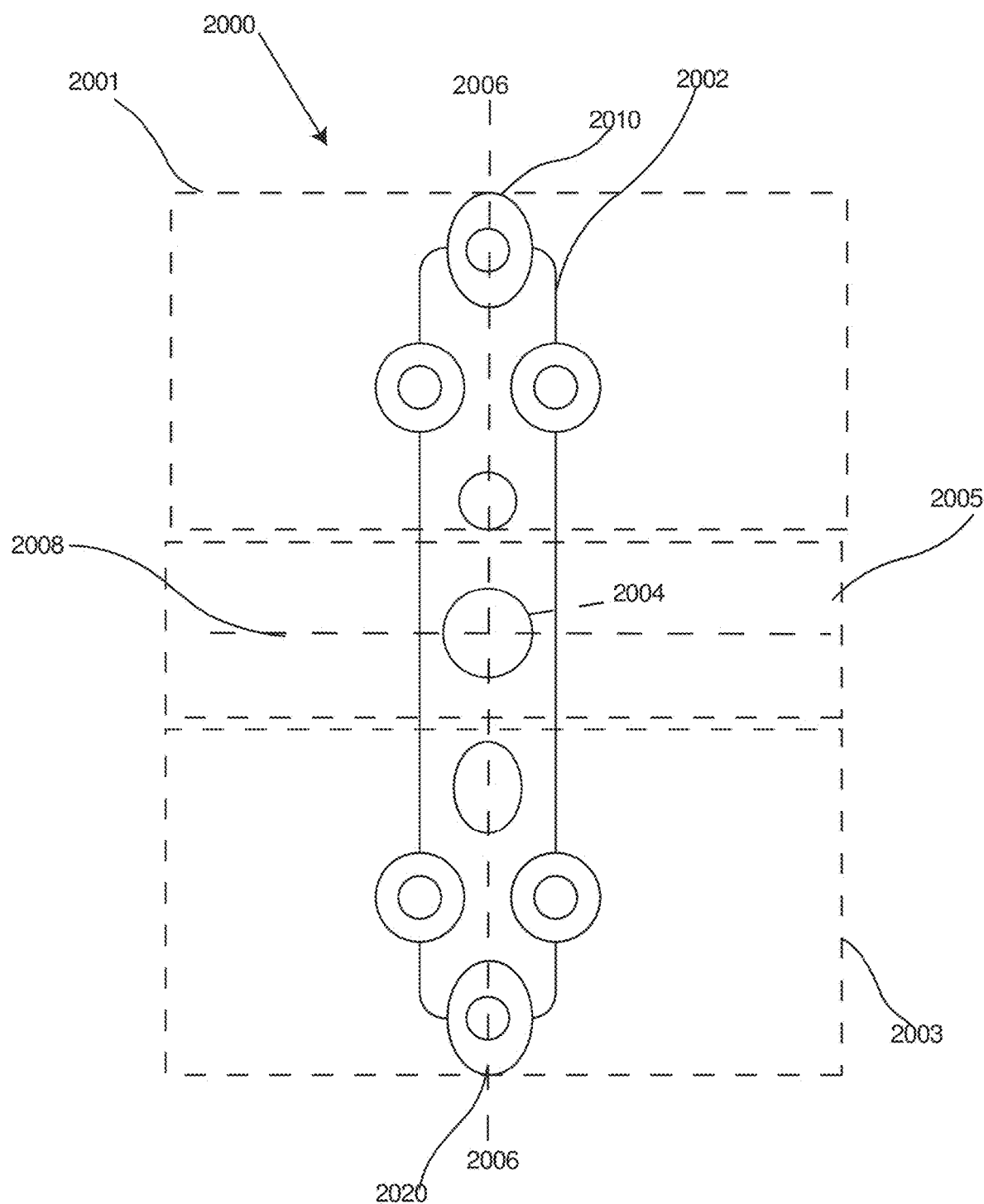
FIG. 51 is a top view of another embodiment shown in schematic form.

Turning to another embodiment, FIG. 51 is a top view of another embodiment shown in schematic form. In this view, there is shown an additional embodiment of an implant 2000 which has a proximal region 2001 and a distal region 2003 for a plate 2002 of the implant 2000. There is a central hole or aperture 2004 disposed in a central region 2005 disposed between the proximal region 2001 and the distal region 2003. At the end of the proximal region 2001 is a proximal end 2010 and at the end of the distal region is the distal end 2020. A longitudinal axis 2006 bisects the plate 2002 along its longer extension or length and latitudinal axis 2008 extends transverse or perpendicular to the longitudinal axis and extends along the width of the implant or plate.

Figure 52:
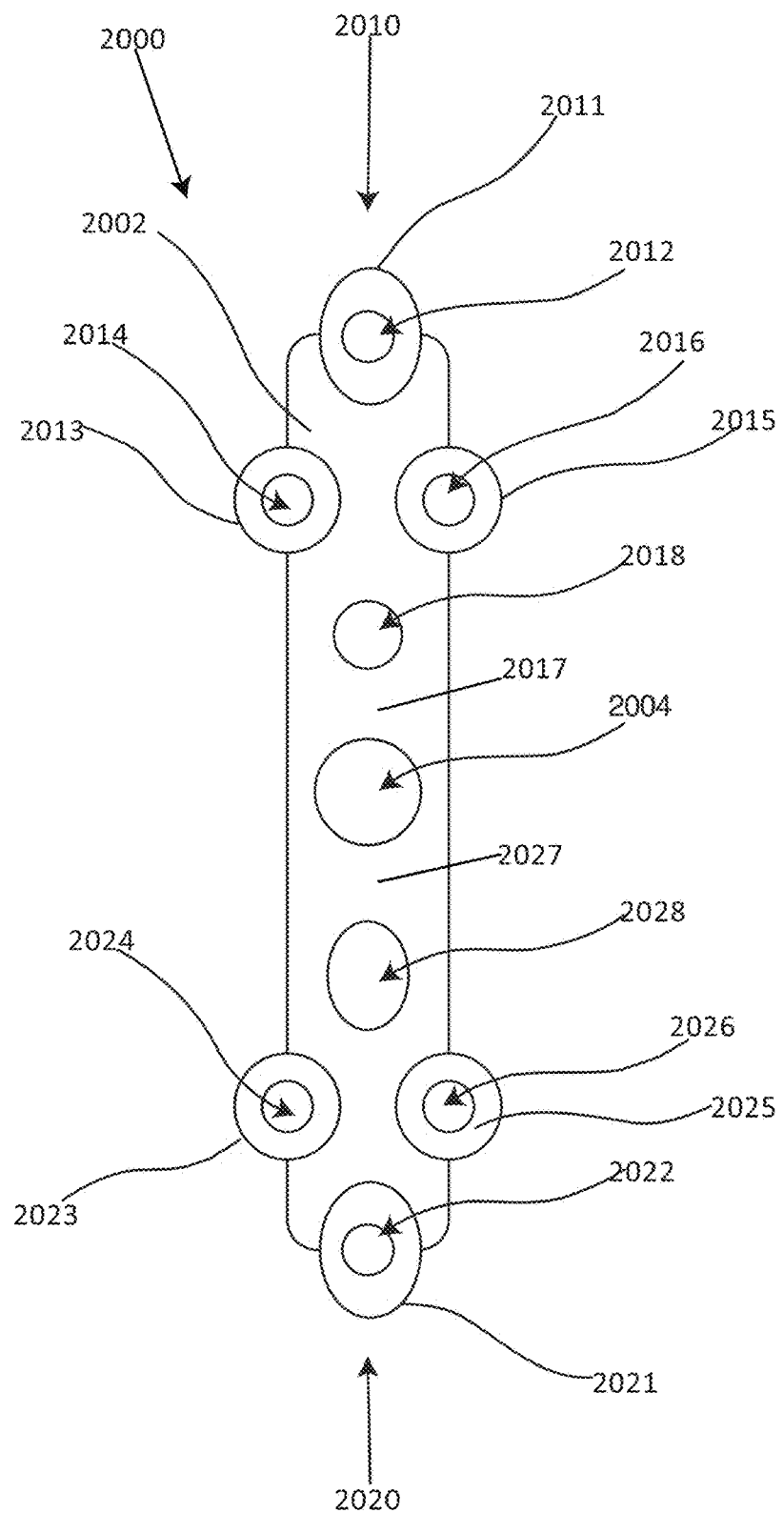
FIG. 52 is a top view of the embodiment shown in FIG. 51.

As shown in both FIGS. 51 and 52, disposed in the proximal region 2001 of the implant or plate 2002 are a plurality of apertures and extensions. For example, as shown in FIG. 52, there is an extension 2011 disposed at the proximal end 2010 of the plate 2002. Inside of this extension is an aperture 2012. In addition, there are at least two additional lateral extensions 2013, and 2015 each having respective apertures 2014, and 2016. There is also an inner region 2017 having an aperture 2018 disposed adjacent to the central region 2005 (See FIG. 51).

Figure 53:
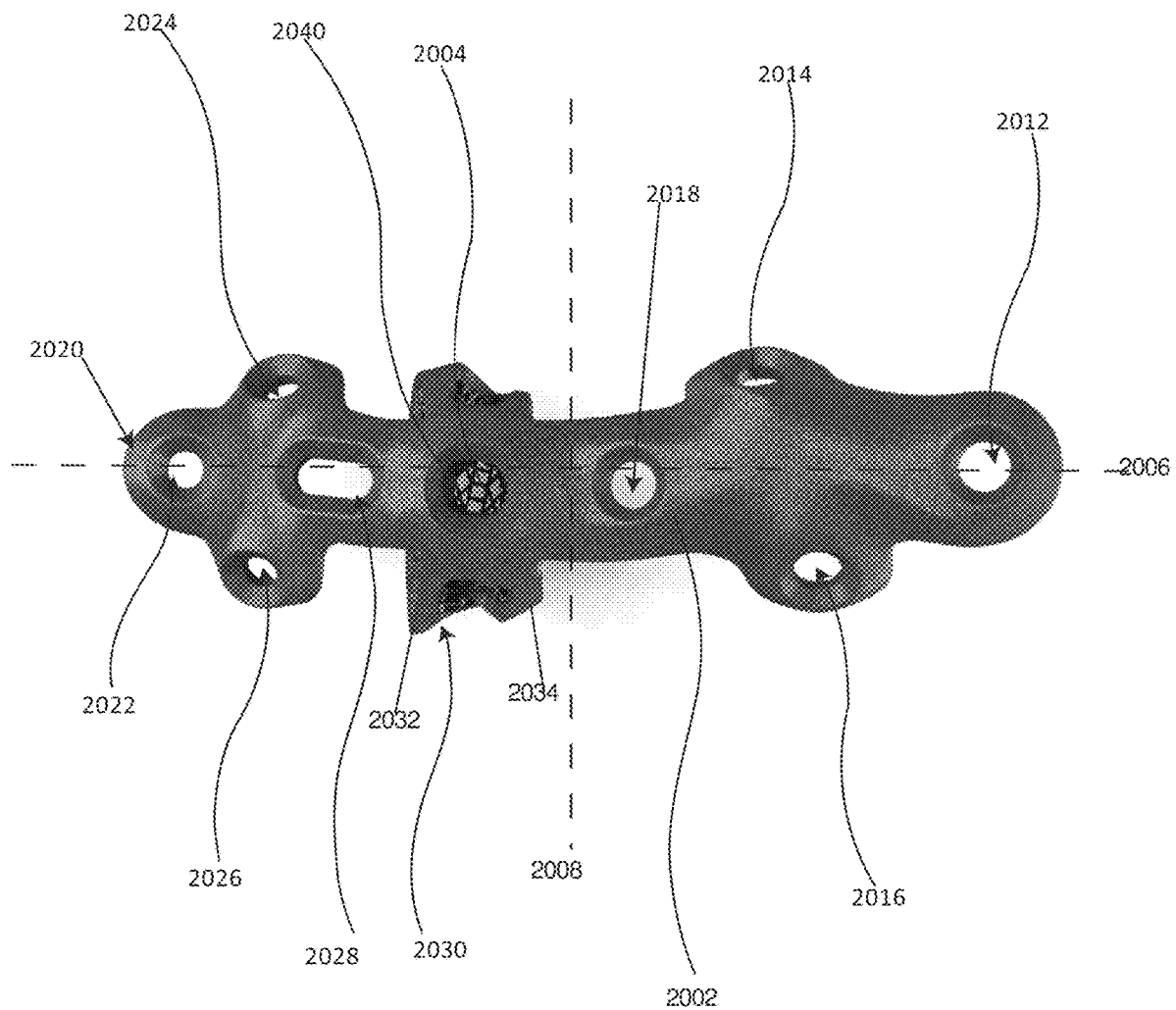
FIG. 53 is another top view of the embodiment shown in 3-D form.

The central region 2005 includes the central hole or aperture 2004 which is positioned adjacent to a porous section 2040 (see FIG. 53). In at least one embodiment this aperture 2004 can line up with an inner aperture on an adjacent wedge for receiving a fastener as well as for receiving biologic material to be fed into the wedge. The porous section 2040 either alone or in combination with a frame such as frame 2030, can also be referred to as a wedge segment or as a bridge segment. This porous section 2040 can be formed from a plurality of unit cells 2050 having a variable unit cell porosity (see FIG. 57). Unit cell porosity can be defined as the amount of material such as metal, plastic, composite or polymer vs. the amount of open space in a particular region. In at least one embodiment, such as that shown in FIG. 58, the unit cell porosity can be governed by the opening 2054.1 having a distance of dimension across a square shaped pattern 2053 of a honeycomb pattern of a unit cell 2050. This unit cell porosity is different than a material porosity which is essentially the inverse of material density. Thus, with respect to material porosity it is well understood that lead or iron is more dense (less material porosity) than aluminum because lead or iron have a greater weight per mass than aluminum. For purposes of this application when the term "porosity" is used alone, it means "unit cell porosity" while the term "density" alone means "unit cell density" or the amount of material over a defined volume or area vs. open area or volume occupied by voids.

The distal region 2003 of plate 2002 (See FIG. 51) also includes plurality of apertures and extensions. For example, there is an extension 2021 disposed at the distal end 2020 of the plate 2002. Inside of this extension is an aperture 2022. In addition, there are at least two additional lateral extensions 2023, and 2025 each having respective apertures 2024, and 2026. There is also an inner region 2027 having an aperture 2028 disposed adjacent to the central region 2005.

The aperture 2028 is shown as having a substantially oval shape while the other apertures are shown as having a substantially circular shape. Each of these apertures are shown as being countersunk holes having a beveled contour to allow a fastener such as a screw, a rivet or any other suitable fastener to be inserted therein. With the oval shape of the aperture 2028, this allows for some longitudinal adjustment of the plate when it is first being secured to an adjacent bone.

FIG. 53 is another top view of the embodiment shown in FIG. 51 in 3-D form. In this view, the plate 2002 is shown with longitudinal axis 2006 and latitudinal axis 2008. In this view, there is shown the central hole or aperture 2004 disposed in the central region (See FIG. 51) and which is also used to accommodate injection of a biologic material into the porous section 2040. There is also a frame 2030 which is configured add strength to in and around the porous section 2040 adjacent to the plate 2002. Frame 2030 includes a first frame 2032 and a second frame 2034 (See FIG. 54) spaced apart from each other and configured to bind or bound the porous section 2040. Frames 2032 and 2034 which make up the entire frame 2030 are also configured to maintain the structure of the porous section 2040 against any tension or compression forces as well. These frames 2032 and 2034 can be in at least one embodiment ring shaped. Central hole or aperture 2004 is configured to allow access to a central region of the porous section so that medical instruments can have access to the porous section and for the injection of a biologic material. This can be beneficial because it allows for biological material to be injected into a central region of the porous section 2040. In addition, in this view there is also shown the additional apertures 2012, 2014, 2016, 2018, 2022, 2024, 2026 and 2028 as well as the longitudinal axis 2006 and the latitudinal axis 2008.

Figure 54:
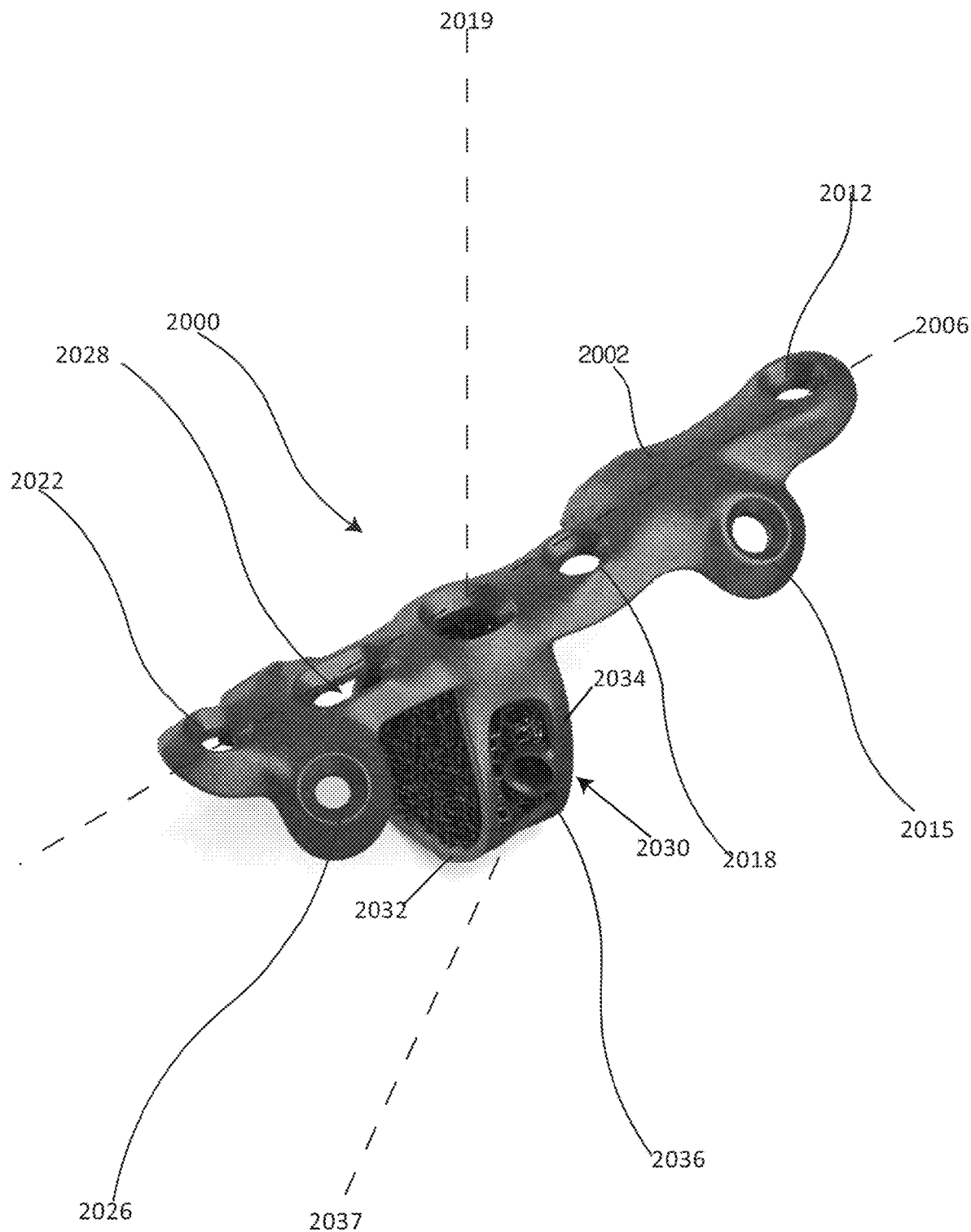
FIG. 54 is a top-distal-right perspective view of the embodiment shown in FIG. 53.

FIG. 54 is a top-distal-right perspective view of the embodiment which is a bone implant 2000 shown in FIG. 53. In this view, there is shown plate 2002 extending along longitudinal axis 2006 having apertures 2012, 2016, 2018, 2022, 2024, 2026, 2028, (See also FIG. 53) as well as a frame aperture 2036. Another frame aperture 2038 (See FIG. 66) is also present on the opposite side. As shown, there is an axis 2037 which shows that a fastener can extend in both a longitudinal dimension such as extending at least partially along longitudinal axis 2006 as well as in a latitudinal dimension such as extending at least partially along axis 2008 through frame aperture 2036 and through an aperture in the porous section 2040 to secure the implant and adjacent bone together in both a tension/compression manner along the longitudinal axis 2006 as well as in a torsion or lateral manner along the latitudinal axis 2008. In addition, the frame aperture 2036 as well as the frame aperture 2038 each extend between the first frame 2032 and the second frame 2034. This view also shows a transverse axis 2019 which extends transverse or perpendicular to the direction of the longitudinal axis 2006 and the latitudinal axis 2008. Both the plate such as plate 2002 as well as the porous architecture of the porous section 2040 can be formed from a material that has an outer surface that is either smooth, substantially smooth, rough or substantially rough.

Figure 55:
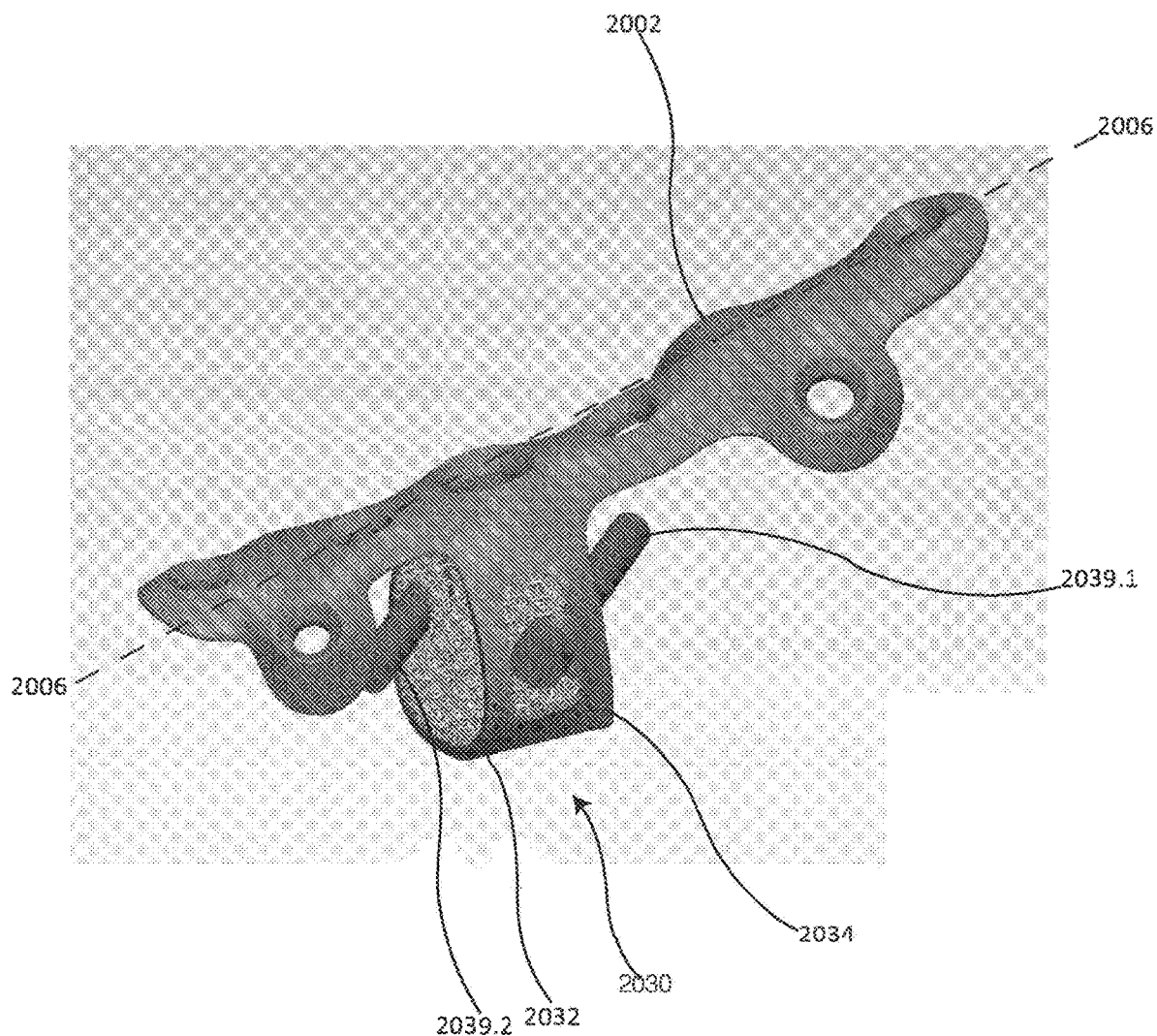
FIG. 55 is a top-right perspective view of the embodiment shown in FIG. 53.

FIG. 55 is a top-right perspective view of the embodiment shown in FIG. 53. In this view, there is shown a longitudinal axis 2006 for plate 2002. Two fasteners 2039.1 and 2039.2 are shown extending through the frame apertures 2038 and 2036 respectively as well as through the porous section 2040. These fasteners 2039.1 and 2039.2 extend as described above in both a longitudinal dimension and a latitudinal dimension.

Figure 56:
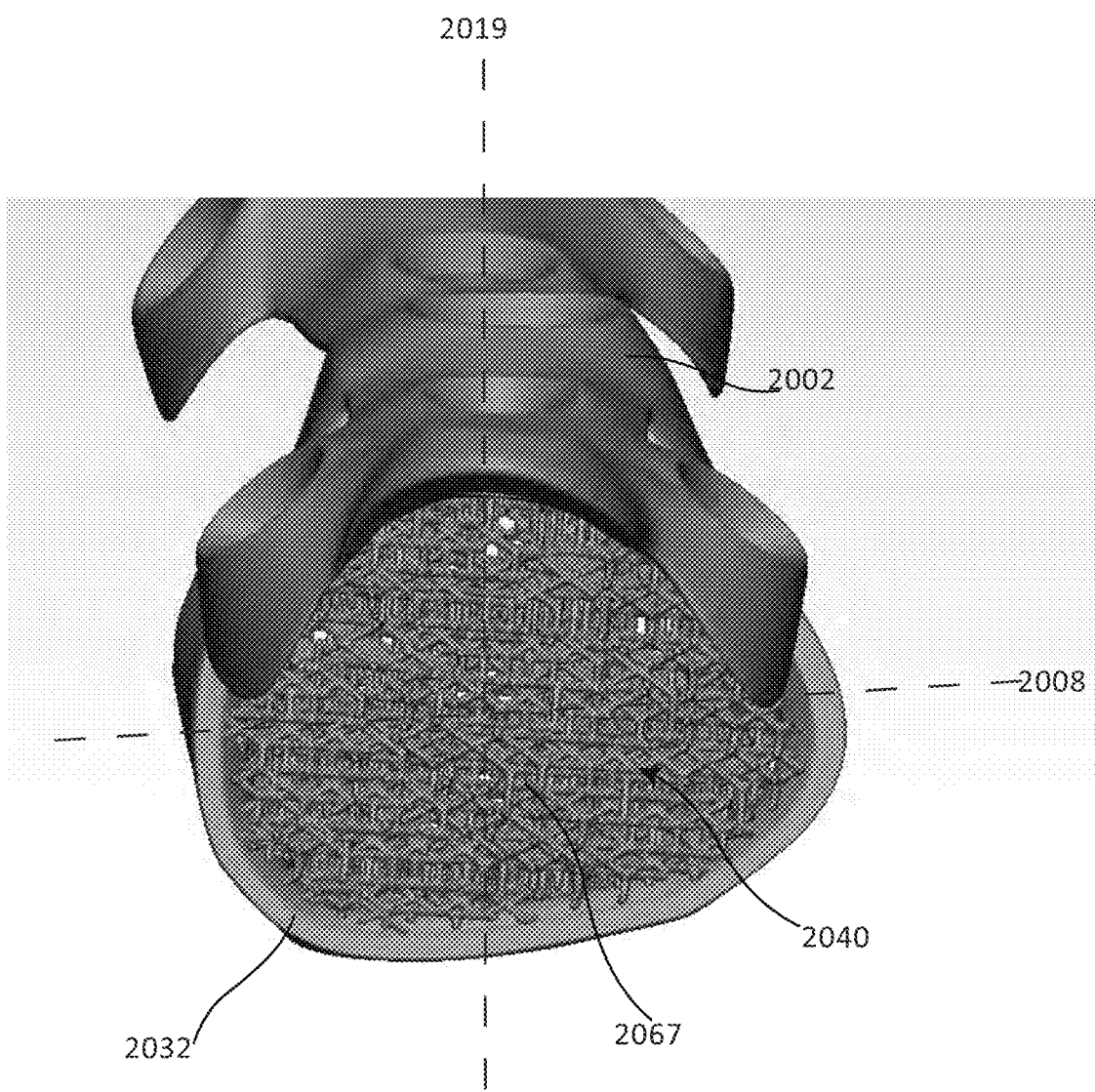
FIG. 56 is a cross-sectional view of the embodiment shown in FIG. 53 taken along the latitudinal line.

FIG. 56 is a cross-sectional view of the embodiment shown in FIG. 53 taken along the latitudinal line 2008. In this view, there is a porous section 2040 which is shown as a lattice formed in a pattern of structural members forming individual unit cells such as unit cell 2050 of FIG. 57 or other shaped unit cells shown in FIGS. 60A, 60B, 61A and 61B and 62. This porous section 2040 is coupled to the plate in any suitable manner such as via the frame 2030. Alternatively, or in addition, the porous section 2040 which comprises a lattice structure can be formed integral, with methods such as additive manufacturing with plate 2002 as well. This porous section 2040 is bound by frame member 2032 and has a first side outer face 2067 positioned facing the distal end 2003 (See FIG. 51).

Figure 57:
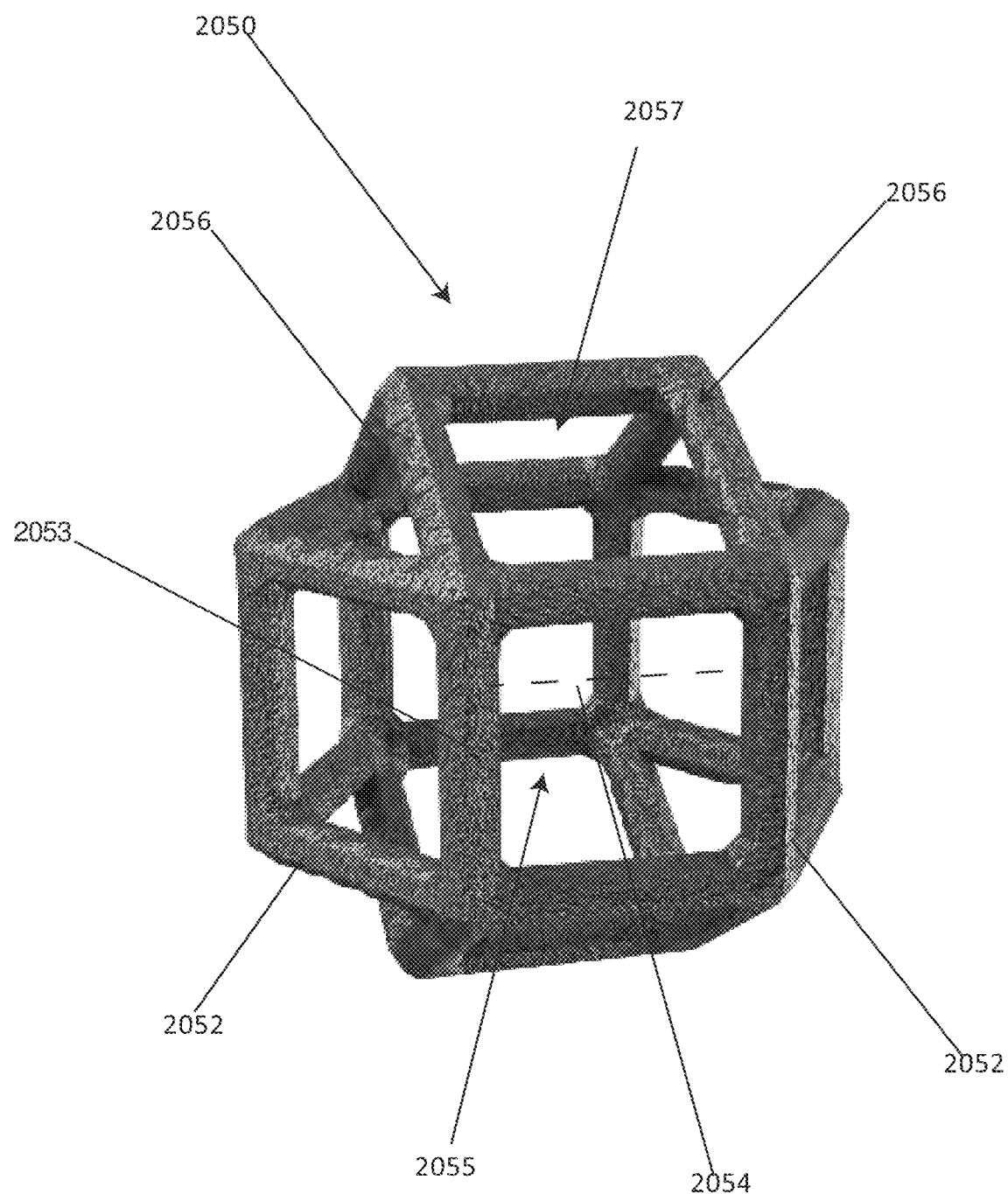
FIG. 57 is a front view of a structural member which can be used with the embodiment of FIG. 53.

FIG. 57 is a front view of a unit cell which can be used with the embodiment of FIG. 53. In this embodiment, this pattern, or unit cell 2050 forming a porous architecture is in the form of a honeycomb which is formed from structural members or supports 2052 comprising struts or supports and which includes at least one square shaped pattern 2053 having an opening shown by dotted line showing an opening 2054.1 having a distance or dimension forming an opening to a central cubical portion 2055. There is also an exterior triangular pattern 2056 forming lattice elements 2057 formed by a plurality of different structural members or supports 2052. Each of these unit cells 2050 can be joined to an adjacent unit cell 2050 through a common structural member or support 2052.

As discussed above, however, the porous architecture may be in a substantially uniform or consistent pattern or a variable pattern, with at least one pattern being at least one of honeycomb, diamond, square or any other suitable shape for each cell. In addition, the porosity of these patterns could be consistent or variable depending on the need. Furthermore, the individual parts of the porous architecture, that of the individual struts can in at least one embodiment have an exterior surface that is smooth. In another embodiment the porous architecture is made from a material such that the individual struts are substantially smooth. In another embodiment, the porous architecture has struts that are made from a material that has an exterior surface that is roughened. In another embodiment, the porous architecture is made from struts having an exterior surface that is substantially roughened.

Figure 58:
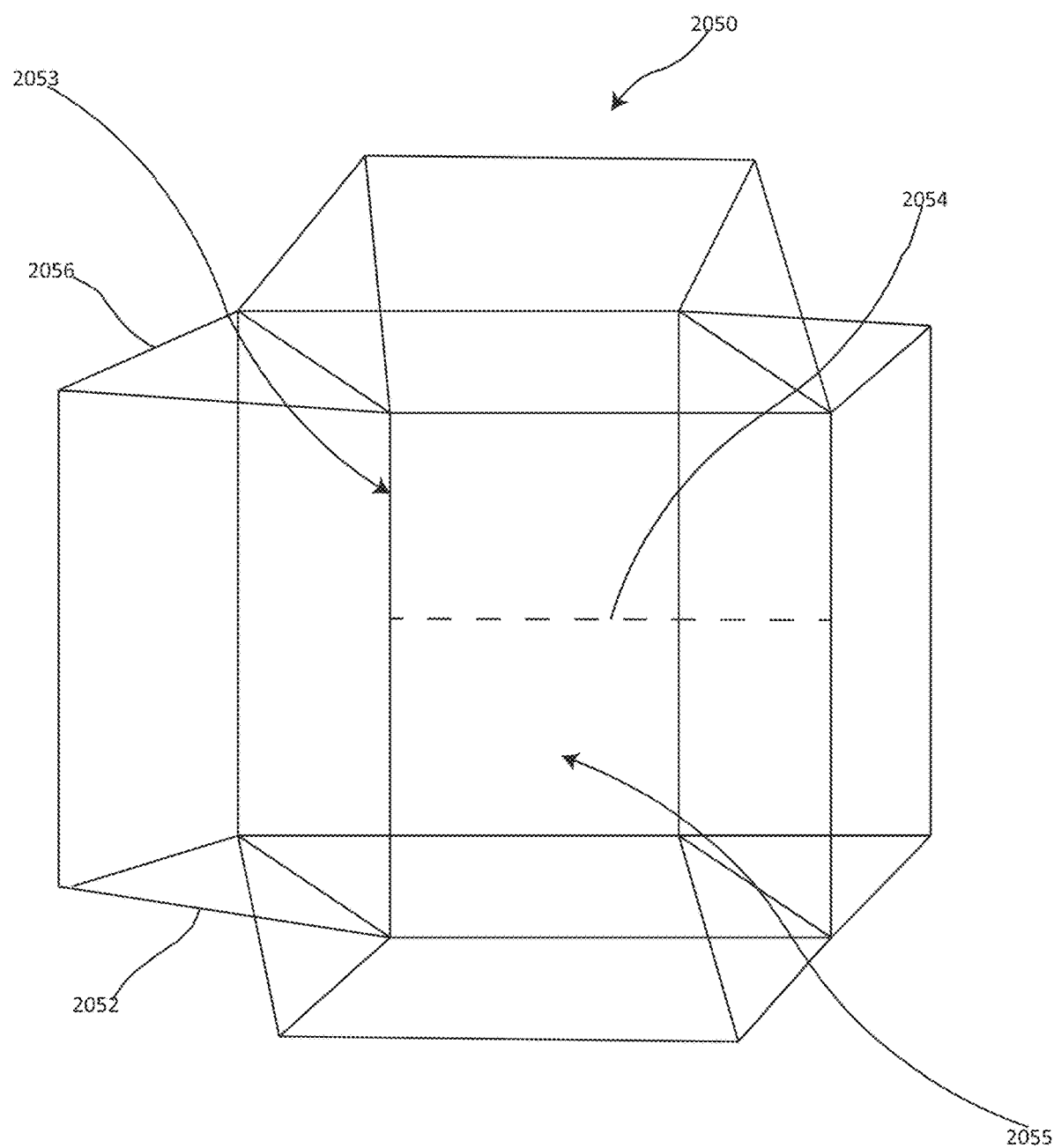
FIG. 58 is a wire frame view of the structural member shown in FIG. 57.

FIG. 58 shows a wire frame version of the embodiment shown in FIG. 57. In this view, there is shown an opening 2054 which is essentially the opening formed on the square shaped pattern 2053. This pore or opening 2054 can be varied in dimension such that it changes in dimension, such as via a 1.5 mm opening or even up to a 2.5 mm opening in one example. Other examples can include a dimensional range of 0.5 mm to 5 mm. In addition, in even other embodiments other ranges are possible as well as described below.

Figure 59:
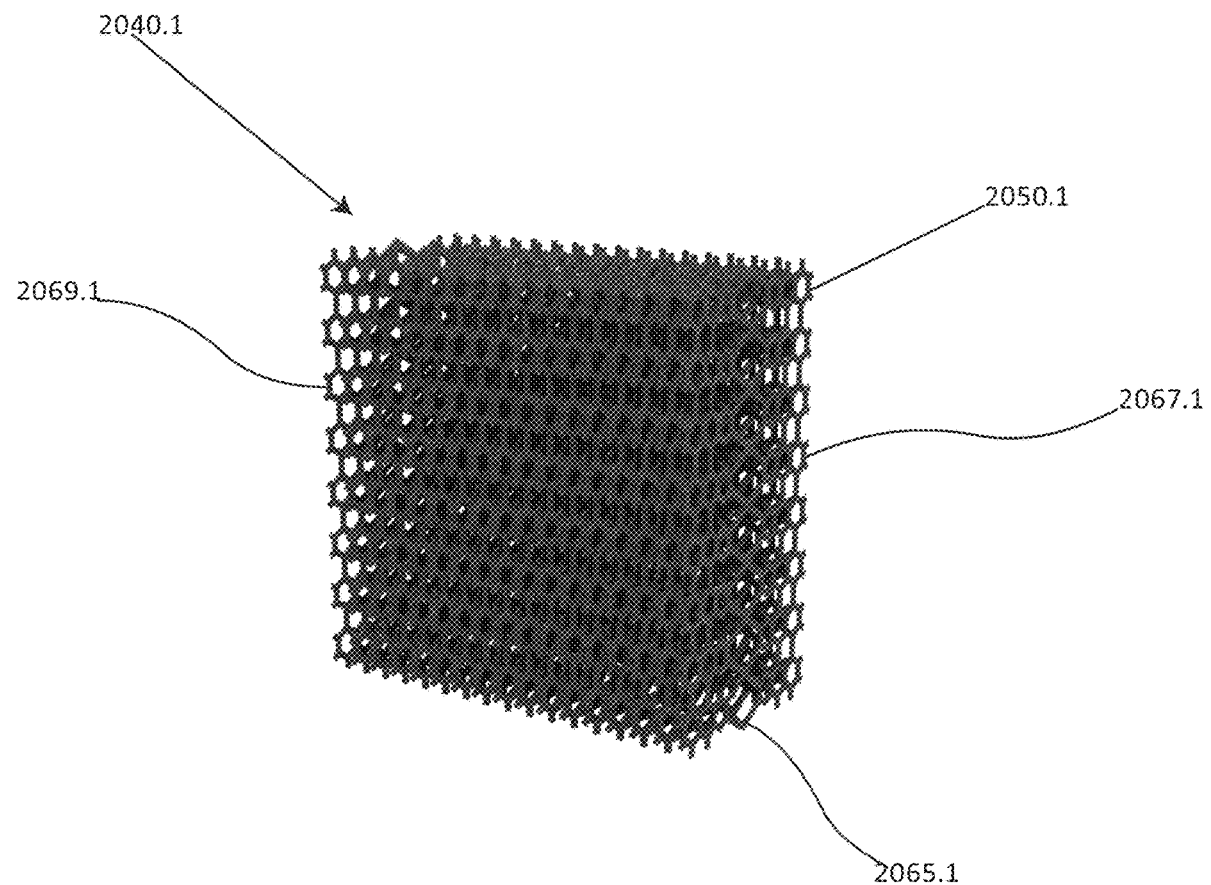
FIG. 59 is a side perspective view of a porous section.

FIG. 59 is a side perspective view of a porous section 2040.1 which has a first side 2067.1 which is facing a distal end and a second side 2069.1 which facing a proximal end, and a middle region 2065.1. This porous section includes unit cells 2050.1 which can be configured in a honeycomb pattern or in a different pattern than a honeycomb pattern. Rather the cross-sectional shape of this pattern is substantially hexagonal in shape and has an opening 2054.1 which can be varied in dimensions.

Figure 60A:
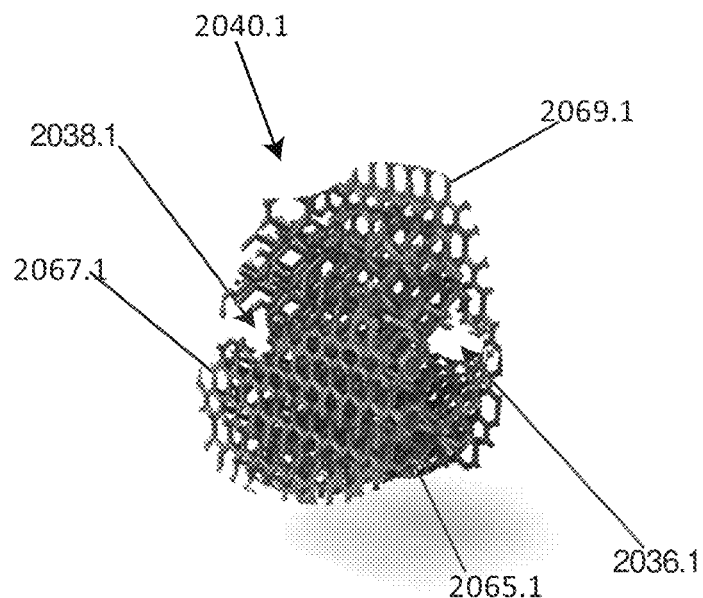
FIG. 60A is a side perspective view of another porous section.

FIG. 60A is a side perspective view of another embodiment of a porous region 2040.1 which includes a first side 2067.1 which is facing a distal end and a second side 2069.1 which is facing a proximal end and a middle region 2065.1. Pre-set apertures 2036.1 and 2038.1 are formed in the porous region and are configured to receive fasteners as well such as fasteners 2039.1 and 2039.2 respectively. These apertures 2036.1 and 2038.1 are configured to line up with respective frame apertures 2036 and 2038. These apertures 2036.1 and 2038.1 can be formed by an additive printing method or via a simple boring technique prior to installation.

Figure 60B:
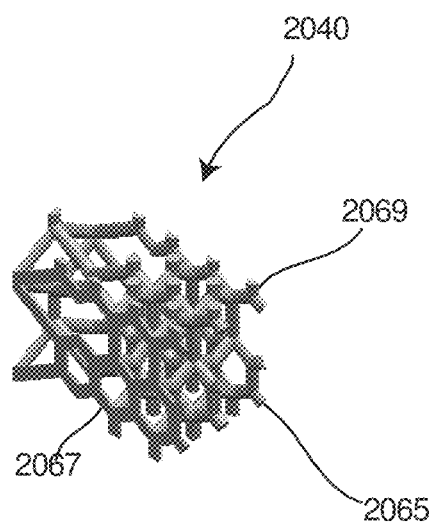
FIG. 60B is a side perspective view of a portion of a porous section.

FIG. 60B shows a section of this porous region 2040 which includes a first side outer face 2067 and a second side outer face 2069. This view shows the honeycomb pattern shown in FIGS. 57 and 58.

Figure 61A:
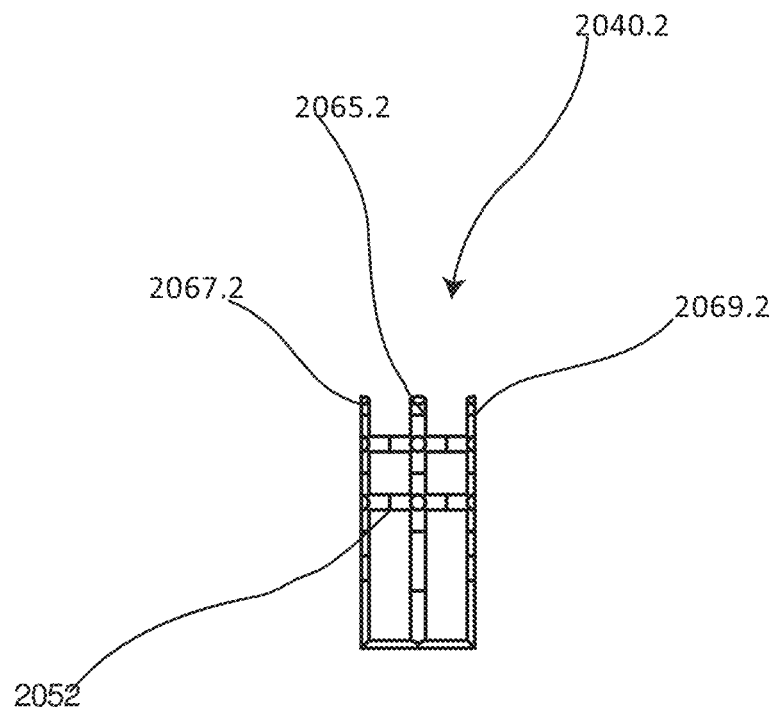
FIG. 61A is a side cross-sectional view of a porous section.

FIG. 61A shows side cross-sectional views of the porous section. In this view, there is a first side 2067.2, a second side 2069.2, and a central region 2065.2. Essentially in at least one embodiment these sides 2067.2 and 2069.2 or central region 2065.2 can form different layers. The central region 2065.2 is bound together with the first side and the second side via structural members or supports 2052. As indicated above, as well as below, the porosity (unit cell porosity) on the external sides such as on sides 2067.2 and 2069.2 can be different than the porosity of the central region.

Figure 61B:
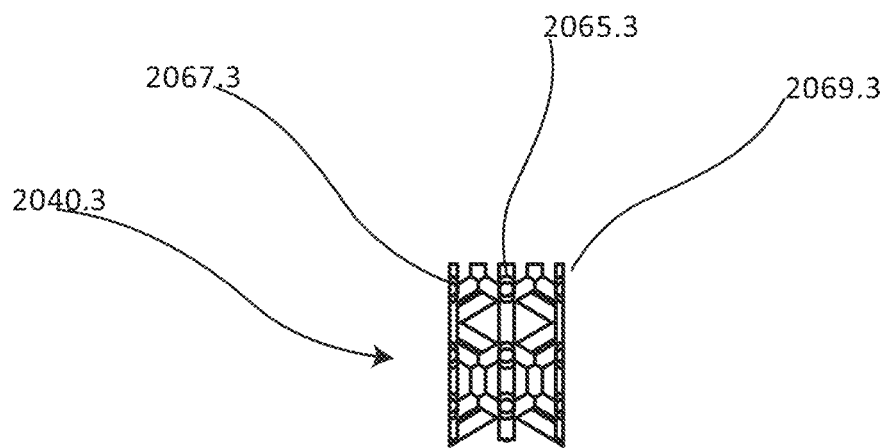
FIG. 61B is a side cross-sectional view of another embodiment of a porous section.

FIG. 61B is a side view of another porous section. For example, there is a first side 2067.3 and a second side 2069.3 and a central region 2065.3. As indicated above, the porosity of the first side 2067.3 and the second side 2069.3 can be different than the porosity of the central region 2065.3. In particular, in at least one embodiment the porosity of the first side 2067.3 and the second side 2069.3 can be lower than the porosity in the central region 2065.3.

Figure 62:
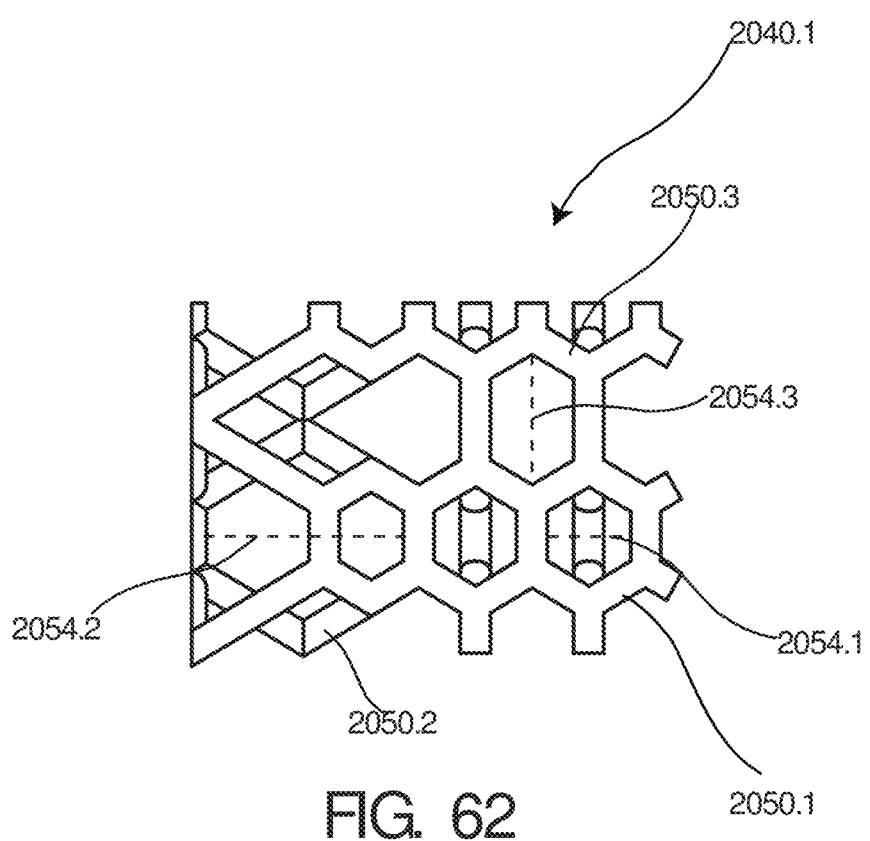
FIG. 62 is a view of a portion of a porous section.

FIG. 62 shows a side view of another embodiment of a porous region 2040.1 having a plurality of different unit cells 2050.1, 2050.2, and 2050.3 each having different dimensioned openings 2054.1, 2054.2, and 2054.3. In this view the unit cells are shown as having different apertures or openings forming a different unit cell porosity. For example, unit cell 2050.1 has a smaller porous opening 2054.1 than that of unit cell 2050.3 which has a porous opening 2054.3, while unit cell 2050.2 has a large porous opening 2054.2 than that of opening 2054.3 of cell 2050.3. Thus, with this design the porosity can be varied based both on depth moving from a distal face or a proximal face towards an interior region, or the porosity can even vary depending on the location on a face as well so that even at a same depth along the porous section, there can be different unit cells having different porosities.

Figure 63:
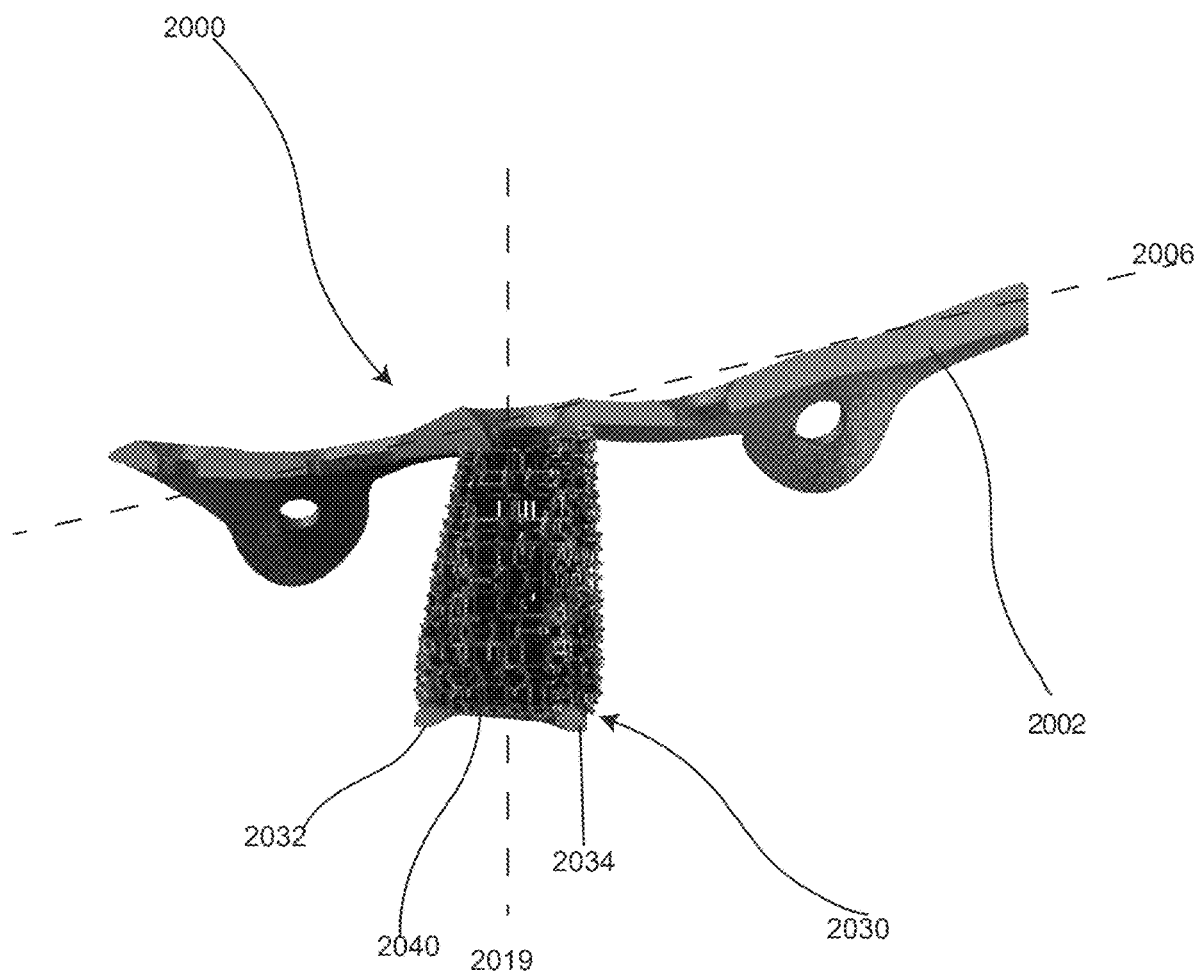
FIG. 63 is a side cross sectional view of the embodiment shown in FIG. 53 taken along the longitudinal line.

FIG. 63 is a side cross sectional view of the embodiment shown in FIG. 53 taken along the longitudinal axis 2006. In this view, it shows the porous section 2040 coupled to plate 2002. The embodiments of the unit cells shown in FIGS. 1-50, FIGS. 59-62 as well as with the embodiments of 71-75 can also be used in place of the porous section 2040 as well.

Porous section 2040 which essentially forms a wedge normally sits in frames 2032 and 2034 of frame 2030. In at least one embodiment, porous section 2040 can be formed without a frame. In addition, in at least one embodiment, porous section 2040 has a varying porosity or density wherein at the exterior regions adjacent to either the distal region or the proximal region the porous section is more dense or less porous. In an interior region, the porous section is less dense or more porous. This varying density or porosity is created by varying the average size of the pores or openings created by the struts of the honeycomb pattern shown in FIG. 57 and FIG. 58, or in the design shown in FIGS. 59-62, For example, the size of each square opening 2054.1 (See FIG. 62) can be varied from 1.5 mm to 2.5 mm depending on the desired porosity. Other parameters could also be used such as a range between 1 mm and 3 mm for units or holes created by the square cross sections. The following could be other parameters: substantially 0.5 mm to 5 mm, substantially 1 mm to 5 mm, substantially 2 mm to 5 mm, substantially 3 mm to 5 mm, substantially 4 mm to 5 mm, substantially 1 mm to 4 mm, substantially 2 mm to 4 mm, substantially 3 mm to 4 mm, substantially 3 mm to 5 mm, substantially 4 mm to 5 mm.

The design of the lattice structure is configured so that it is to optimize strength for bending and torsion as well as for osteosynthesis. For example, the more dense the lattice structure, the stronger and more resilient it would be for purposes of bending and torsion stresses as well as compression and tension. In addition, the less dense the lattice structure the more open it is for bone growth or osteosynthesis. The porosity of on the outer faces of the porous section which interface with a broken bone is lower so that these outer faces have greater material surface area and smaller pores to interact with bone cells to signal osteosynthesis.

Figure 64:
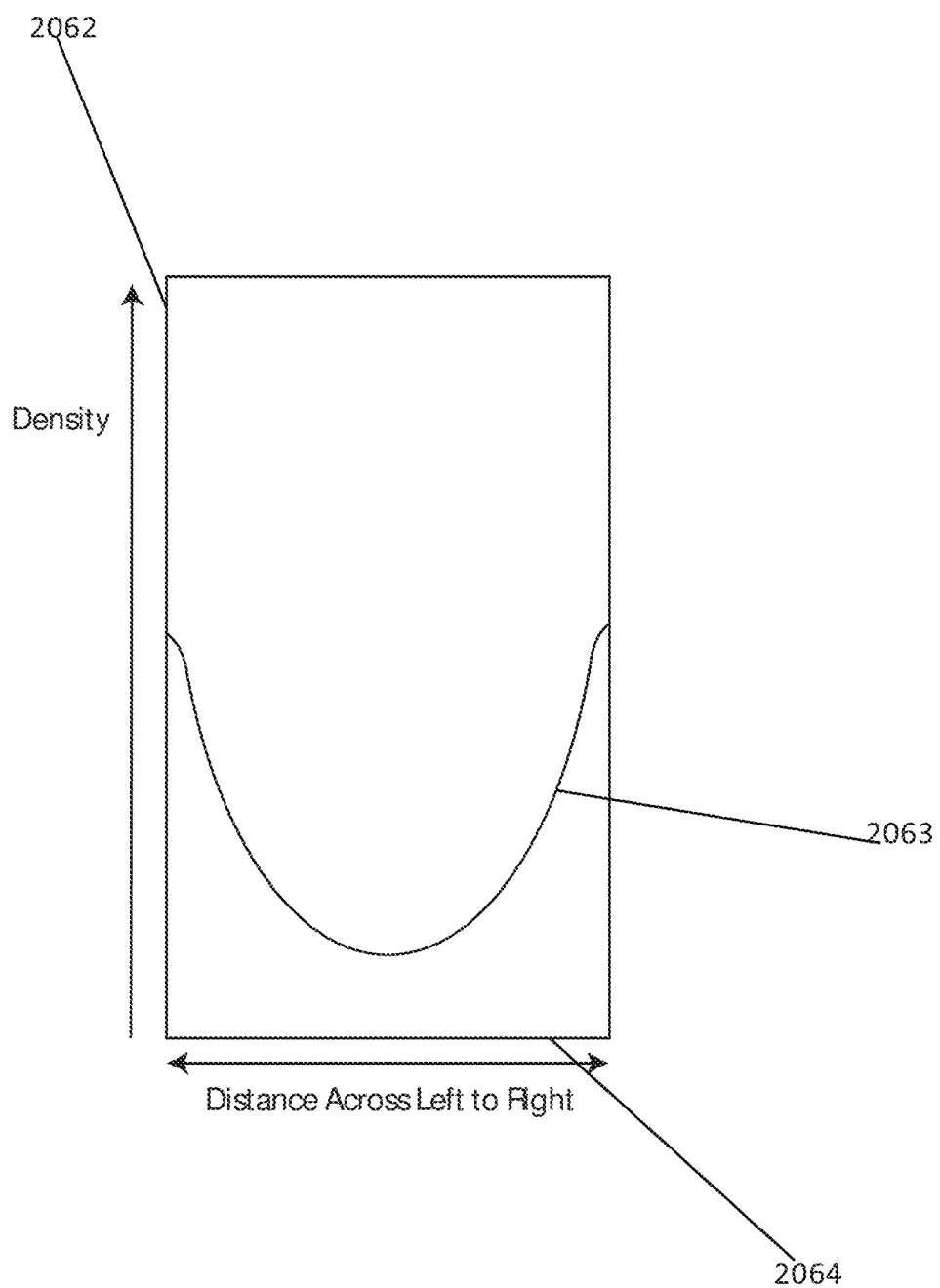
FIG. 64 is a graph showing the reduction in density for the porous section.

FIG. 64 is a graph showing the change in density for the porous section along the longitudinal axis 2006 such as from a distal region adjacent to the distal region 2003 of the plate 2002 to a proximal region adjacent to the proximal region 2001 of plate 2002 (See FIGS. 51, 59 and 61). The two axes are shown as a Y axis which tracks the level of density and an X axis which is the distance along the longitudinal axis 2006 starting from either the proximal region of the porous section, to the distal region of the porous section or vice versa. While no absolute overall values are given based upon the overall changes in size of the pores or holes, the change in porosity or density could be between 5-90% in at least one embodiment or between 1-75% in at least another embodiment. In another embodiment, the change in density could be 30%, while in other embodiments the change in density could be any one of substantially 20%, 30%, 40%, 50%, 60%, 70%, or 80%. These differences in density can be customized based upon the location of the device being implanted as well as the thickness of the bone, the bone structure adjacent to the implant, the movement and loading conditions as well. In at least one embodiment a porous section or wedge can have an opposite density profile with the pores or holes being larger on the outer surface(s) and smaller towards a center region of the wedge.

Figure 65:
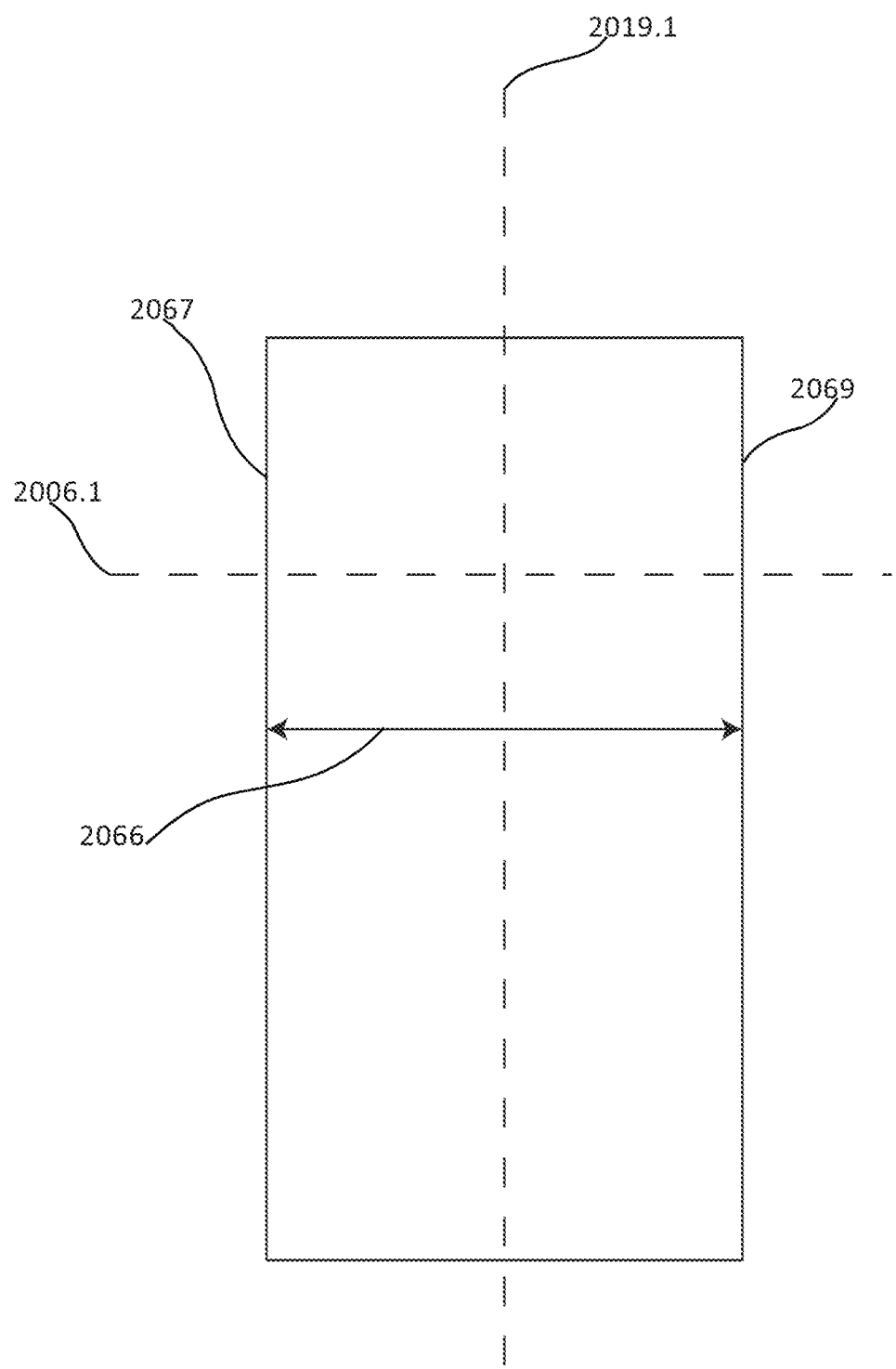
FIG. 65 is a side view of the porous section having a longitudinal extension and a latitudinal extension.

FIG. 65 is a representative side view of the porous section having a longitudinal extension and a latitudinal extension. This representative side view is shown as having a distal end or first side outer face 2067 and a proximal end or second side outer face 2069 extending along a density or porosity profile 2066 along a longitudinal axis 2006.1 which is the same or substantially similar to longitudinal axis 2006. This density or porosity profile is the same as the X axis in FIG. 64. As indicated above, distal end outer face 2067 is adjacent to distal region 2003, while proximal end is adjacent to proximal region 2001 shown in FIG. 51.

Figure 66:
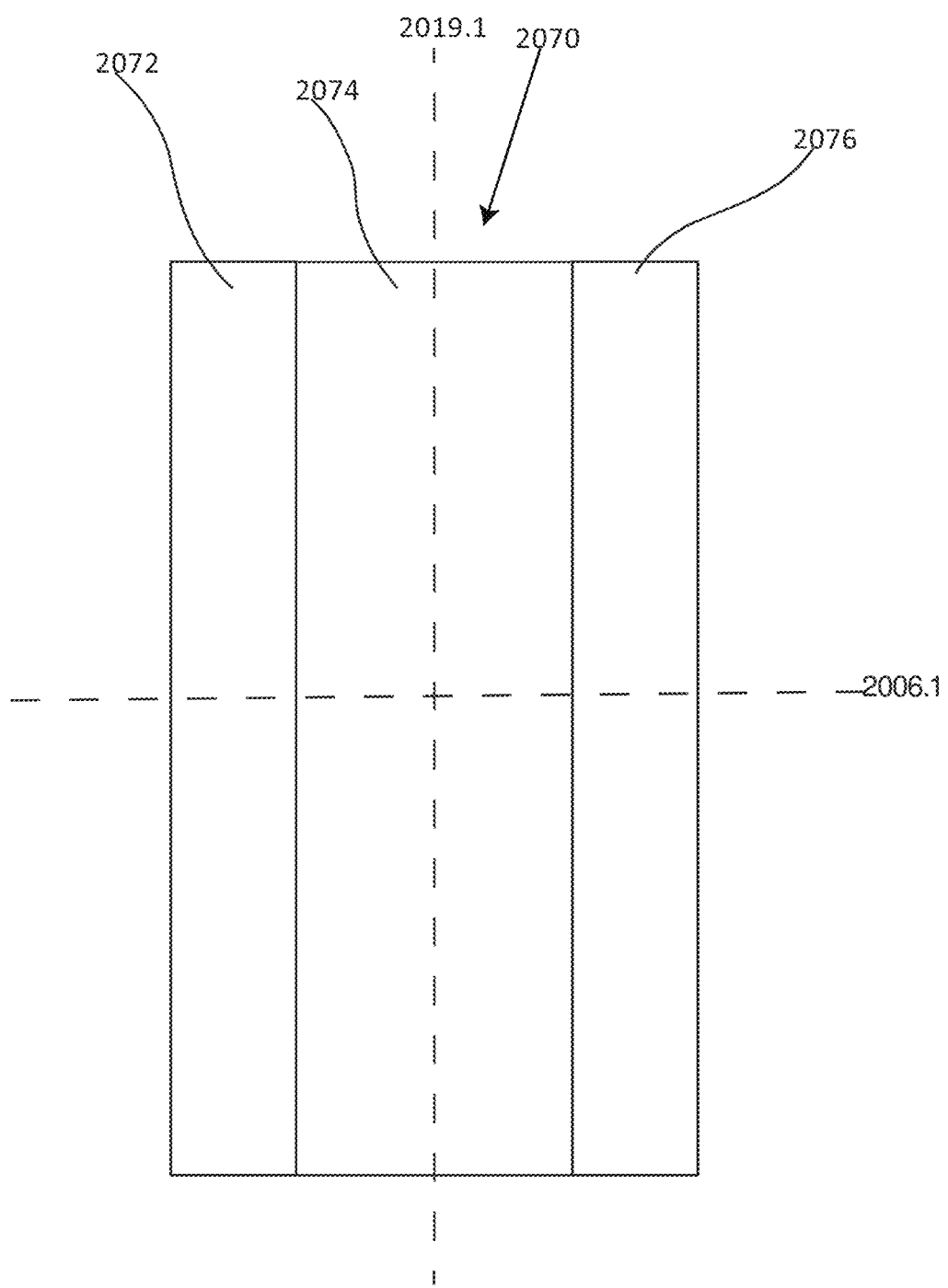
FIG. 66 is a side view of another embodiment of a porous section having different layers.

FIG. 66 is a side view of another embodiment of a porous section having different layers. For example, rather than having a gradual change in porosity or density along an extension of the porous section such as that shown in FIGS. 64 and 65, the porous section can have distinct regions of differing porosity such as a first region or layer 2072, a second region or layer 2074 and a third region or layer 2076. With this layered design, different layers can be printed or created separately and then put together in a layered porous section. In at least one embodiment, the porosity of layers 2072 and 2076 can be lower than the porosity of region or layer 2074.

Figure 67:
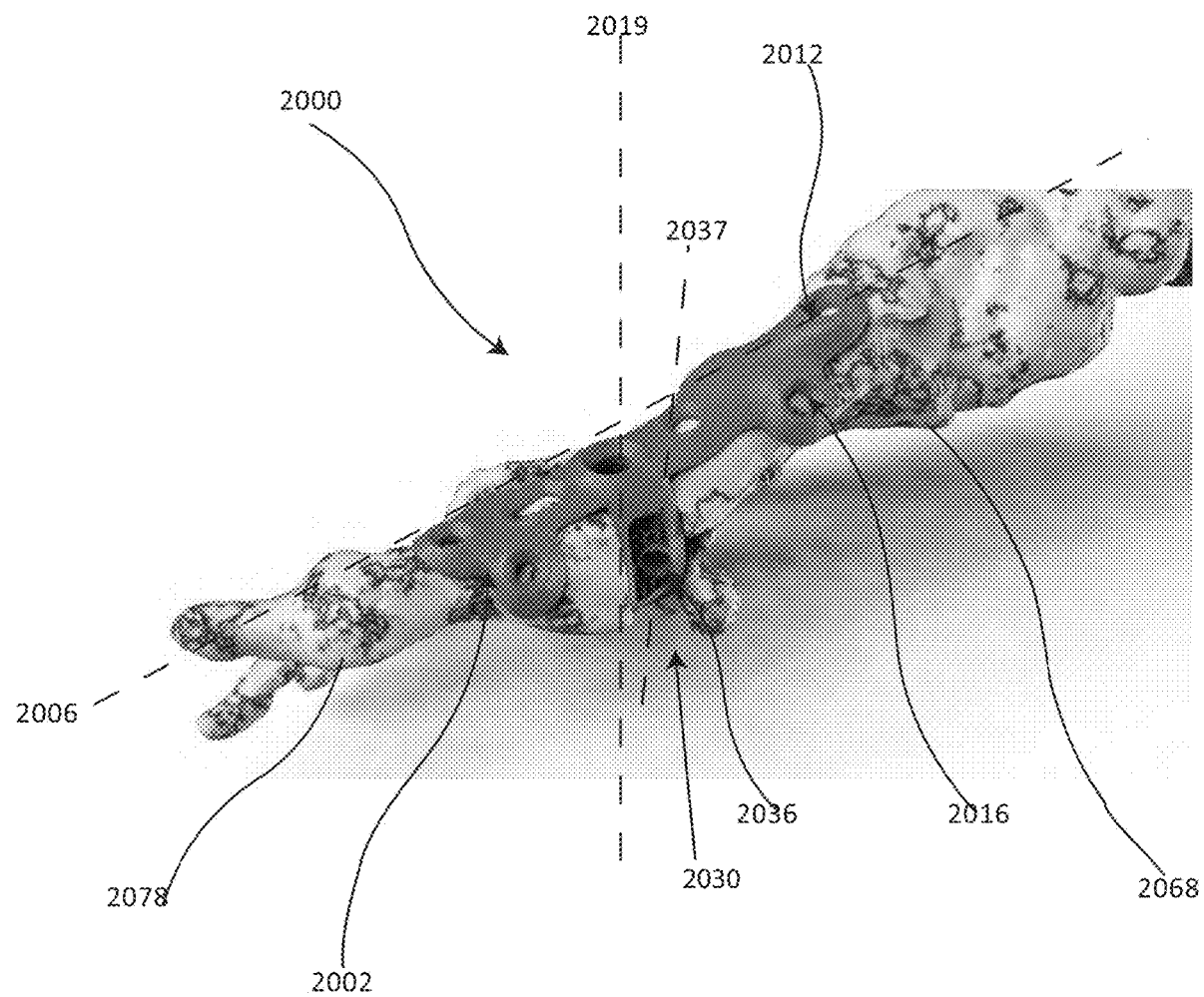
FIG. 67 is a top perspective view of the embodiment shown in FIG. 53

FIG. 67 is a top perspective view of the implant embodiment 2000 shown in FIG. 53. With this design, there is shown plate 2002 extending along longitudinal axis 2006 which is coupled to bone 2068 via one portion and to bone 2078 via another portion. Disposed between these two bones is frame 2030 (See FIG. 63). With this design, each of the apertures such as aperture 2012 or frame aperture 2036, can be lined up so that fasteners can be used to secure this plate 2002 to the respective bones 2068, and 2078. As shown, frame aperture 2036 is configured to allow a fastener to extend along axis 2037 in both a longitudinal and latitudinal direction which is transverse to transverse axis 2019. Thus, frame 2030, and porous section 2040 sit between bones 2068 and 2078 wherein when the implant is fastened to these bones 2068, and 2078 it stabilizes these bones together via a compression force caused by the respective fasteners. Thus, each of the apertures 2012, 2014, 2016, 2018, 2022, 2024, 2026, 2028, 2036, and 2038 (See FIGS. 52, and 54) are configured to receive respective fasteners which secure both the plate 2002 to the respective bones as well as the frame 2030 to the respective bones thereby holding these bones 2068 and 2078 together in a stabilized manner to allow then to compress together and heal.

Figure 68:
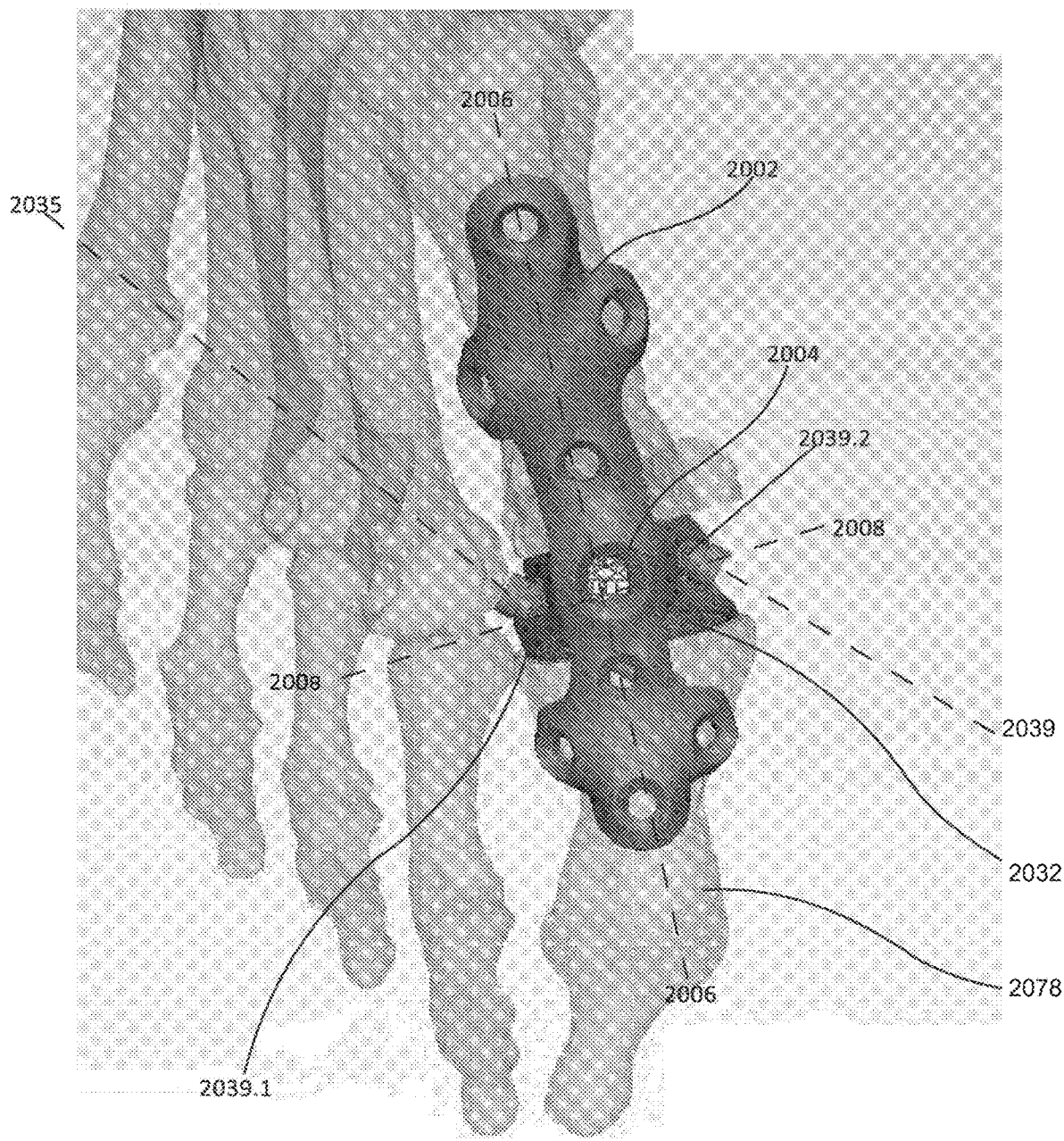
FIG. 68 is a top perspective view of the embodiment shown in FIG. 53 implanted on bone.

FIG. 68 is a top perspective view of the embodiment shown in FIG. 53 implanted on bone. For example, there is plate 2002, extending along longitudinal axis 2006 which is secured to bone via fasteners 2039.1 and 2039.2 along axis lines 2035 and 2037. As shown, axis lines 2035 and 2037 extend along both the longitudinal axis 2006 and the latitudinal axis 2008 so that there is simultaneous tension/compression securement along the longitudinal axis as well as fixation or securement along the latitudinal axis 2008. This multi-dimensional extension allows for securement or fixation against torsion, rotational movement or any other type of movement which may result in the tearing away of the porous section 2040 from a bone interface while the patient is healing. The fasteners 2039.1 and 2039.2 are configured to clamp to the frame and then create compression along the joint so as to assist in having the two separated bones fuse together. The lattice can be formed in an optimal way so as to have a pre-set void in the region that the fasteners pass through.

Figure 69:
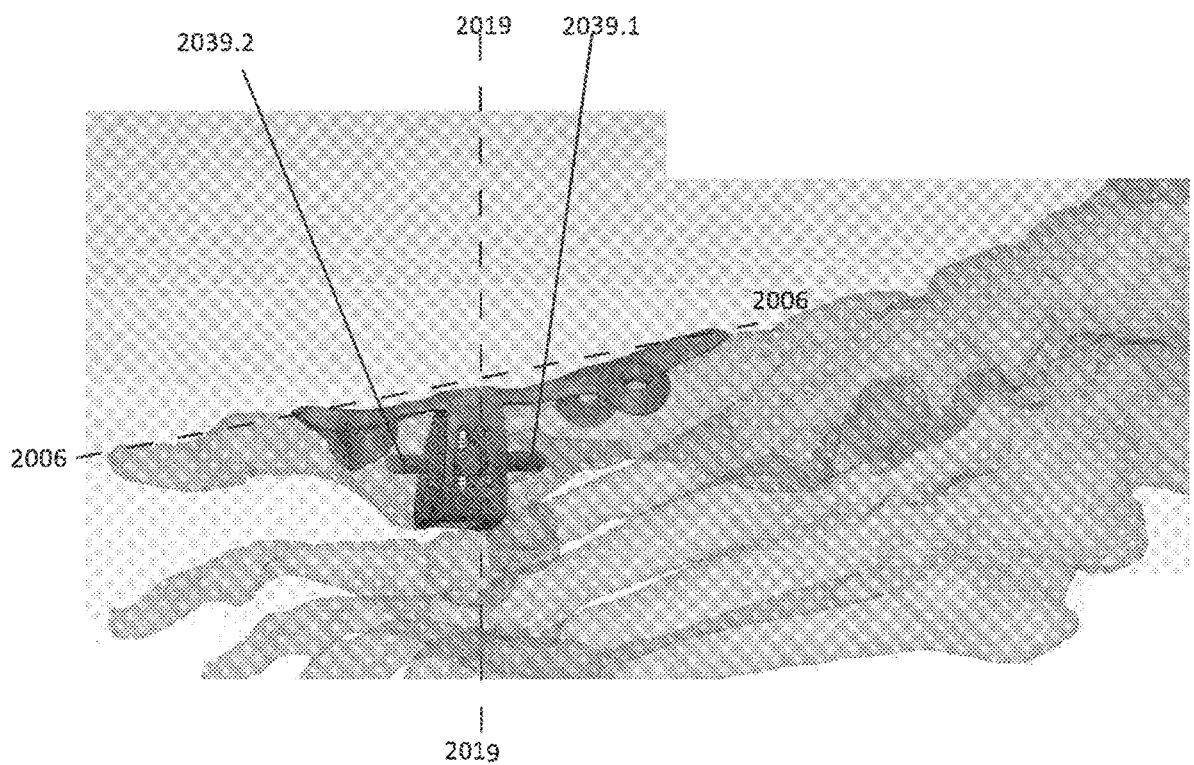
FIG. 69 is a side view of the embodiment of FIG. 53 implanted on bone.

FIG. 69 is a side view of the embodiment of FIG. 53 implanted on bone. In this view there is shown fasteners 2039.1 and 2039.2 extending in their respective axes while the plate extends along longitudinal axis 2006. Transverse axis 2019 extends transverse to longitudinal axis 2006 and in this case, the securing of the bones together with the porous section in between and the fasteners 2039.1 and 2039.2 prevents any rotation around transverse axis 2019 thereby harming any healing bone.

Figure 70:
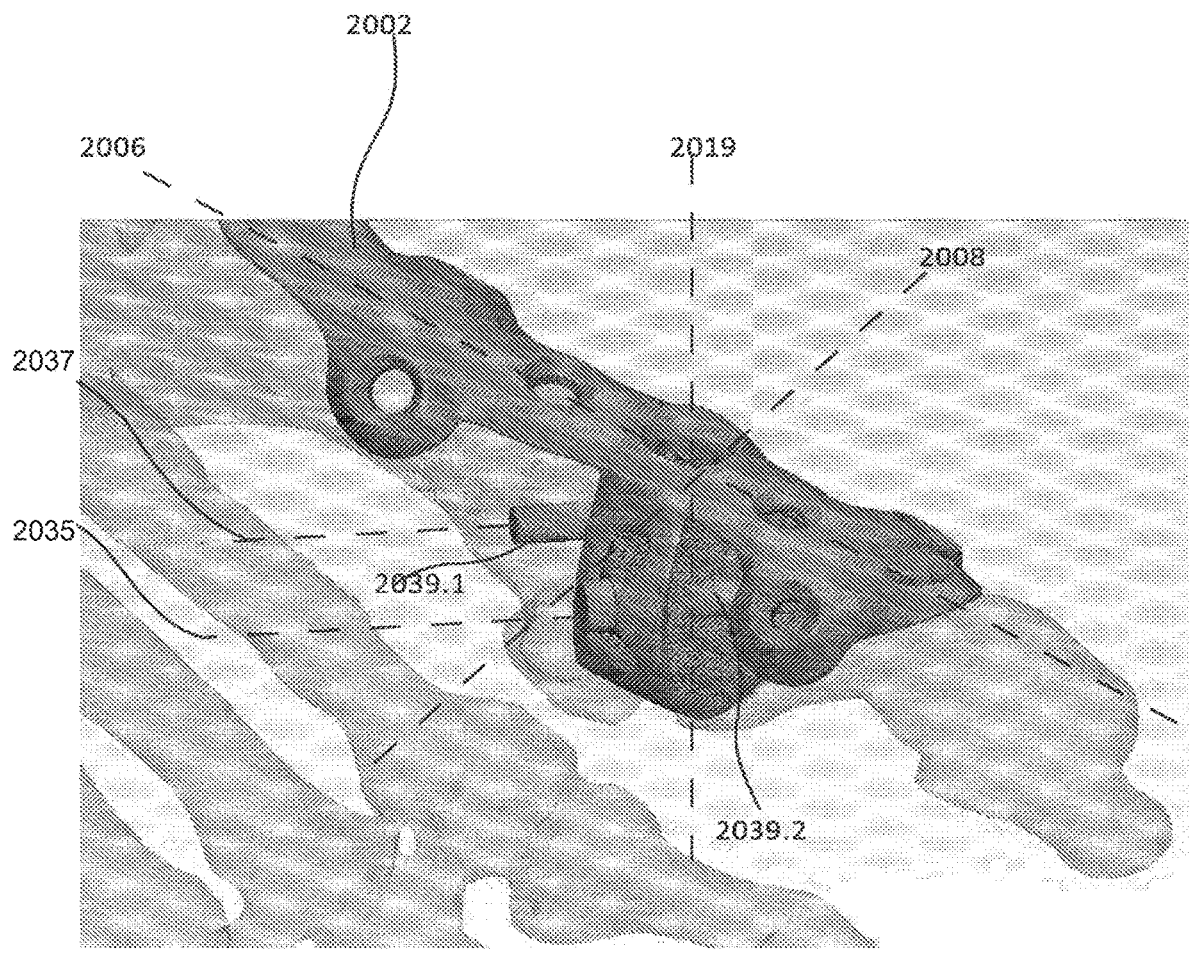
FIG. 70 is a top-left perspective view of the embodiment shown in FIG. 53 implanted on bone.

FIG. 70 is a top-left perspective view of the embodiment shown in FIG. 53 implanted on bone. In this view, the plate 2002 is shown extending along longitudinal axis 2006 with frames 2032 and 2034 securing porous section 2040 therein. Fasteners 2039.1. and 2039.2 are shown extending along their own axes along axis lines 2035 and 2037 in both the longitudinal dimension or axis 2006 and the latitudinal dimension or axis 2008.

Figure 71:
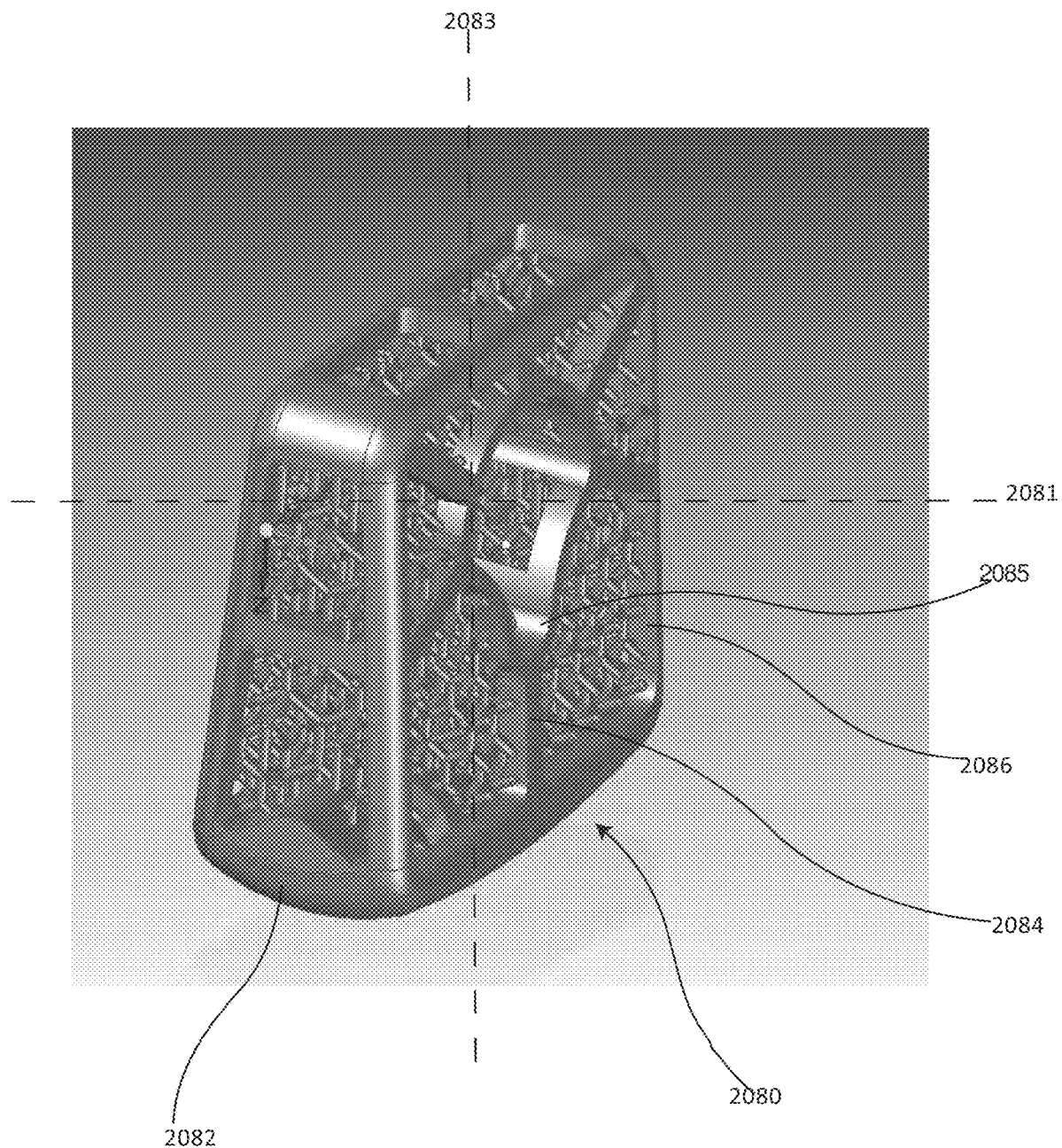
FIG. 71 is a perspective view of another porous section.

FIG. 71 is a perspective view of another embodiment comprising a framed porous section 2080. This porous section is in the form of a framed porous section having a frame 2082 having struts or supports 2084 with a porous section 2086 disposed therein. The frame forms a wedge pattern having at least one side having a substantially triangular cross-section. On at least one face is a pattern that is similar to a light bulb pattern interface 2085 formed by the supports 2084. This light bulb shape having a substantially round opening in the face, allows for an opening to receive a rounded tip for injection of biological material. This framed porous section can be used with the embodiments of FIGS. 1-50 as well as with the embodiments shown in FIGS. 51-75.

Figure 72:
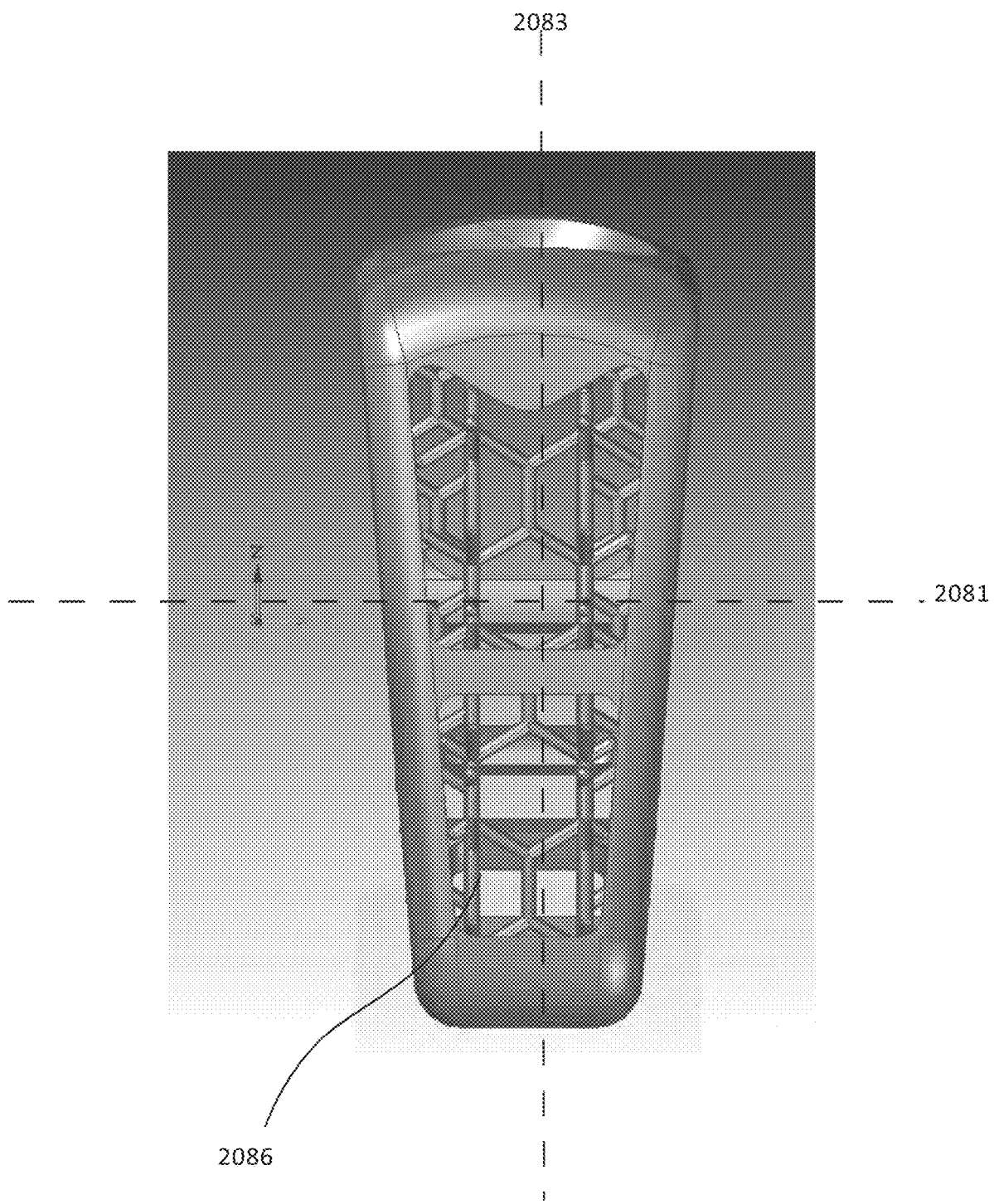
FIG. 72 is a side view of another porous section.

FIG. 72 is a side view of the framed porous section 2080 having the triangular cross-section and having a first axis 2081 extending in a first dimension and another axis 2083 extending in another dimension. When the porous section is used in combination with plate 2002 this first axis 2081 extends substantially along the longitudinal axis 2006. In addition, the second axis 2083 would then extend substantially along the transverse axis 2019. As shown, disposed inside of this frame is the porous section 2086 which can be in the form of any suitable pattern but in at least one embodiment it is formed in the honeycomb pattern shown in FIGS. 57 and 58.

Figure 73:
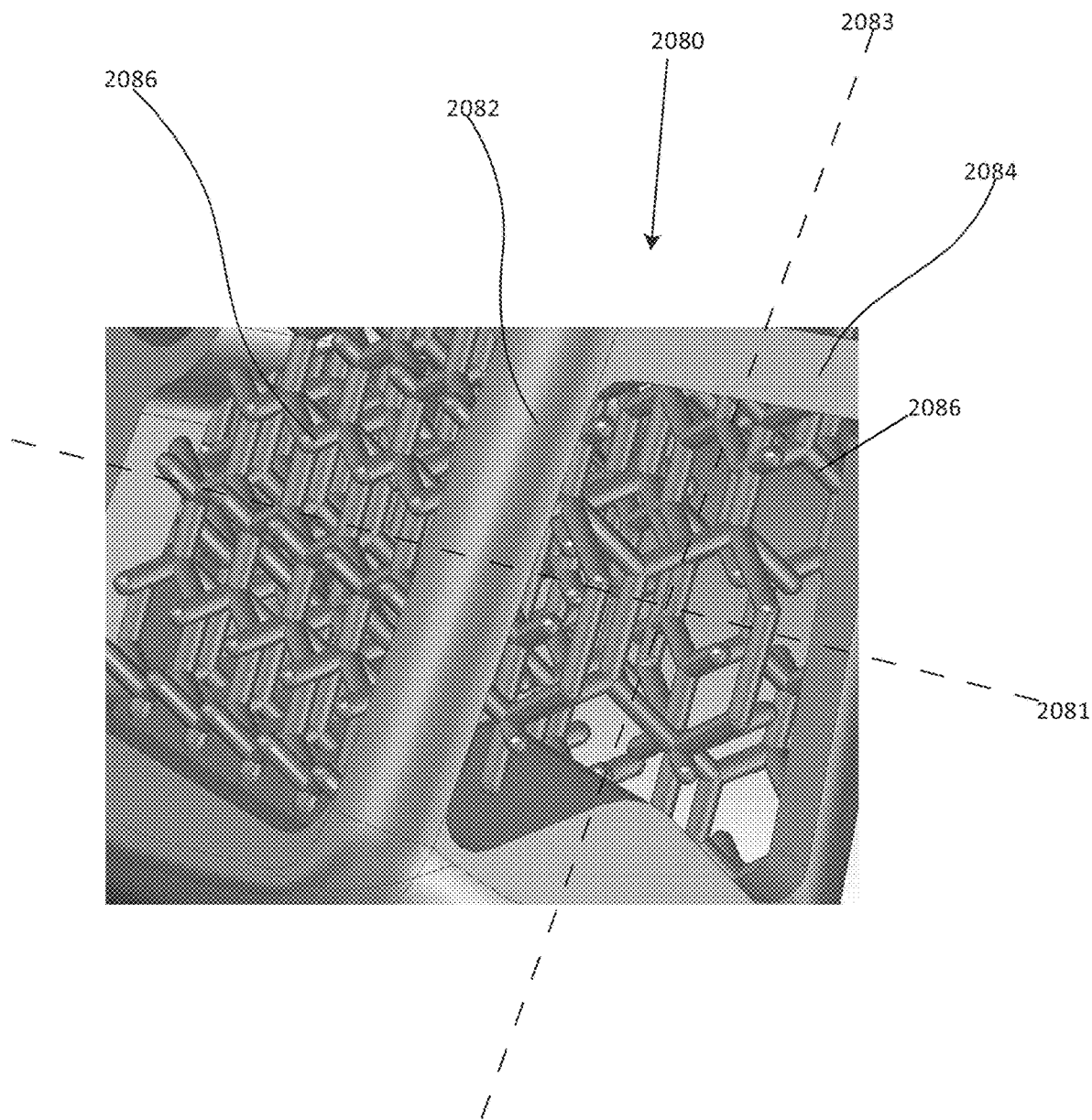
FIG. 73 is a close up view of another porous section.

FIG. 73 shows a close up view of the embodiment of FIG. 72 of a wedge comprising a framed porous section 2080 which shows the porous section 2086 having the repeating pattern which can be for example a honeycomb pattern. This porous section is disposed inside of frame 2082 having struts 2084. Axes 2081 and 2083 are also shown.

Figure 74A:
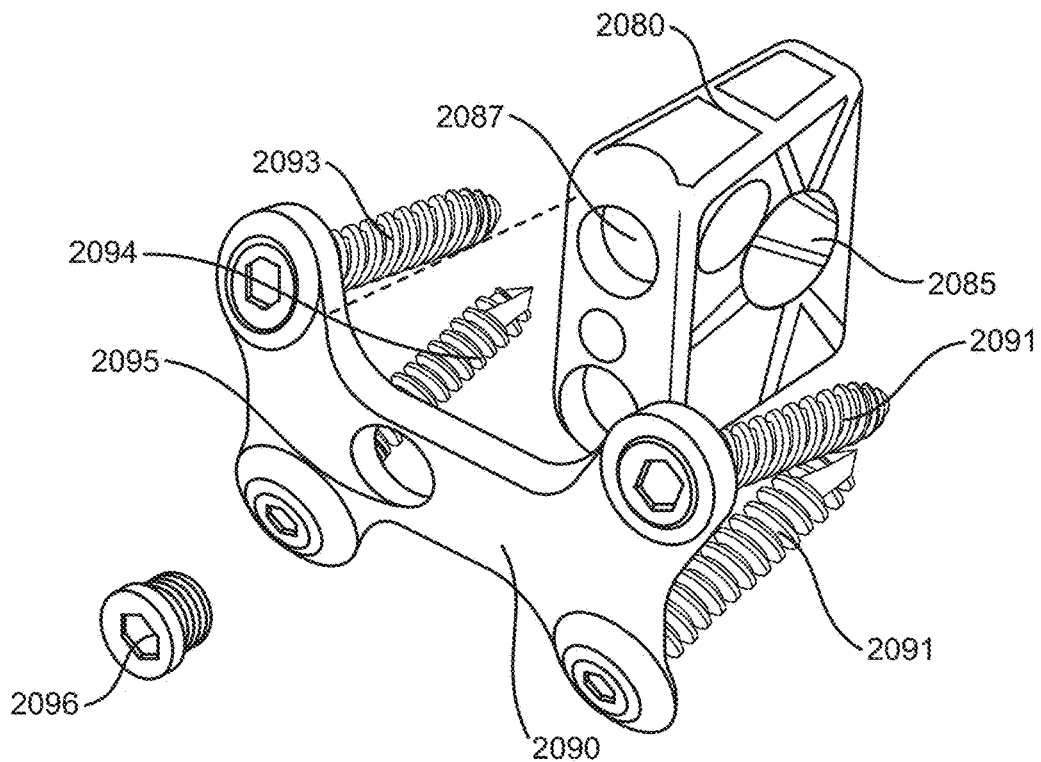
FIG. 74A is an exploded view of an embodiment shown in FIG. 73 with fasteners and a plate shown.

FIG. 74A shows an exploded view of a wedge or framed porous section 2080 having a light bulb shaped interface 2085. Porous section 2080 is configured to be attached to a plate 2090, via at least one fastener 2096 which is configured to fit inside of a central aperture 2095 in plate 2090. In addition, a plurality of fasteners 2091, 2092, 2093, and 2094 are configured to connect the plate 2090 to an adjacent bone or sets of bones to set the bone(s) in place. With this insertion of the plate 2090 and the framed porous section 2080, the framed porous section 2080 can be placed between two different broken bones to allow them to be compressed together. The wedge or framed porous section 2080 includes at least one aperture 2087 which allows for additional biological material to be fed into the porous portion of the framed porous section 2080.

Figure 74B:
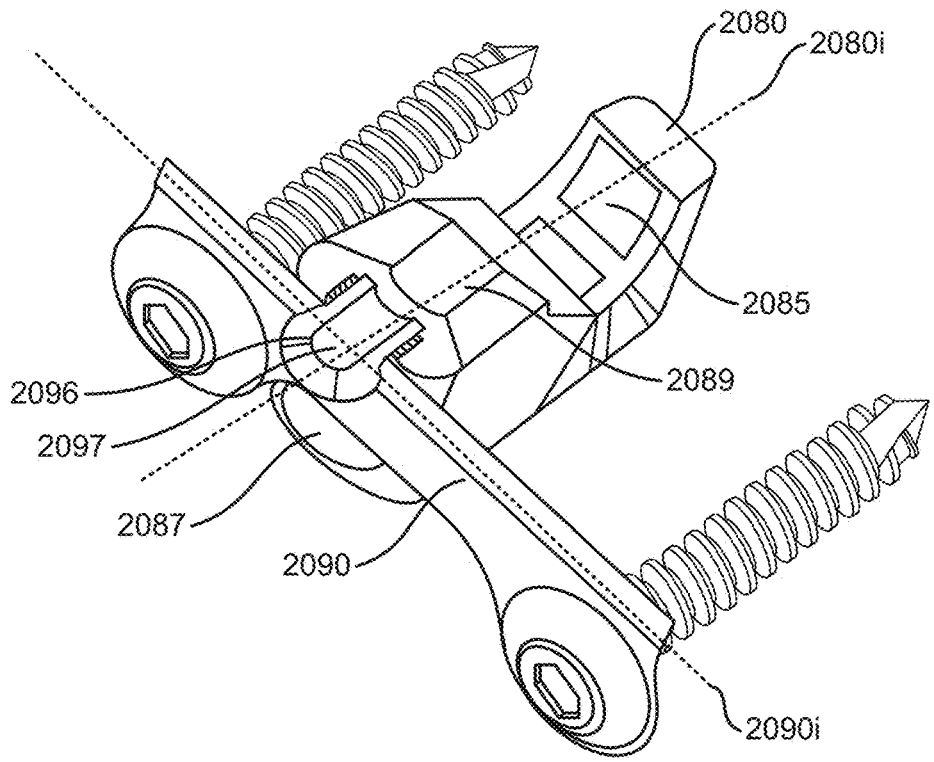
FIG. 74B is a cross-sectional view of the embodiment shown in FIG. 74A.

As shown in FIG. 74B the fastener 2096 has a central hole or channel 2097 which extends through to a inner aperture or channel 2089 to allow biological material to be fed into the framed porous section 2080. This view also shows that plate 2090 extends along a longitudinal axis 2090$i$ and wedge or framed porous section 2080 extends in its longest dimension along axis 2080$i$. Axis 2080$i$ is transverse or substantially transverse to longitudinal axis 2090$i$.

This inner or access aperture such as inner aperture 2089 which may be present in each of the embodiments of the wedges, can be used for a dual purpose, that of a place to receive a fastener such as fastener 2096, wherein the fastener is configured to secure a bone plate such as bone plate 2090 to a bone wedge such as wedge or framed porous section 2080, and also to receive biologic material to promote bone growth. In this embodiment, the inner aperture is used to fasten the plate to the wedge and also is configured to receive biologics for promoting bone growth.

Figure 75:
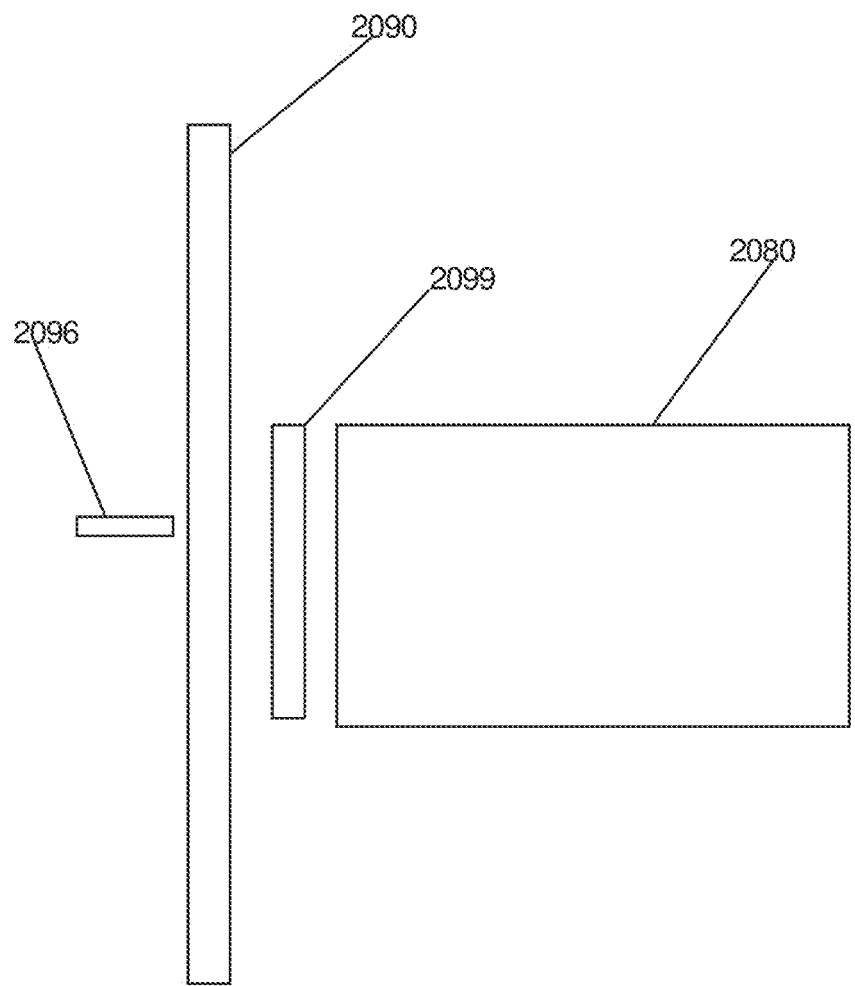
FIG. 75 is a side view of an embodiment having an adapter.

In addition, in FIG. 75 there is shown a kit which comprises a plate such as plate 2090, an adapter 2099 configured to be placed adjacent to plate 2090, and a wedge or framed porous section 2080 of an insert. These components are configured to be fit together and fastened together via fasteners such as fastener 2096 which is configured to bind plate 2090, adapter 2099, and framed porous section 2080 together. In addition, for all of the embodiments disclosed herein the plate section or plate as well as the wedge section and any fasteners can be formed as a kit for use in repairing a bone fracture.

With each of these designs shown in FIGS. 51-70 and/or FIGS. 71-75, and previous FIGS. 1-50, the porous section can be in the form of a porous section having a single density profile as previously described in FIGS. 1-50, or a patterned structure such as a honeycomb pattern, a diamond pattern or any other type of suitable pattern. In addition, with each of the designs shown in FIG. 51-70 or 71-75 the porous section can have a dynamic density profile which changes as there is progression along the porous section from a proximal end outer face 2069 to a distal end outer face 2067 for example. In addition, the designs of FIGS. 1-50 can also include a porous section having a variable or dynamic density or porosity profile as outlined in the embodiments of FIGS. 51-75. For example, the porous architecture of the wedge segment 14 can have a dynamic porosity or density profile. Alternatively, the porous architecture of the other wedge segments such as wedge segment 114, 214, 314, 414, 514, 614, 714, 814, 914, 1014.

However, depending on the need for connection to any bone, the density profile can be dynamic or changing in other dimensions as well such as transverse to a direction extending from a proximal end to a distal end. This density profile can change based upon the size of the porous openings such as changing the spacing from 1.5 mm for openings to 2.5 mm. Another way to view the differences in porosity is to change the volume of the void space Vv vs. the volume of the total bulk space Vt. This can be expressed via the formula below:

Porosity=$Vv/Vt$

Thus, the porosity change can vary in the porous section such as porous section 2040 depending on the position and can be calculated as a percentage as well. In at least one embodiment, the difference in porosity between the most porous region and the least porous region can be as much as 70%. In at least another embodiment, the difference in porosity between the most porous region and the least porous region can be as much as 50%. In another embodiment, the difference in porosity between the most porous region and the least porous region can be as small as 5%. Of course, the above identified embodiments are configured to provide for any variation between the above percentage differences between 70% and 5%.

The changes in density to the porous section such as porous section 2040 are configured so that in regions that the porous section is adjacent to bone material, the density may be higher while the porosity lower so that there is more surface area on the porous section to attach to an adjacent bone. Moving along the porous section from the proximal end to a central region, the density drops so that in this region. a health care practitioner can fill this region with biological material such as stem cells, bone marrow or other synthetic material or growth agents to aid in the growth of new bone material. Moving out from the central region the density increases or the porosity drops so that there is once again more surface area for an adjacent bone at a distal end to be coupled to adjacent struts or supports of a porous section such as section 2040. With this design, the varying density and/or porosity is designed to mirror the profile of a bone with a cancellous inner portion and a cortical outer region.

Ultimately, the density profile can be optimized based upon a pre-set algorithm or formula based upon the area of insertion. For example, the density profile can be optimized based on the specific bone the device is being inserted, based upon the expected strength that is needed and also the types of movements in that region. This density profile can also be optimized for osteosyntheses and bone healing. This occurs through smaller pore size on the outsides and larger pore sizes on the insides.

Ultimately there is at least one embodiment which includes a bone fixation implant such as any one of implant 10, 110, 210, 310, 410, 510, 610, 710, 810, 910, 1010, or 2000 comprising: an elongated plate such as an elongated plate 12, 112, 212, 312, 412, 512, 612, 712, 812, 912, 1012, or 2002 having a plurality of apertures such as apertures 2004, 2012, 2014, 2016, 2018, 2022, and a bone wedge segment such as porous section or wedge segment 14, 114, 214, 314, 414, 514, 614, 714, 814, 914, 1014, or 2040 coupled to the elongated plate 12, 112, 212, 312, 412, 512, 612, 712, 812, 912, 1012, or 2002 wherein the bone wedge segment comprises a plurality of structural elements comprising structural members, struts or a frame such as frame 2030. In at least one embodiment the structural members of this frame can have an outer surface that is substantially roughened or pitted as a surface (See FIG. 57) to encourage interactions with bone or other biological material. Alternatively, the surface can be substantially smooth. The porous section of this bone wedge section can either be of a uniform porosity, or be of a variable porosity, with at least two pores or at least two pore openings for each unit cell having different opening or pore dimensions such as that shown by openings 2054, 2054.1 2054.2, or 2054.3. The differences in porosity can be based upon the depth along the porous section, with an inner region such as inner region 2065, 2065.1 or 2074 being less dense or more porous than an outer region or outer face 2067, 2067.1, 2069, 2069.1, 2072, or 2076 for example. Alternatively, the differences in porosity can vary even along a single face at a same depth such as via different pore openings shown by the different pore openings 2054.1, or 2054.3 shown in FIG. 62.

Figure 76:
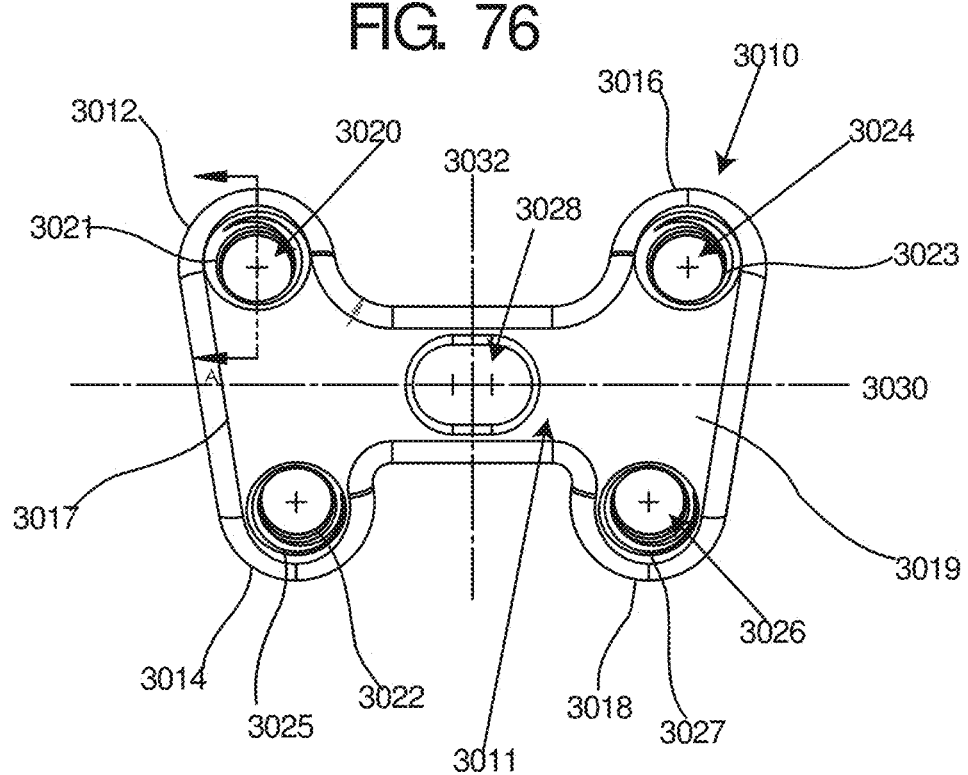
FIG. 76 is a front view of a bone fixation device.

FIGS. 76-91 show another embodiment using similar principles to that outlined above. For example, FIG. 76 is a front view of a plate or bone fixation device 3010. The bone fixation device includes at least one following elements, a body 3011 as well as a plurality of extension sections 3012, 3014, 3016, and 3018. Essentially, the body in combination with the extensions sections comprise an H-shaped body having a left side 3017 and a right side 3019. This body 3011 and these extension sections each includes a plurality of openings such as openings 3020, 3022, 3024, 3026, and 3028. Openings 3020, 3022, 3024, and 3026 are substantially round shaped, while opening 3028 is substantially oval shaped. Openings 3020, 3022, 3024, and 3026 each have threads such as threads 3021, 3023, 3025, and 3027. Each of these sets of threads are configured to receive an associated fastener such as a screw. These threaded openings can be in the form of a beveled opening which is configured to receive a screw which can have an angled or beveled head. Opening 3028 is configured to receive a fastener as well, however it also has an elongated opening so as to receive additional material such as biologic material such as stem cells, bone marrow or other synthetic material or growth agents to aid in the growth of new bone material.

Body 3011 extends longitudinally along axis line 3030 and latitudinally along axis line 3032. The longitudinal extension of body 3011 is longer than the latitudinal extension. In at least one embodiment, the latitudinal extension is approximately ⅔ of the longitudinal extension.

Figure 77:
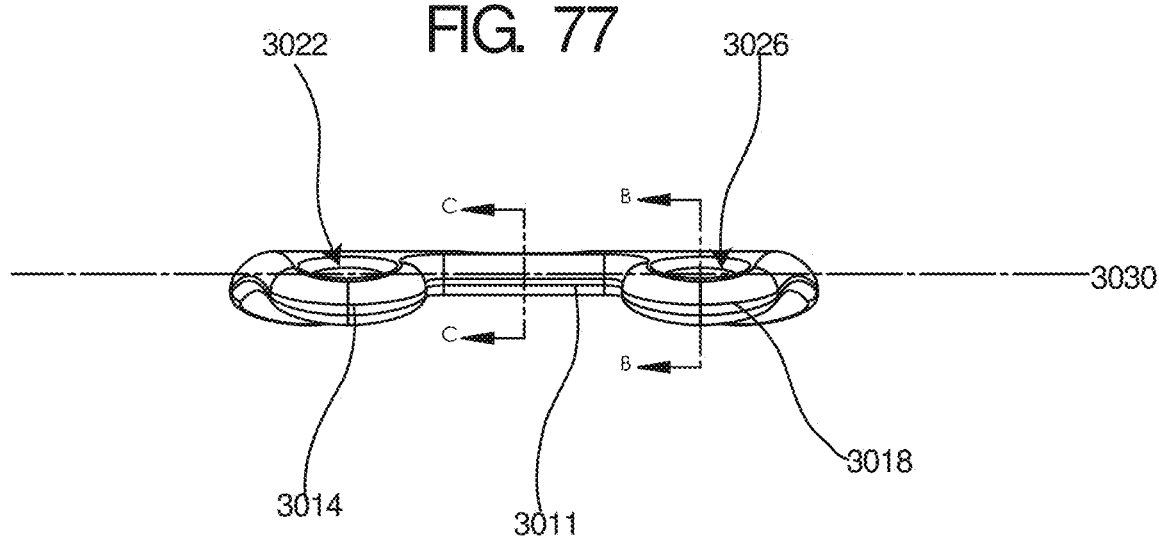
FIG. 77 is a side view of the bone fixation device.

FIG. 77 is a side view of the bone fixation device showing body 3011 with extension sections 3014 and 3018 extending out from body 3011 along with cross sectional lines B-B and C-C. This body 3011 with the associated extension sections has a curved surface which causes the extension sections 3012, 3014, 3016, and 3018 to curve down around the main body 3011.

Figure 78A:
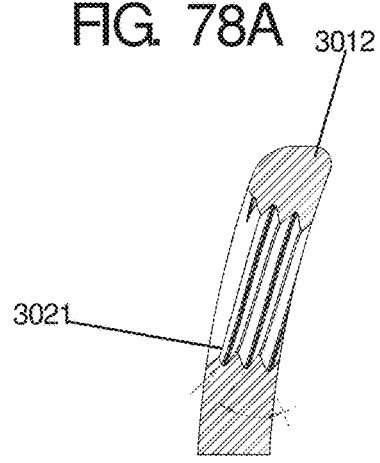
FIG. 78A is a side view taken along line A-A.

FIG. 78A is a side cross-sectional view taken along line A-A shown in FIG. 76. In this view, there is shown the curvature of the extension section 3012, and also threads 3021 which are set into opening 3020. These treads are angled threads which are designed to guide the fastener such as a screw into an adjacent bone at an angle. That angle is offset from an axis that is substantially perpendicular to the longitudinal extension of the body 3011.

Figure 78C:
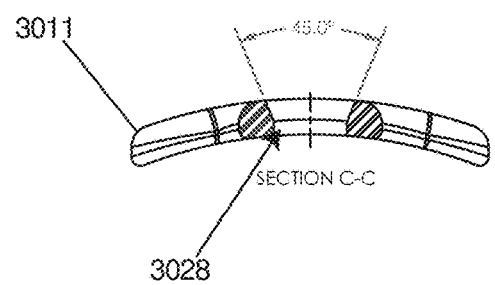
FIG. 78C shows a side view of the device taken along the line C-C.
Figure 78B:
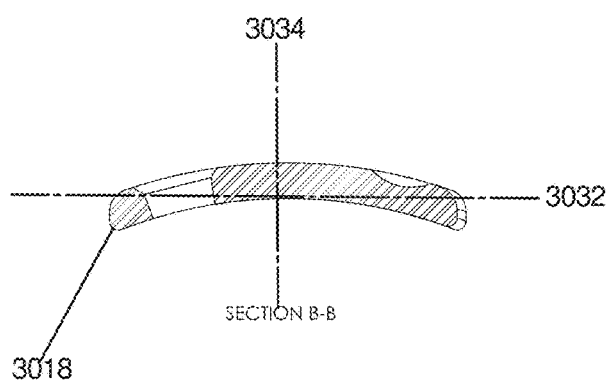
FIG. 78B shows a side view of the bone fixation device taken along the line B-B.

FIG. 78B shows a side cross-sectional view of the bone fixation device taken along the line B-B. In this view, the section along line B-B shows the general curvature of the extension section 3018.

FIG. 78C shows a side cross-sectional view of the device taken along the line C-C. This side cross-sectional view shows that the opening 28 has a 45 degree opening angle. In addition, as shown by this cross-sectional view the body 3011 is substantially curved as well with the curvature being around axes 3032 and 3034.

Figure 78D:
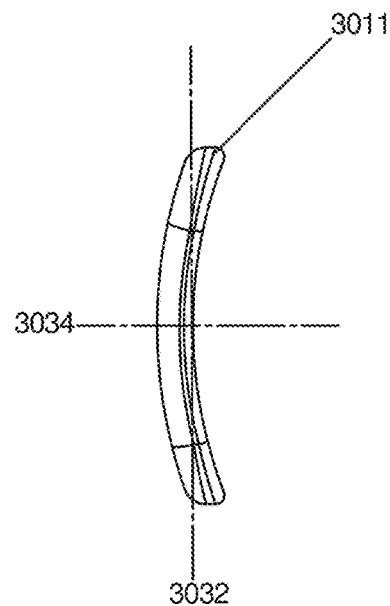
FIG. 78D shows a side view of the device.

FIG. 78D shows a side view of the device wherein body section 3011 is shown to have a curved profile with a curvature between 10-20 degrees in angle.

Figure 79A:
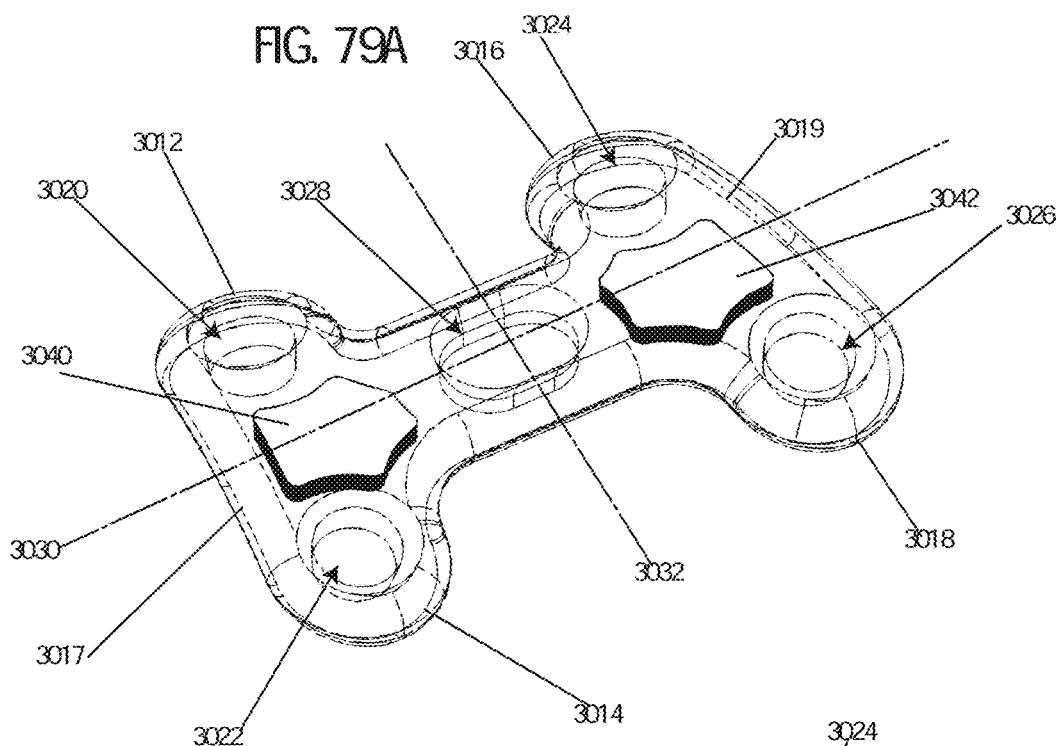
FIG. 79A shows a perspective view of the device shown in FIG. 1.

FIG. 79A shows a top perspective view which is in the form of a wire-frame view of the device shown in FIG. 76. In this view, there are shown mesh sections 3040 and 3042 which are shown on the underside of the body 3011. These mesh sections 3040 and 3042 are shaped to fit into body 3011 and to fit between openings 3020 and 3022 in extension 3012 and 3014 and to fit between openings 3024 and 3026 in respective extensions 3016 and 3018. These mesh sections are positioned on both the left side 3017 and the right side 3019 of the body 3011. Hole or opening 3028 is shown extending longitudinally along axis 3030 in a longitudinal dimension and latitudinally along latitudinal axis 3032. The extension of opening 3028 is longer along the longitudinal axis 3030 than in the direction of the latitudinal axis. In at least one embodiment, these mesh sections have a porosity that is similar to that of the wedge of FIGS. 51-75. For example, these mesh sections can be of a honeycomb pattern or a diamond pattern in a lattice structure. Alternatively, these mesh sections can have a standard porosity. Alternatively, these mesh sections can have a variable porosity. These sections can also have a substantially uniform architecture or a variable shaped architecture. Furthermore, for both the plate section as well as for the struts for the porous architecture of the mesh sections 3040, and 3042, the outer surface in at least one embodiment is smooth. In another embodiment, the outer surface of the plate section and the struts of the porous architecture of the mesh sections is substantially smooth. In another embodiment the outer surface of the body of the plate section 3011 and the struts of the mesh sections 3040, and 3042 is substantially rough. In another embodiment the outer surface of the body of the plate section 3011 and the struts of the mesh sections 3040, and 3042 is rough.

With respect to the different embodiments herein the term smooth means an intentionally formed surface with no noticeable roughened surface. In addition, the term substantially smooth means that the surface is smooth over a majority portion of the surface. The term substantially rough means that the outer surface is noticeably rough over a majority portion of the surface. Finally, the term rough means that the outer surface is noticeably rough throughout the entire outer surface.

Figure 79B:
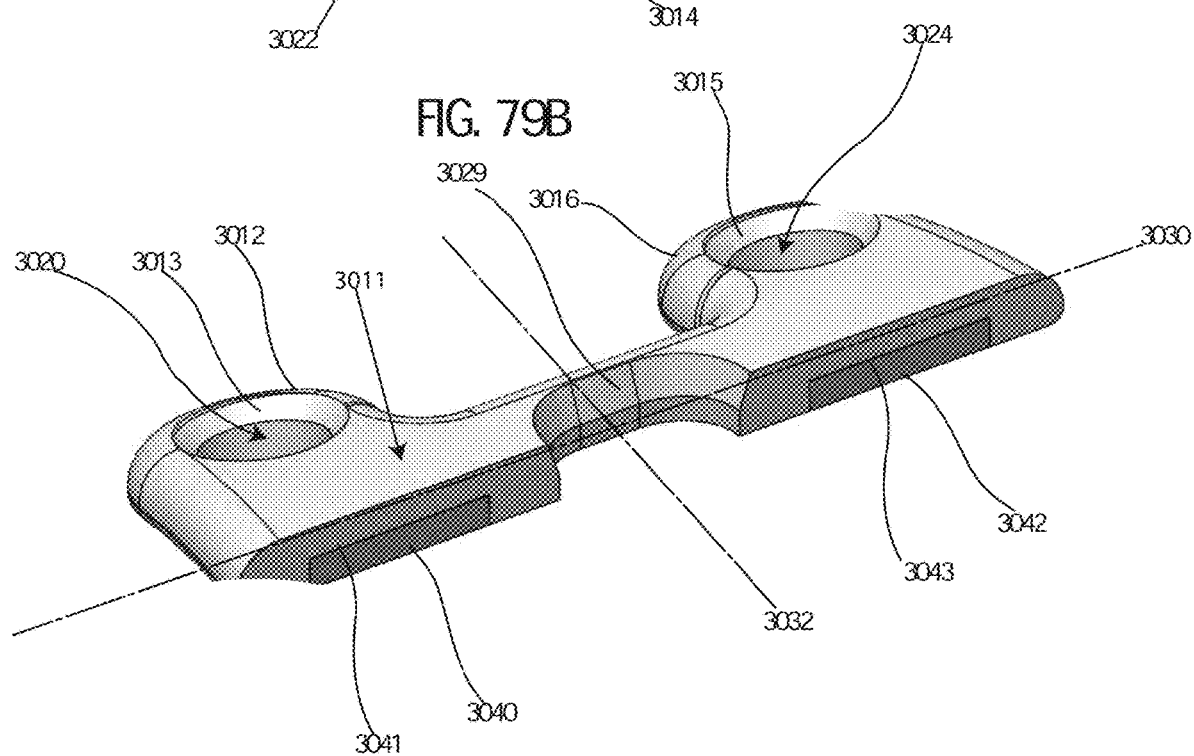
FIG. 79B shows a side cross-sectional view of the device shown along the line I-I in FIG. 79A.

FIG. 79B shows a side cross-sectional view of the device shown along the line 3030 in FIG. 79A. In this view, there is shown indents formed by surfaces 3041 and 3043 respectively which are configured to receive mesh sections 3040 and 3042. This view also shows the beveled edges 3013 and 3015 of openings 3020 and 3024 respectively in extensions 3012 and 3016 respectively. This view also shows that the mesh sections are positioned only on one side of the body 3011.

Figure 80:
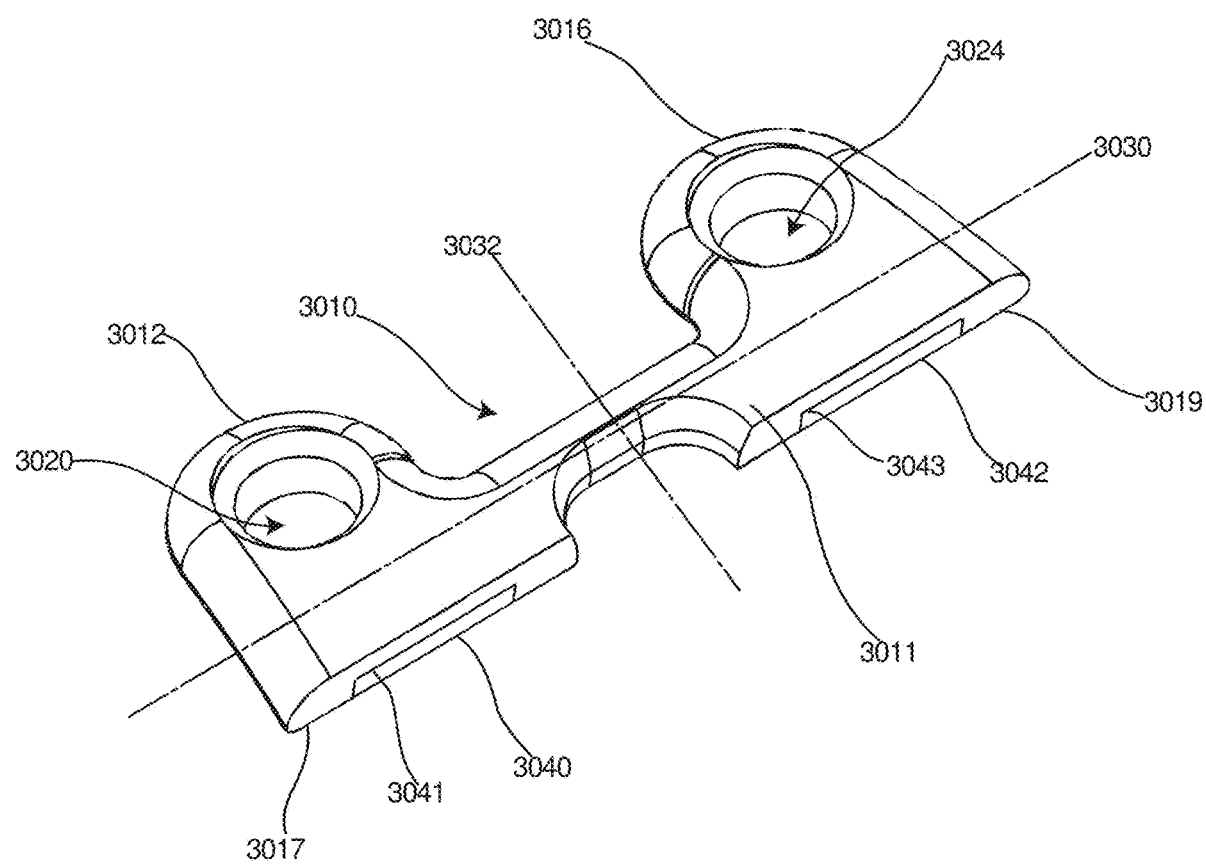
FIG. 80 shows a side cross-sectional view of the device shown in FIG. 1 taken along the line 30 shown in FIG. 79B.

FIG. 80 shows a side cross-sectional view of the device shown in FIG. 76 taken along the line 3030 shown in FIG. 79A. This view is similar to the view shown in FIG. 79B which shows the device 3010 having a body section 3011 with a left side 3017 and a right side 3019. Mesh sections 3040 and 3042 are inserted into body section 3011 into recesses 3041 and 3043. Extensions 3012 and 3016 are shown with openings 3020 and 3024.

Figure 81A:
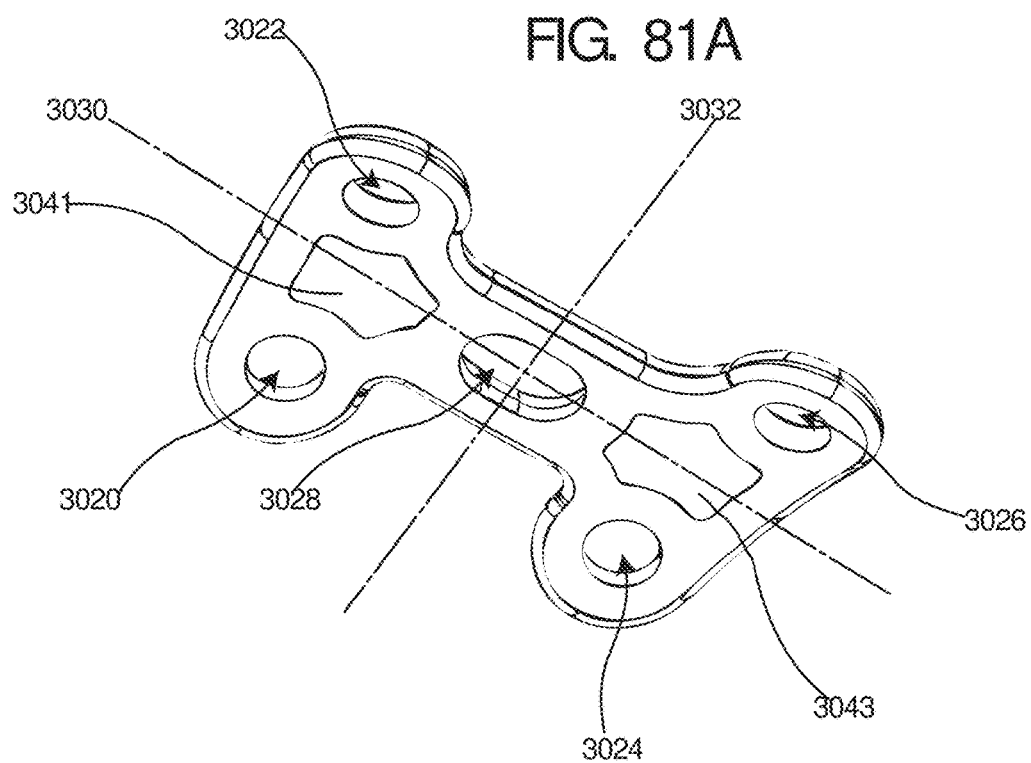
FIG. 81A is an underside perspective view of a body section of the bone fixation device without mesh sections.
Figure 81B:
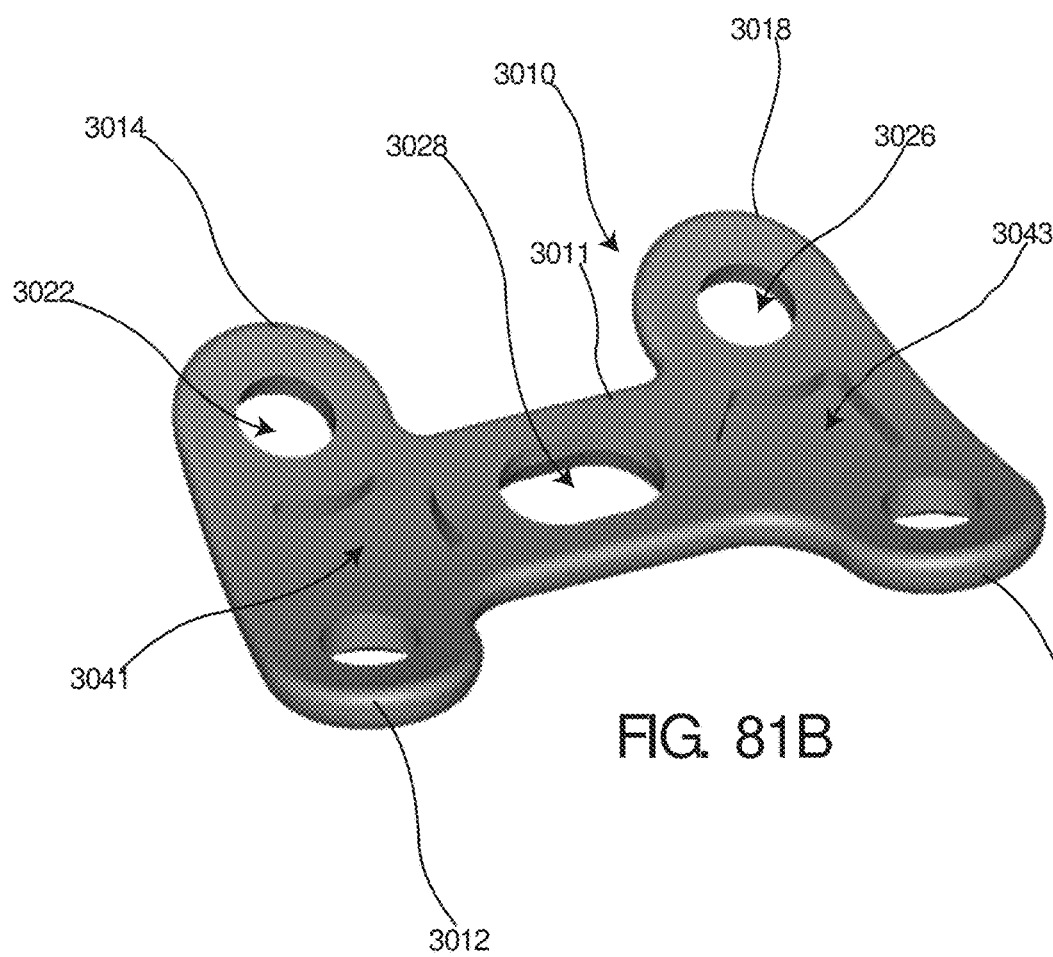
FIG. 81B is a flipped underside perspective view of the body section of the bone fixation device without mesh sections.

FIGS. 81A and 81B shows respective perspective views of a bone fixation device which shows a body section 3011 having openings 3020, 3022, 3024, and 3026 in extensions 3012, 3014, 3016 and 3018, and opening 3028 in body section 3011. There is also shown as recesses 3041 and 3043. These recesses 3041 and 3043 are six sided recesses but could be in any type of shape such as round, square or any other suitable shape. The mesh sections 3040 and 3042 which are shown in greater detail in FIGS. 82A-85.

Figure 82A:
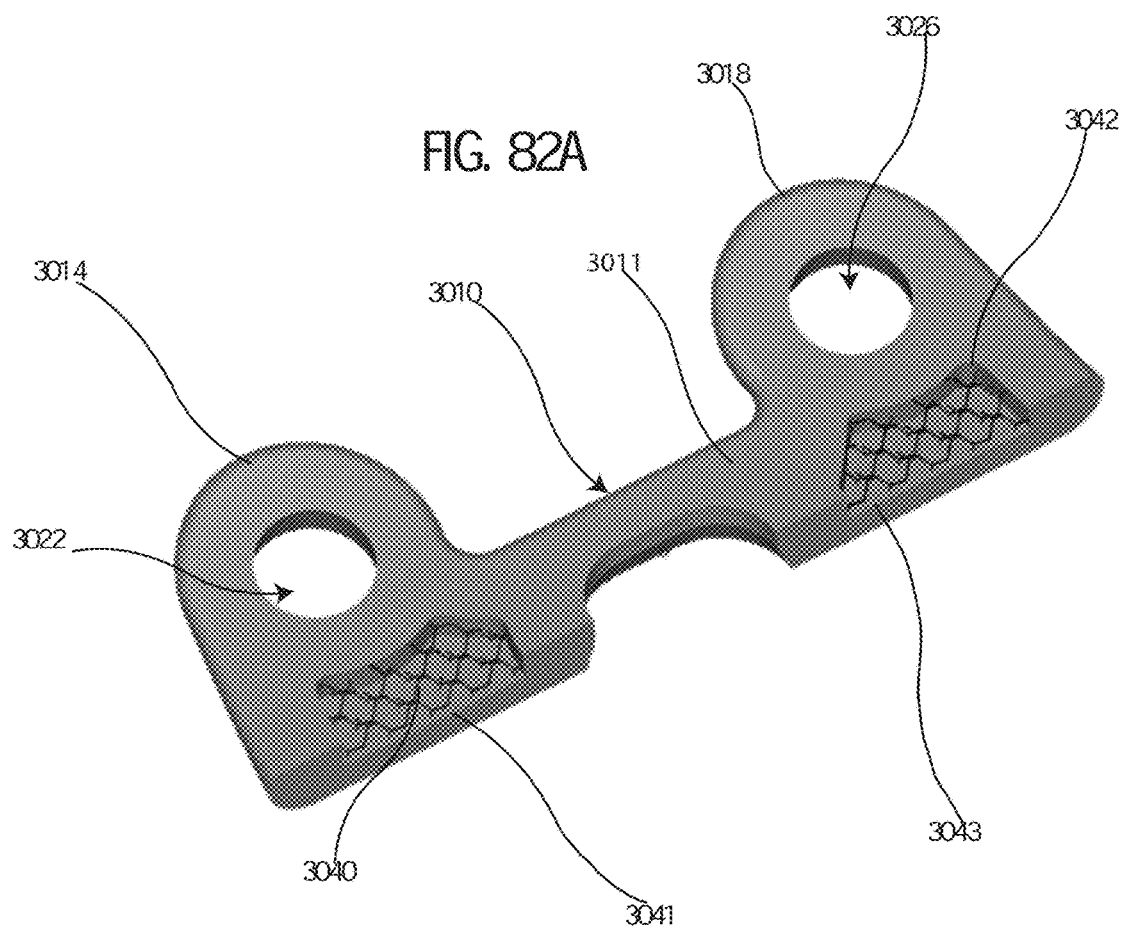
FIG. 82A shows an under-side cross-sectional view of the device taken along line 30.
Figure 82B:
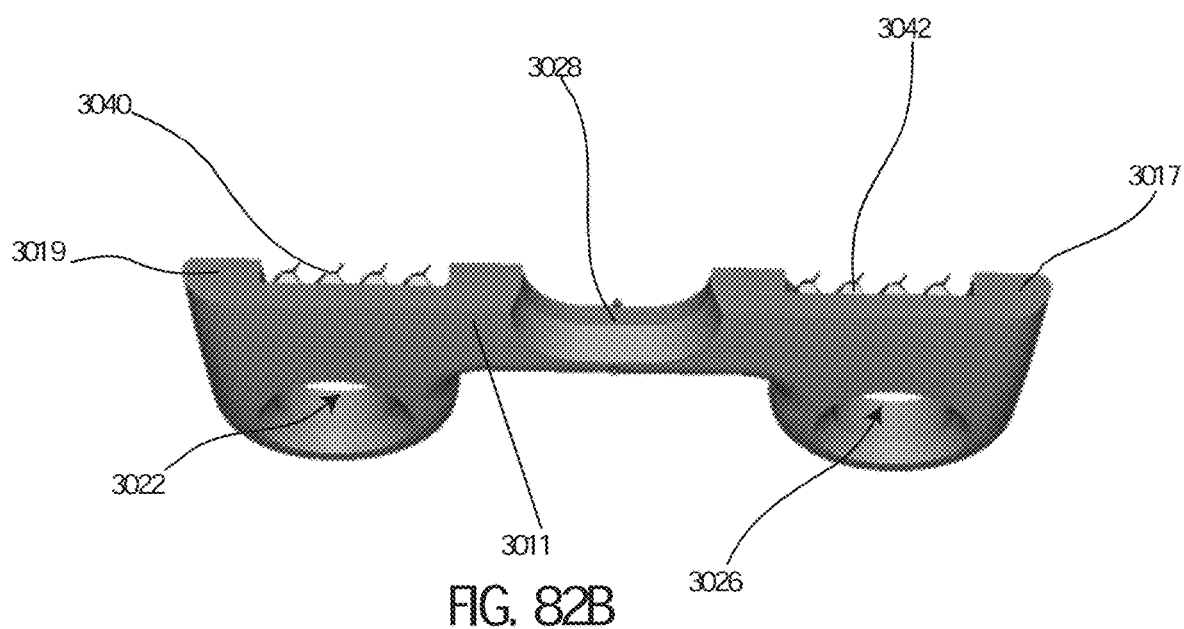
FIG. 82B show a top side cross-sectional view of a bone fixation device.

FIG. 82A shows an underside view perspective cross-sectional view of the device 3010 taken along the line 3030. This view shows mesh sections 3040 and 3042 disposed inside of respective recesses 3041 and 3043. These mesh sections 3040 and 3042 have a lattice structure that is substantially diamond shaped pattern which is configured to receive portions of a bone material. In another embodiment, the lattice structure can be hexagonal in shape. In another embodiment, this lattice structure can be as a plurality of cells in a honeycomb pattern. FIG. 82B shows the mesh sections 3040 and 3042 which are embedded with the main body section 3011.

Figure 83:
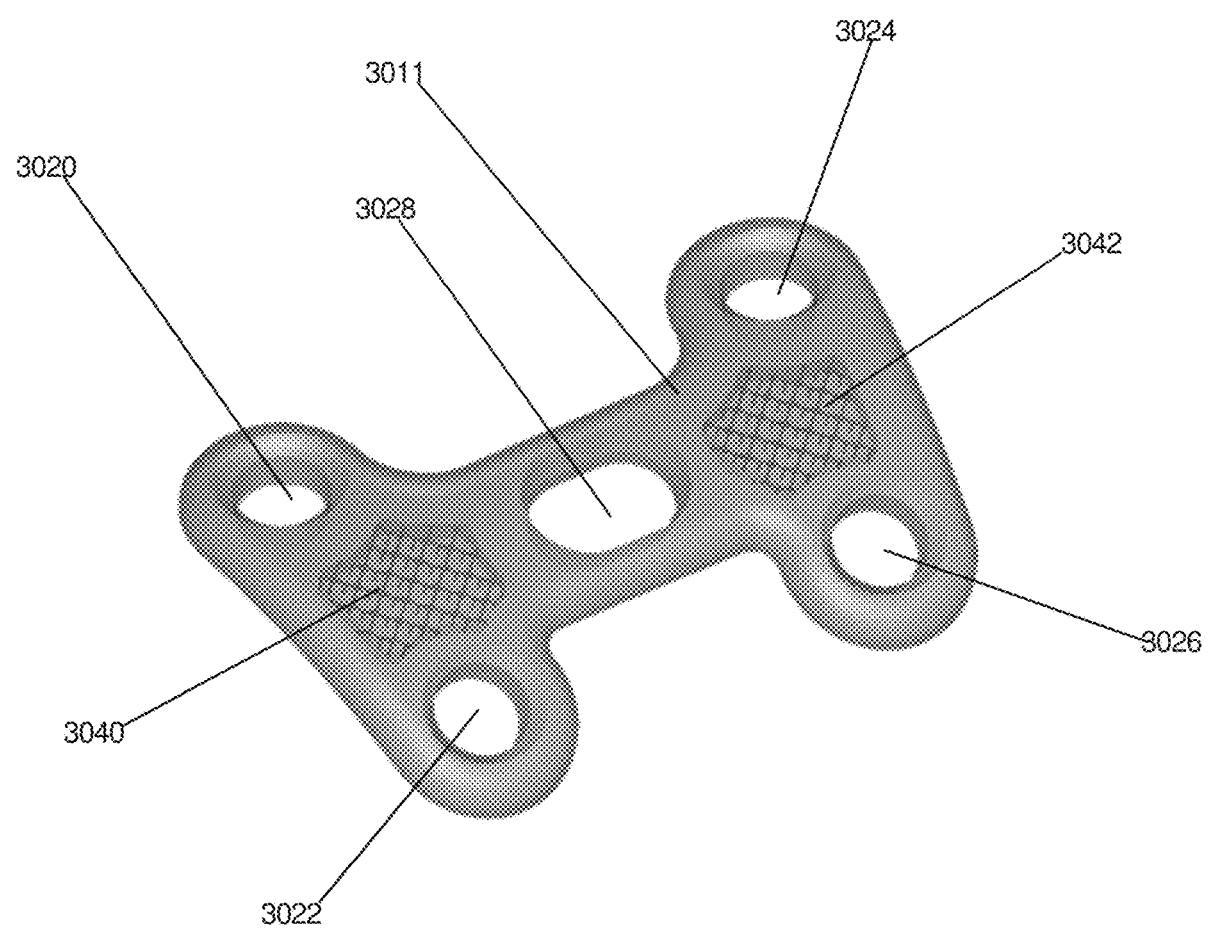
FIG. 83 shows an underside perspective view of the bone fixation device showing a plurality of mesh segments embedded into the bone fixation device.
Figure 84:
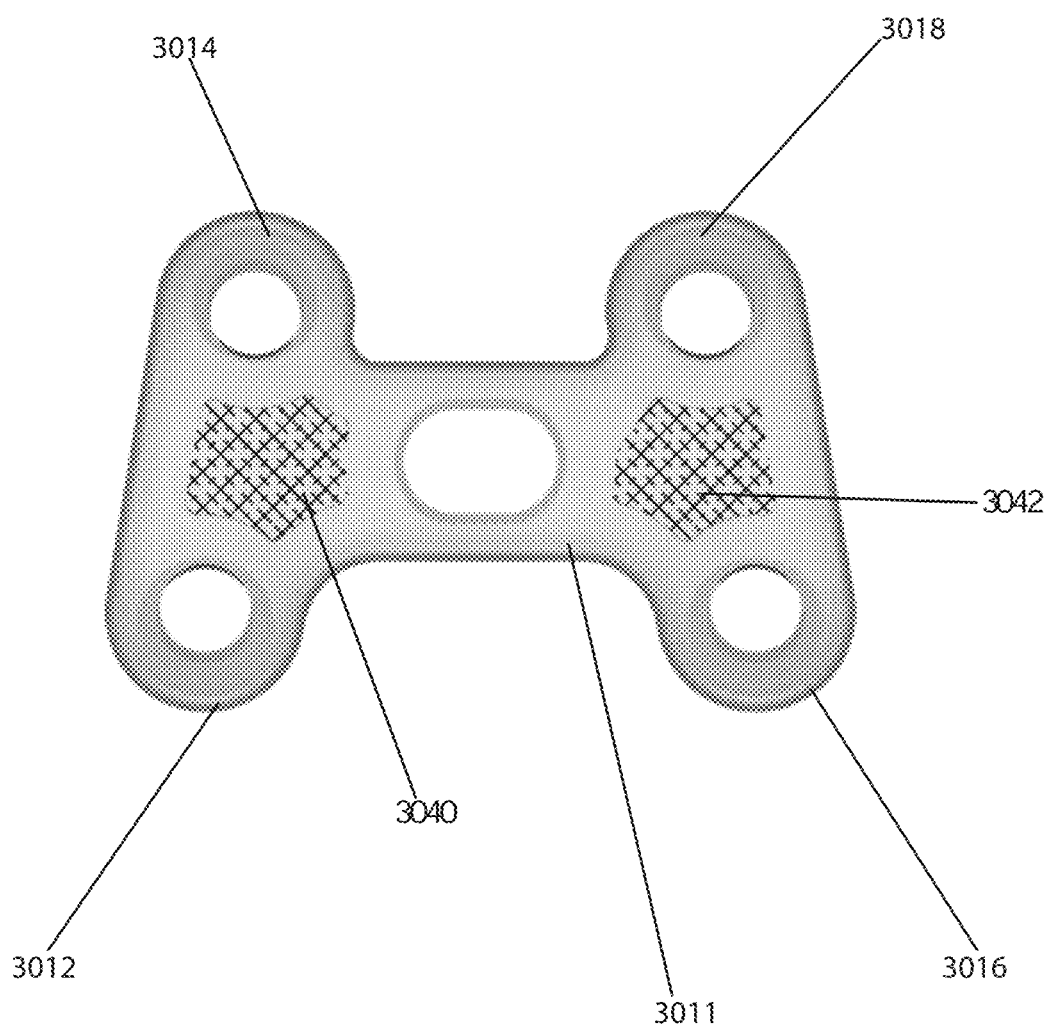
FIG. 84 shows an underside view of the bone fixation device shown in FIG. 83.

FIG. 83 shows an underside view of the bone fixation device. In this view, there is a body section 3011, mesh sections 3040 and 3042 and recesses 3041 and 3043. Openings 3020, 3022, 3024 3026 and 3028 are also shown. Mesh sections 3040 and 3042 can be made separate from indents or recesses 3041 and 3043, or they can be made integral with recesses 3041 and 3043. FIG. 84 is a side perspective view of the bone fixation device with the mesh sections 3040 and 3042 disposed therein. In at least one embodiment, the device can be made from a three-dimensional printing process where the device is made from a sequential layer by layer process.

FIG. 84 shows an underside view of the bone fixation device 3010 which shows the curvature of the body 3011 of the bone fixation device showing the extensions 3012, 3014, 3016 and 3018, with the mesh sections 3040 and 3042 disposed adjacent to opening 3028.

FIG. 85 shows body 3011 along with the extensions 3012, 3014, 3016, and 3018 as well as opening 3028. Body 3011 has a curvature so that this underside of this device is shown as concave. Mesh sections 3040 and 3042 are also shown.

These mesh sections can have pores of any suitable diameter. For example, FIG. 86A shows a perspective view of at least one other mesh section which have a significantly smaller porosity than mesh sections 3040 and 3042. In addition, each of these mesh sections 3040, 3042, and have for example a first face 3044a, and an opposite second face 3044c (See FIG. 86B) as well as peripheral sides such as sides 3044b and 3044d. Peripheral sides 3044b and 3044d are formed in a substantially curved manner and form an interface with indented sections 3041 and 3043 of body 3011. With each mesh section 3040, 3042, 3044, there can be at least five curved peripheral sides and at least one substantially flat side. In at least one embodiment, the curvature of the five sides can be concave. These mesh sections can extend along axes 3045 and 3047 as well.

FIGS. 86C and 86D show the more porous versions of the mesh sections 3040 and 3042.

Figure 87A:
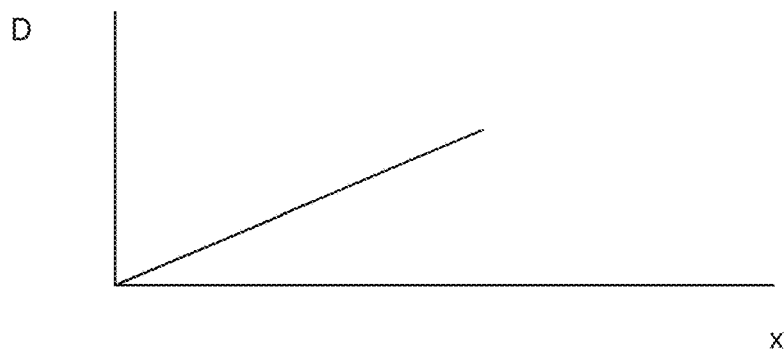
FIG. 87A is a view of a graph of a porosity profile of a first embodiment.
Figure 87B:
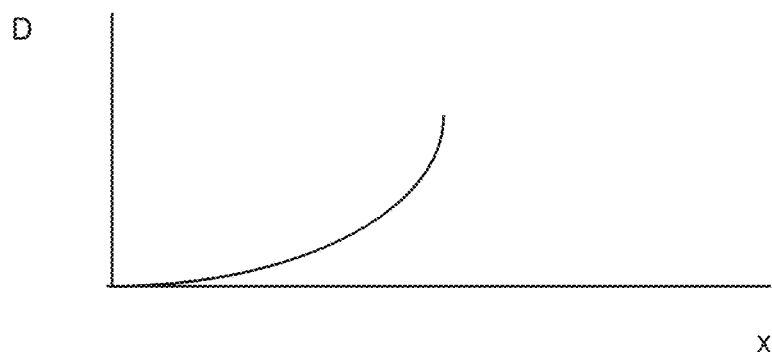
FIG. 87B is a view of a graph of a porosity profile of a second embodiment.
Figure 87C:
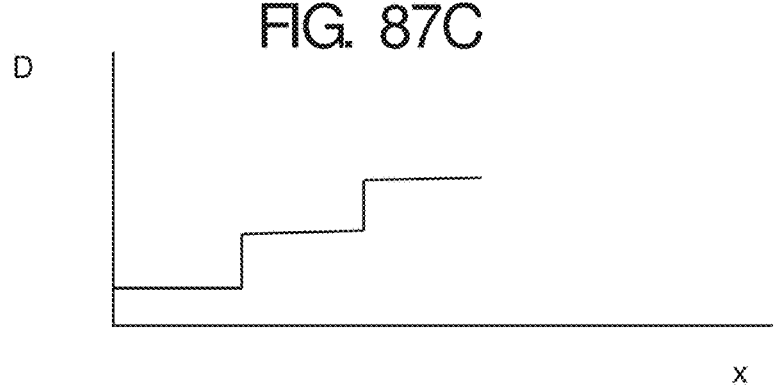
FIG. 87C is a view of a graph of a porosity profile of a third embodiment.

In addition, mesh sections 3040, 3042, and 3044 can have a variable porosity profile such that the porosity of the mesh section at first face 3044a is greater than the porosity at the second, opposite face 3044c when moving along axis 3049. The varying porosity profile allows for the mesh section to have a greater interaction with adjacent bone structure at a for example a first face 3044A, vs. a stronger structure with lower porosity at the opposite face 3044c. The porosity profile which comprises increasing density from one side to another side can be in the form of a straight line increase in density moving along axis 3049 (See FIG. 87A). Alternatively, the porosity profile can be in the form of a sinusoidal curve or ellipsis (FIG. 87B), or in a step wise manner (FIG. 87C). These types of porosity profiles can also be used with any one of the porous wedge sections of FIGS. 1-75 as well.

Figure 87D:
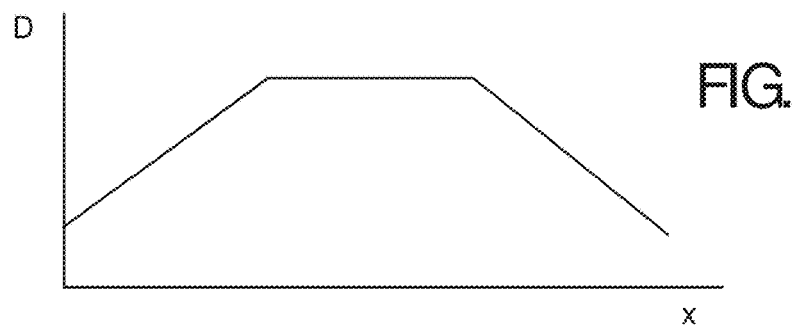
FIG. 87D is a view of a graph of a porosity profile of a fourth embodiment.
Figure 88:
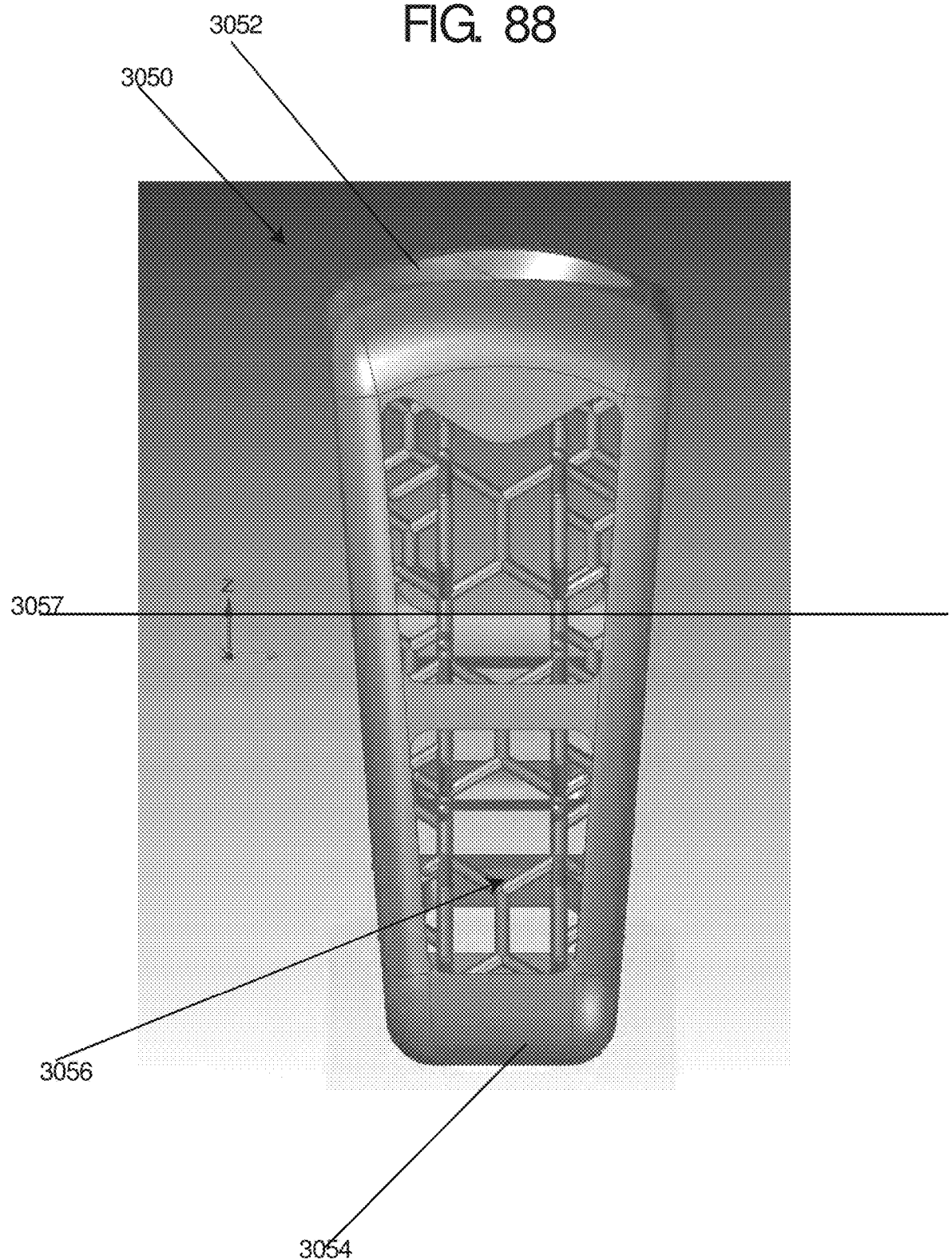
FIG. 88 is a side view of a wedge.
Figure 89:
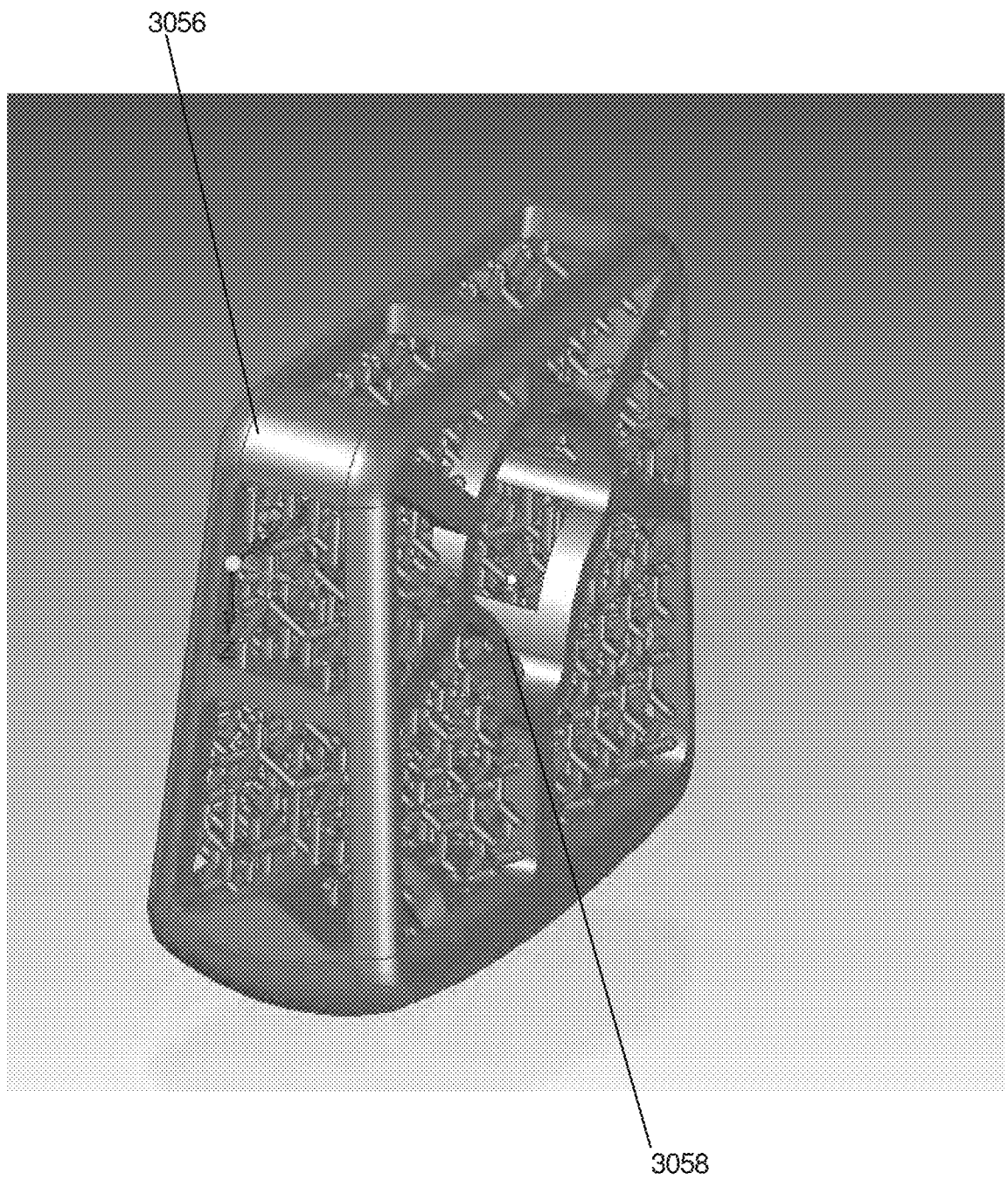
FIG. 89 is another side view of a wedge.

This implant device 3010 can be used along with another type of implant device which can be positioned between two portions of broken bones. For example, wedge device 3050 shown by way of example in FIGS. 88 and 89 can be in the form of any suitable shape and positioned between two broken bones. Implant device 3010 can be positioned adjacent to wedge device 3050 such that a top opening 3052 is positioned adjacent to opening 3028. At least one fastener can be used to fasten wedge 3050 to implant device 3010. Alternatively, the implant device 3010 and wedge device 3050 can be formed as a single unit and printed in a stepwise manner. The wedge itself 3050 can include a cage section 3054 and a mesh section 3056. The mesh section 3056 can also have a porosity profile which is variable as indicated in FIGS. 87A-87C. Alternatively, as shown in FIG. 87D, this wedge section can have a porosity profile that becomes increasingly more dense towards a central region of the mesh section and then less dense as taken along line 3057 shown in FIG. 88.

Figure 90:
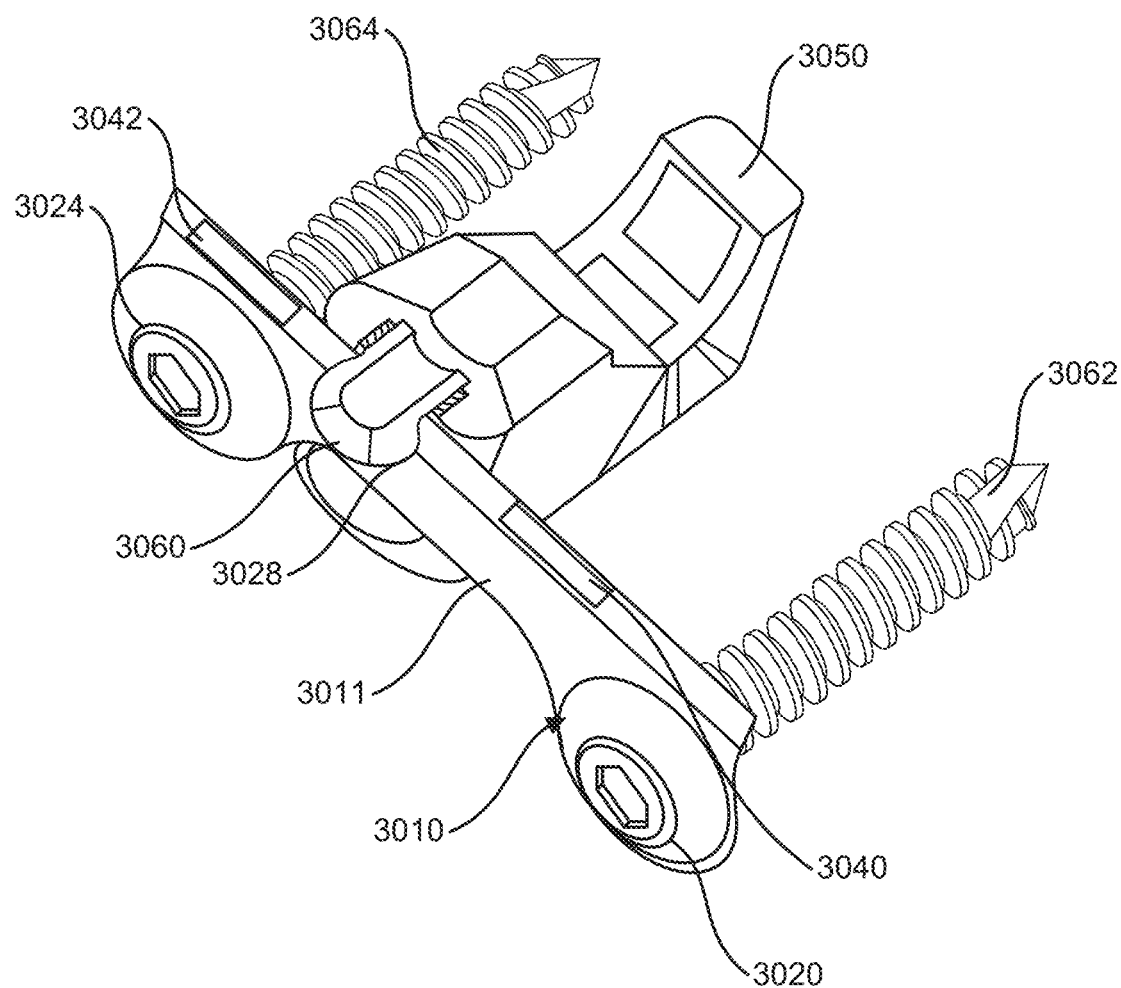
FIG. 90 shows a view of the bone fixation device in combination with a wedge.

FIG. 90 shows another view which includes the insert device 3010 including body section 3011 with mesh sections 3040 and 3042. There are a plurality of fasteners 3060, 3062, and 3064 which are configured to fasten the body 3011 to either the wedge section 3050 using fastener 3060 or to an adjacent bone using fasteners 3062 and 3064. which are configured to fasten the plate structure to the adjacent bone. Thus, when fasteners 3062 and 3064 are fastened to adjacent bone, this causes adjacent mesh sections 3040 and 3042 to be clamped to adjacent bone and to cause those mesh sections 3040 and 3042 to interact with adjacent bone. The wedge 3050 can be configured to fit between two pieces of bone to allow continued bone growth via the mesh region of the wedge 3050.

Figure 91:
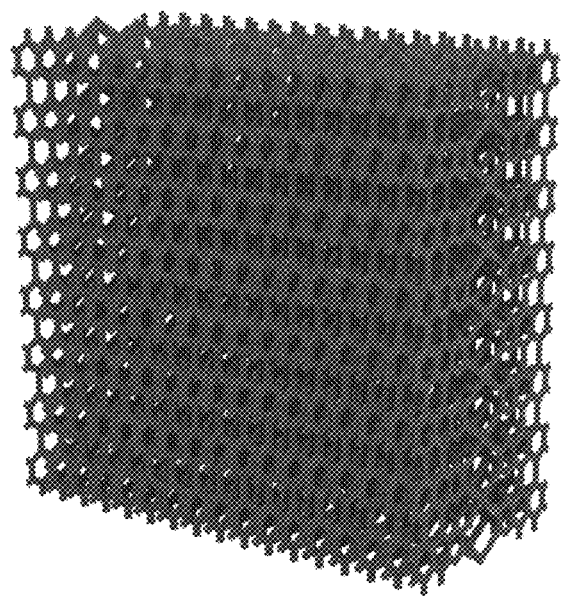
FIG. 91 show a side-front perspective view of a lattice structure of a mesh section.
Figure 92:
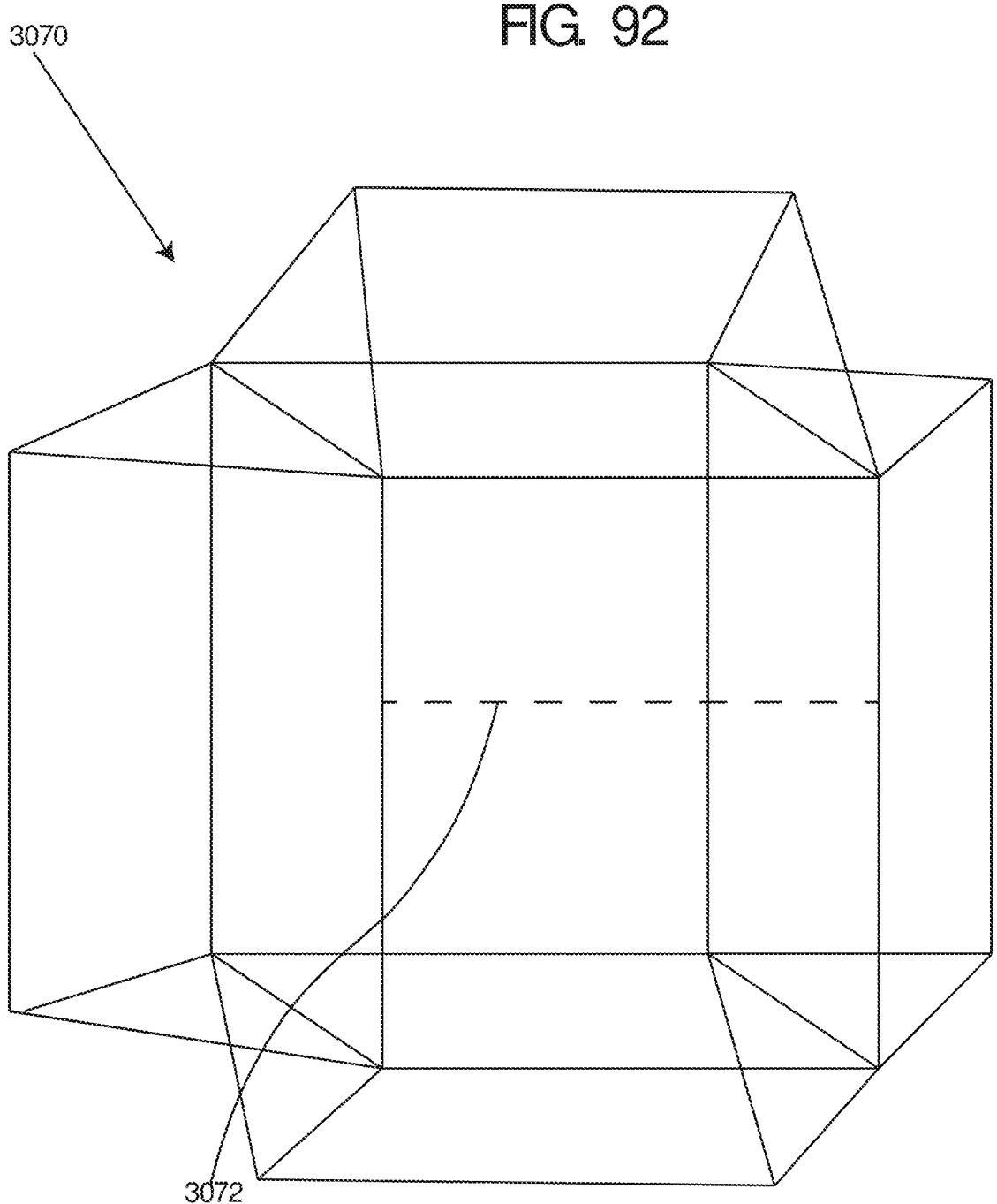
FIG. 92 shows a front perspective view of another lattice structure of a mesh section.

FIG. 91 discloses a mesh section such as a mesh section 3040 or 3042 which has a lattice having a particular pattern, such as a honeycomb structure, a hexagonal shape structure, and/or a diamond structure which can have varying porosity as indicated in FIGS. 87A-87D above. FIG. 92 shows an example of a honeycomb structure 3070 of one cell of the mesh or lattice structure. With the honeycomb structure, the porosity can be varied by varying an opening such as opening 3072 in the honeycomb structure.

The mesh sections 3056 either in the wedge 3050 itself or in the mesh sections 3040 and 3042, can vary in porosity because sections of larger porosity can be used to receive more biological material promoting bone growth. In addition, the larger porosity sections of the mesh sections create more openings to receive portions of a bone for adhering to a bone. These porous or mesh sections can have a variable porosity profile such as that disclosed in FIGS. 87A to 87D.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. A fixation device for promoting fusion and/or osteosynthesis of a first bone segment and a second bone segment, the fixation device comprising:
 a bone plate portion including an outer surface, an inner surface and at least one fixation aperture extending from the outer surface to the inner surface; and
 a bone wedge portion extending from the plate portion at a first end to a free opposite end, the bone wedge portion comprising:
 a framework structure comprising a plurality of interconnected substantially solid frame members that form a wedge shape frame with a plurality of cavities; and
 a lattice structure extending within the cavities of the framework structure comprising a plurality of strut elements that define a plurality of pores, the plurality of strut elements and pores forming a porous architecture with a variable porosity configured to promote bone ingrowth,
 wherein the wedge portion defines first and second engagement sides for engaging a first bone segment and a second bone segment, respectively, and an inner aperture that extends between the first and second engagement sides that is free of said lattice structure and configured to receive bone growth material therein to promote growth of new bone material,
 wherein the porous architecture has a plurality of different layers, at least two different layers of said plurality of different layers have a different porosity, and
 wherein said framework structure forms a first outer side surface at the first engagement side of the bone wedge portion, and wherein the lattice structure extends beyond the first outer side surface.

2. The fixation device as in claim 1, wherein the lattice structure has at least one of a variable pattern or a substantially consistent pattern of the plurality of strut elements and pores.

3. The fixation device as in claim 1, wherein the porous architecture comprises at least one cell that is shaped in at least one of a honeycomb or diamond shaped pattern.

4. The fixation device as in claim 1, wherein said framework structure forms a second outer side surface at the second engagement side of the bone wedge portion, and wherein the lattice structure extends beyond the second outer side surface.

5. The fixation device as in claim 4, wherein the first and second outer side surfaces forms first and second outer planes.

6. The fixation device as in claim 4, wherein the lattice structure forms at least two different planar surfaces, wherein said at least two different planar surfaces extend substantially transverse to each other.

7. The fixation device as in claim 1, wherein the lattice structure forms at least one surface that extends beyond the first outer side surface in a rounded manner.

8. The fixation device as in claim 1, wherein the bone wedge portion is tapered in shape from the first end to the free opposite end.

9. The fixation device as in claim 1, wherein the plate portion and the wedge portion are of one-piece construction.

10. The fixation device of claim 1, further comprising at least one fixation aperture that extends into the wedge portion to one of the first and second engagement sides.

11. The fixation device of claim 1, wherein the inner aperture of the wedge portion is bounded by the framework structure.

12. The fixation device as in claim 1, wherein said bone wedge portion has a substantially rough outer surface formed by the lattice structure.

13. The fixation device of claim 1, further including at least one bone fixation member extending through the at least one fixation aperture.

14. The fixation device of claim 1, wherein the plate portion includes at least one open aperture extending from the outer surface to the wedge portion.

15. A bone wedge comprising:
a frame portion comprising a plurality of interconnected substantially solid frame members that form a plurality of cavities; and
a porous portion extending from within the cavities of the frame portion, the porous portion comprising a lattice structure comprising a plurality of strut elements that define a plurality of pores, the plurality of strut elements and pores forming a porous architecture configured to promote bone ingrowth, the porous portion defining opposing first and second bone engagement surfaces for engaging a first bone segment and a second bone segment, respectively, wherein the porous architecture has a plurality of different layers, wherein at least two different layers of said plurality of different layers have a different porosity, and wherein the first and second bone engagement surfaces taper toward each other as they extend from a first end to a second end of the bone wedge,
wherein the bone wedge defines an inner aperture that extends between the first and second engagement surfaces that is free of said lattice structure and configured to receive bone growth material therein to promote growth of new bone material, and
wherein the frame portion forms a first outer side on the same side of the bone wedge as the first engagement surface of the porous portion that is recessed from the first engagement surface.

16. The bone wedge as in claim 15, wherein the first outer side of wherein the first outer side of the frame forms at least a first outer plane.

17. The bone wedge as in claim 16, wherein the lattice structure forms at least two different planar surfaces, wherein said at least two different planar surfaces extend substantially transverse to each other.

18. The bone wedge as in claim 16, wherein the lattice structure forms at least one surface that extends beyond the first outer plane in a rounded manner.

19. The bone wedge as in claim 15, further comprising at least one fixation aperture that extends into the porous portion.

20. The fixation device as in claim 15, wherein the frame portion forms a second outer side surface on the same side of the bone wedge as the second engagement surface of the porous portion that is recessed from second engagement surface.

\* \* \* \* \*